US012559767B2

(12) United States Patent
Li et al.

(10) Patent No.: US 12,559,767 B2
(45) Date of Patent: Feb. 24, 2026

(54) MODIFICATION OF TRANSCRIPTIONAL REPRESSOR BINDING SITE IN NF-YC4 PROMOTER FOR INCREASED PROTEIN CONTENT AND RESISTANCE TO STRESS

(71) Applicant: Iowa State University Research Foundation, Inc., Ames, IA (US)

(72) Inventors: Ling Li, Starkville, MS (US); Eve Syrkin Wurtele, Ames, IA (US)

(73) Assignee: Iowa State University Research Foundation, Inc., Ames, IA (US)

( * ) Notice: Subject to any disclaimer, the term of this patent is extended or adjusted under 35 U.S.C. 154(b) by 0 days.

(21) Appl. No.: 18/679,743

(22) Filed: May 31, 2024

(65) Prior Publication Data

US 2024/0301437 A1     Sep. 12, 2024

Related U.S. Application Data

(60) Division of application No. 18/057,439, filed on Nov. 21, 2022, now Pat. No. 12,037,594, which is a division of application No. 16/840,354, filed on Apr. 4, 2020, now Pat. No. 11,542,520, which is a continuation of application No. 15/550,781, filed as application No. PCT/US2016/018358 on Feb. 17, 2016, now Pat. No. 10,640,781.

(60) Provisional application No. 62/244,131, filed on Oct. 20, 2015, provisional application No. 62/117,924, filed on Feb. 18, 2015.

(51) Int. Cl.
*C12N 15/82* (2006.01)
*C07K 14/415* (2006.01)

(52) U.S. Cl.
CPC ........ *C12N 15/8251* (2013.01); *C07K 14/415* (2013.01); *C12N 15/8205* (2013.01); *C12N 15/8216* (2013.01); *C12N 15/8241* (2013.01); *C12N 15/8247* (2013.01); *C12N 15/8279* (2013.01)

(58) Field of Classification Search
None
See application file for complete search history.

(56) References Cited

U.S. PATENT DOCUMENTS

| | | |
|---|---|---|
| 8,030,546 B2 | 10/2011 | Reuber et al. |
| 2005/0086718 A1 | 4/2005 | Heard et al. |
| 2008/0040973 A1 | 2/2008 | Nelson et al. |
| 2010/0173776 A1 | 7/2010 | Schade et al. |
| 2010/0223689 A1* | 9/2010 | Ratcliffe ............ C12N 15/8262 |
| | | 800/290 |
| 2012/0222167 A1 | 8/2012 | Li et al. |
| 2016/0083745 A1 | 3/2016 | Li et al. |
| 2018/0030465 A1 | 2/2018 | Li et al. |

FOREIGN PATENT DOCUMENTS

| | | |
|---|---|---|
| CN | 102575253 A | 7/2012 |
| CN | 103509094 A | 1/2014 |
| JP | 2005304409 A | 11/2005 |
| WO | 2008021021 A2 | 2/2008 |
| WO | 2014144761 A2 | 9/2014 |

OTHER PUBLICATIONS

Doerks et al., (TIG, 14:248-250, 1998).*
Smith et al. (Nature Biotechnology, 15:1222-1223, 1997).*
Bork et al. (TIG, 12:425-427, 1996).*
Murai-Takeda et al. (Journal of Biological Chemistry, 285:8084-8093; Published 2010).*
Liu et al. (Nat Commun. 7:12768. Published Sep. 14, 2016. doi:10.1038/ncomms12768).*
Ling et al. (PNAS, 112:14734-14739; Published Nov. 24, 2015).*
Ikeda et al. (Plant Cell Physiol., 50:970-975, 2009).*
Kagaya et al. (Nucleic Acids Research, 27:470-478, 1999).*
Nakamura et al. (GenBank Sequence Accession No. AB007649.1; 2004).*
Xie et al. (Molecular Plant, 6:1975-1983, 2013).*
Doerks et al., "Protein annotation: detective work for function prediction," TIG 14(6): 248-250, 1998.
Smith et al., "The challenges of genome sequence annotation or The devil is in the details," Nature Biotechnology 15: 1222-1223 1997.
Bork et al., "Go hunting in sequence databases but watch out for the traps," TIG 12(10); 425-427, 1996 1996.
Murai-Takeda et al., "NF-YC Functions as a Corepressor of Agonist-bound Mineralocorticoid Receptor," J. Biological Chem., 285(11): 8084-8093 2010.
Liu et al., "The NF-YC_RGL2 module integrates GA and ABA signaling to regulate seed germination in *Arabidopsis*," Nat Comm 7: 12768 (doi: 10.1038/ncomms12768) 2016.
Li et al., "QQS orphan gene regulates carbon and nitrogen partitioning across species via NF-YC Interactions," PNAS, 112(47): 14734-14739, 2015.

(Continued)

*Primary Examiner* — Vinod Kumar
(74) *Attorney, Agent, or Firm* — McKee, Voorhees & Sease, PLC

(57) ABSTRACT

Method of increasing protein content in a eukaryotic cell comprising an NF-YC4 gene comprising modifying the transcriptional repressor binding site; method of producing a plant with increased protein content comprising crossing and selecting for increased protein content; method of increasing resistance to a pathogen or a pest in a plant cell or plant comprising an NF-YC4 gene comprising modifying the transcriptional repressor binding site, alone or in further combination with expressing QQS in the plant cell or plant; method for producing a plant with increased resistance to a pathogen or a pest comprising crossing and selecting for increased resistance to the pathogen or the pest; a cell, collection of cells, tissue, organ, or organism, such as a plant, in which the NF-YC4 gene comprises a promoter comprising a transcriptional repressor binding site that has been modified so that the transcriptional repressor cannot prevent transcription of the NF-YC4; plants and hybrids thereof; and seeds.

16 Claims, 26 Drawing Sheets

Specification includes a Sequence Listing.

(56) References Cited

OTHER PUBLICATIONS

Cao et al., "Cloning and Functional Analysis of GmNF-YC2 Gene in Soybean (*Glycine max*)", Acta Agronomica Sinica, vol. 38(9), pp. 1607-1616, 2012.

China National Intellectual Property Administration in connection with application 201680022422.6 filed Feb. 17, 2016, "Search Report", 2 pages, mailed Jul. 16, 2020.

Ikeda et al., "A novel group of transcriptional repressors in *Arabidopsis*," Plant Cell Physiol 50(5): 970-975, 2009.

Kagaya et al., "RAV1, a novel DNA-binding protein, binds to bipartite recognition sequence through two distinct DNA-binding domains uniquely found in higher plants," Nucl Acids Res 27(2): 470-478, 1999.

Kumimoto et al., "NF-YC3, NF-YC4 and NF-YC9 are required for CONSTANS-mediated, photoperiod-dependent flowering in *Arabidopsis thaliana*," Plant Journal, 63(3): 379-391, 2010.

Li et al., "The QQS orphan gene of *Arabidopsis* modulates carbon and nitrogen allocation in soybean," Plant Biotechnology Journal, 13: 177-187, 2015.

Search Report and Written Opinion issued in App. No. PCT/US2016/018358 2016.

Xu et al. "Multiple Nuclear Factor Y transcription factors respond to abiotic stress in *Brassica napus* L." PloS one 9.10 (2014): 1-11.

* cited by examiner

GCAAGAACCCCAGTTGAGAGTGGAGATGGCCATTTTGTTCAGGCACTAGGCAGTGGGTAGGACGGTGAGGAGTGTGT
CCTGCACTCCTGCTTCCCCTGACGATCGATCCCCATGCGTGCCGAAGCATCTGATACTTTTGCTGTGCTGTTCTTTA
ATTTACCCTGATACTTTTGGATATCTGAAGCAGTAGAGCTCGTTCACTCAAACAGGCTAGCCTGTTTTGCTTTCTGG
TAAGAACTTAATTAACTAGTTGAGATCGACATGCATGGATGCGTGAATCTATTGTTGCATTTTTTCTAATGGATAGT
TAGATTTGTTCCAGCTTTTTTTTTGTCAATTCTGTTACATTTGCAGTGTCTTCAACTTCTGCATCATTCTTCTCTAT
TCTTCCTTCACTTTCTTTCTTGAACTAGAAAAGCAAACCAGAGTTCTTTTTCCCCCTCTTCTACATAAACGAAAACA
GCTTGTTGACTGGCTCCCTAGAGCTTTTTGTAAGTTGATCATCGAAGTAGCTAGTTCTCTTCACTTATC*AGTCA*TCA
CTGTTCTATGTTCTATCTGCATTTTCCTTGATTTTGTACTTTTCCTGAACGAAAGGACAATCCTTAGCCATCATAAT
GCTATGATCGACTTATTCTGA*AGTCA*TCCGGCCTCGATCCTCTTTTGTTTCGGTGAGATCTGTAATGGTTTAGGAAA
ATTATGGATCTCTGAAAAATAAGAAACATCTAGTAGTATATGAAATTAAGAAATGTCGGACCACGTCAAATCCTACT
GGTATCATATACCAGATAACTAACTTTTTGAATGGAACCAAACACGAGATTGTGAATATATAGCAGTAAGAAATACA
ACCCCGAAGGGTAAAGGAGAAAAAGGAAAAGCAGTTAGTGTACGAGCTGTAGGAGTAGCTTTGCTCCTGCCAAGGC
CCAGATCCTTGCCTCTTCCTTCATTTCTGCGAGGAGACCAGGCACTGAGGTCTCATTGTGATCGAAGATTCTCCTGT
TTCTCTCCTTCCAGATCTCCTTTGGGAACACCCTGTGTGTTTGCAAGCGCTTAGCTTCATTTTCATGCATGATATGA
TCTCTGGATAGAAGATAAGTAGCCCCCACACATGCACTTCGCCACCTATAGCCAGCCTCGAGTTCTCATCTGTTTGA
TCCGTCGCACATGTGGAGCAACGAAGCTCTAGAGTACGTCTCCTAATCTCTACTTACTTTTGCAGTTTGCACACATA
TTGAGAAATGCTTATCAATCCTTCGATCTCTCACAGACAATACCTACAAGCGTCGTTTACACTTTGCATGTATAGCT
AGCCATTGTTACATACGTGGAGCATGTAGCGATCATTCGTTCCTAGCACGTAAATTAATCGCCGTAATTTTGCCCAT
GCAGACACAGCACACACAGCTACAAATCGACTGTAATTAAGGTACGTATATATAGGTGACA [SEQ ID NO: 1]

GCAAGAACCCCAGTTGAGAGTGGAGATGGCCATTTTGTTCAGGCACTAGGCAGTGGGTAGGACGGTGAGGAGTGTGT
CCTGCACTCCTGCTTCCCCTGACGATCGATCCCCATGCGTGCCGAAGCATCTGATACTTTTGCTGTGCTGTTCTTTA
ATTTACCCTGATACTTTTGGATATCTGAAGCAGTAGAGCTCGTTCACTCAAACAGGCTAGCCTGTTTTGCTTTCTGG
TAAGAACTTAATTAACTAGTTGAGATCGACATGCATGGATGCGTGAATCTATATTTTTTCTAATGGATAGTTAGATT
TGTTCCAGCTTTTTTTTTGTCAATTCTGTTACATTTGCAGTGTCTTCAACTTCTGCATCATTCTTCTCTATTCTTCC
TTCACTTTCTTTCTTGAACTAGAAAAGCAAACCAGAGTTCTTTTTCCCCCTCTTCTACATAAACGAAAACAGCTTGT
TGACTGGCTCCCTAGAGCTTTTTGTAAGTTGATCATCGAAGTAGCTAGTTCTCTTCACTTATC*AGTCA*TCACTGTTC
TATGTTCTATCTGCATTTTCCTTGATTTTGTACTTTTCCTGAACGAAAGGACAATCCTTAGCCATCATAATGCTATG
ATCGACTTATTCTGA*AGTCA*TCCGGCCTCGATCCTCTTTTGTTTCGGTGAGATCTGTAATGGTTTAGGAAAATTATG
GATCTCTGAAAAATAAGAAACATCTAGTAGTATATGAAATTAAGAAATGTCGGACCACGTCAAATCCTACTGGTATC
ATATACCAGATAACTAACTTTTTGAATGGAACCAAACACGAGATTGTGAATATATAGCAGTAAGAAATACAACCCCG
AAGGGTAAAGGAGAAAAAGGAAAAGCAGTTAGTGTACGAGCTGTAGGAGTAGCTTTGCTCCTGCCAAGGCCCAGAT
CCTTGCCTCTTCCTTCATTTCTGCGAGGAGACCAGGCACTGAGGTCTCATTGTGATCGAAGATTCTCCTGTTTCTCT
CCTTCCAGATCTCCTTTGGGAACACCCTGTGTGTTTGCAAGCGCTTAGCTTCATTTTCATGCATGATATGATCTCTG
GATAGAAGATAAGTAGCCCCCACACATGCACTTCGCCACCTATAGCCAGCCTCGAGTTCTCATCTGTTTGATCCGTC
GCACATGTGGAGCAACGAAGCTCTAGAGTACGTCTCCTAATCTCTACTTACTTTTGCAGTTTGCACACATATTGAGA
AATGCTTATCAATCCTTCGATCTCTCACAGACAATACCTACAAGCGTCGTTTACACTTTGCATGTATAGCTAGCCAT
TGTTACATACGTGGAGCATGTAGCGATCATTCGTTCCTAGCACGTAAATTAATCGCCGTAATTTTGCCCATGCAGAC
ACAGCACACACAGCTACAAATCGACTGTAATTAAGGTACGTATATATAGGTGACA [SEQ ID NO: 2]

FIG. 2A

GCAAGAACCCCAGTTGAGAGTGGAGATGGCCATTTTGTTCAGGCACTAGGCAGTGGGTAGGACGGTGAGGAGTGTGT
CCTGCACTCCTGCTTCCCCTGACGATCGATCCCCATGCGTGCCGAAGCATCTGATACTTTTGCTGTGCTGTTCTTTA
ATTTACCCTGATACTTTTGGATATCTGAAGCAGTAGAGCTCGTTCACTCAAACAGGCTAGCCTGTTTTGCTTTCTGG
TAAGAACTTAATTAACTAGTTGAGATCGACATGCATGGATGCGTGAATCTATTGTTGCATTTTTTCTAATGGATAGT
TAGATTTGTTCCAGCTTTTTTTTTGTCAATTCTGTTACATTTGCAGTGTCTTCAACTTCTGCATCATTCTTCTCTAT
TCTTCCTTCACTTTCTTTCTTGAACTAGAAAAGCAAACCAGAGTTCTTTTTCCCCCTCTTCTACATAAACGAAAACA
GCTGGCTCCCTAGAGCTTTTTGTAAGTTGATCATCGAAGTAGCTAGTTCTCTTCACTTATCAGTCATCACTGTTCTA
TGTTCTATCTGCATTTTCCTTGATTTTGTACTTTTCCTGAACGAAAGGACAATCCTTAGCCATCATAATGCTATGAT
CGACTTATTCTGAAGTCATCCGGCCTCGATCCTCTTTTGTTTCGGTGAGATCTGTAATGGTTTAGGAAAATTATGGA
TCTCTGAAAAATAAGAAACATCTAGTAGTATATGAAATTAAGAAATGTCGGACCACGTCAAATCCTACTGGTATCAT
ATACCAGATAACTAACTTTTTGAATGGAACCAAACACGAGATTGTGAATATATAGCAGTAAGAAATACAACCCCGAA
GGGTAAAGGAGAAAAAGGAAAAGCAGTTTAGTGTACGAGCTGTAGGAGTAGCTTTGCTCCTGCCAAGGCCCAGATCC
TTGCCTCTTCCTTCATTTCTGCGAGGAGACCAGGCACTGAGGTCTCATTGTGATCGAAGATTCTCCTGTTTCTCTCC
TTCCAGATCTCCTTTGGGAACACCCTGTGTGTTTGCAAGCGCTTAGCTTCATTTTCATGCATGATATGATCTCTGGA
TAGAAGATAAGTAGCCCCCACACATGCACTTCGCCACCTATAGCCAGCCTCGAGTTCTCATCTGTTTGATCCGTCGC
ACATGTGGAGCAACGAAGCTCTAGAGTACGTCTCCTAATCTCTACTTACTTTTGCAGTTTGCACACATATTGAGAAA
TGCTTATCAATCCTTCGATCTCTCACAGACAATACCTACAAGCGTCGTTTACACTTTGCATGTATAGCTAGCCATTG
TTACATACGTGGAGCATGTAGCGATCATTCGTTCCTAGCACGTAAATTAATCGCCGTAATTTTGCCCATGCAGACAC
AGCACACACAGCTACAAATCGACTGTAATTAAGGTACGTATATATAGGTGACA [SEQ ID NO: 3]

GCAAGAACCCCAGTTGAGAGTGGAGATGGCCATTTTGTTCAGGCACTAGGCAGTGGGTAGGACGGTGAGGAGTGTGT
CCTGCACTCCTGCTTCCCCTGACGATCGATCCCCATGCGTGCCGAAGCATCTGATACTTTTGCTGTGCTGTTCTTTA
ATTTACCCTGATACTTTTGGATATCTGAAGCAGTAGAGCTCGTTCACTCAAACAGGCTAGCCTGTTTTGCTTTCTGG
TAAGAACTTAATTAACTAGTTGAGATCGACATGCATGGATGCGTGAATCTATTGTTGCATTTTTTCTAATGGATAGT
TAGATTTGTTCCAGCTTTTTTTTTGTCAATTCTGTTACATTTGCAGTGTCTTCAACTTCTGCATCATTCTTCTCTAT
TCTTCCTTCACTTTCTTTCTTGAACTAGAAAAGCAAACCAGAGTTCTTTTTCCCCCTCTTCTACATAAACGAAAACA
GCTTGTTGACTGGCTCCCTAGAGCTTTTTGTAAGTTGATCATCGAAGTAGCTAGTTCTCTTCACTTATCTCCGGCCT
CGATCCTCTTTTGTTTCGGTGAGATCTGTAATGGTTTAGGAAAATTATGGATCTCTGAAAAATAAGAAACATCTAGT
AGTATATGAAATTAAGAAATGTCGGACCACGTCAAATCCTACTGGTATCATATACCAGATAACTAACTTTTTGAATG
GAACCAAACACGAGATTGTGAATATATAGCAGTAAGAAATACAACCCCGAAGGGTAAAGGAGAAAAAGGAAAAGCAG
TTTAGTGTACGAGCTGTAGGAGTAGCTTTGCTCCTGCCAAGGCCCAGATCCTTGCCTCTTCCTTCATTTCTGCGAGG
AGACCAGGCACTGAGGTCTCATTGTGATCGAAGATTCTCCTGTTTCTCTCCTTCCAGATCTCCTTTGGGAACACCCT
GTGTGTTTGCAAGCGCTTAGCTTCATTTTCATGCATGATATGATCTCTGGATAGAAGATAAGTAGCCCCCACACATG
CACTTCGCCACCTATAGCCAGCCTCGAGTTCTCATCTGTTTGATCCGTCGCACATGTGGAGCAACGAAGCTCTAGAG
TACGTCTCCTAATCTCTACTTACTTTTGCAGTTTGCACACATATTGAGAAATGCTTATCAATCCTTCGATCTCTCAC
AGACAATACCTACAAGCGTCGTTTACACTTTGCATGTATAGCTAGCCATTGTTACATACGTGGAGCATGTAGCGATC
ATTCGTTCCTAGCACGTAAATTAATCGCCGTAATTTTGCCCATGCAGACACAGCACACACAGCTACAAATCGACTGT
AATTAAGGTACGTATATATAGGTGACA [SEQ ID NO: 4]

AGTCATCACTGTTCTATGTTCTATCTGCATTTTCCTTGATTTTGTACTTTTCCTGAACGAAAGGACAATCCTTAGCC
ATCATAATGCTATGATCGACTTATTCTGAAGTCA [SEQ ID NO: 5]

FIG. 2B

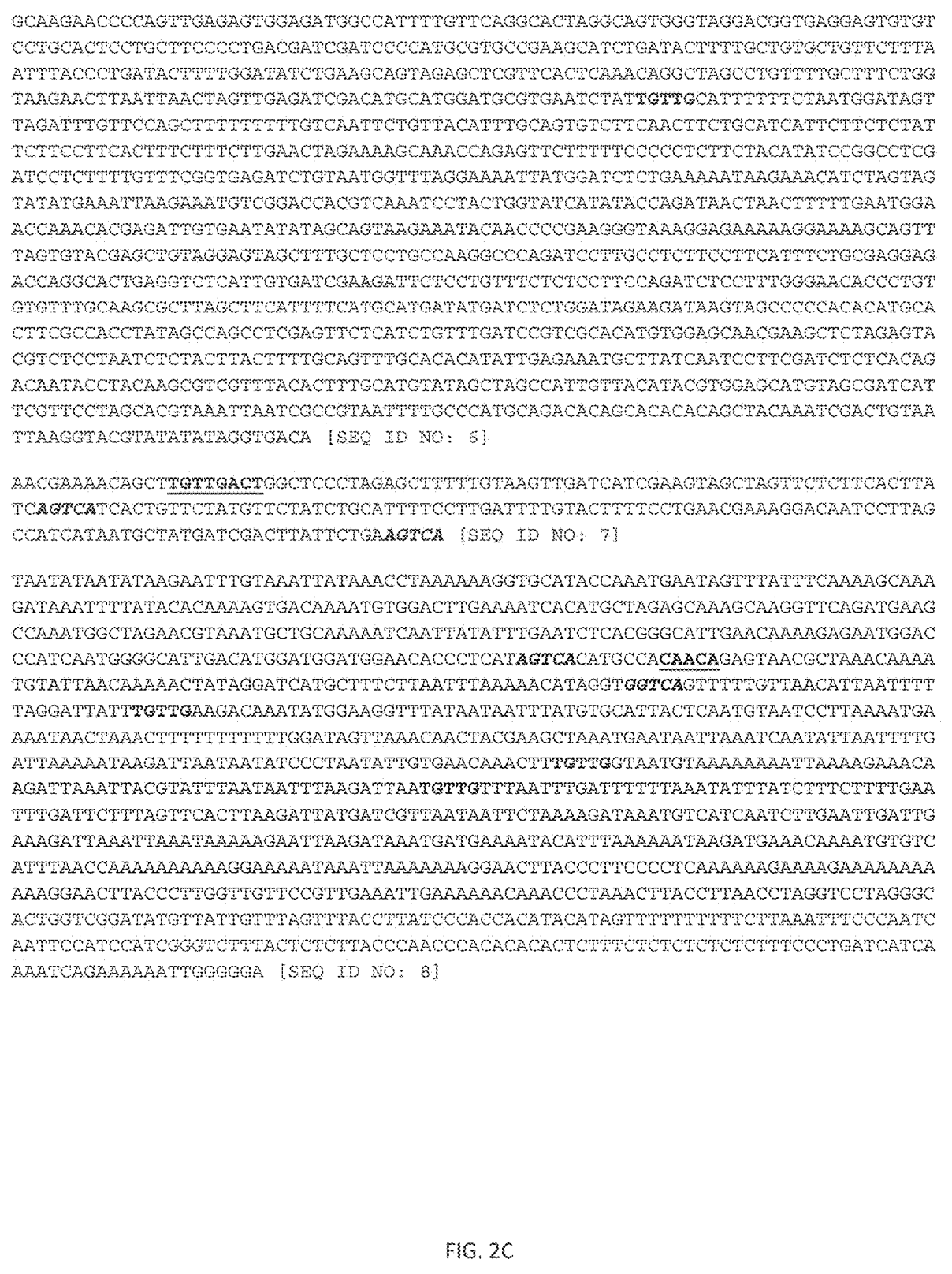

GCAAGAACCCCAGTTGAGAGTGGAGATGGCCATTTTGTTCAGGCACTAGGCAGTGGGTAGGACGGTGAGGAGTGTGT
CCTGCACTCCTGCTTCCCCTGACGATCGATCCCCATGCGTGCCGAAGCATCTGATACTTTTGCTGTGCTGTTCTTTA
ATTTACCCTGATACTTTTGGATATCTGAAGCAGTAGAGCTCGTTCACTCAAACAGGCTAGCCTGTTTTGCTTTCTGG
TAAGAACTTAATTAACTAGTTGAGATCGACATGCATGGATGCGTGAATCTATTGTTGCATTTTTTCTAATGGATAGT
TAGATTTGTTCCAGCTTTTTTTTTGTCAATTCTGTTACATTTGCAGTGTCTTCAACTTCTGCATCATTCTTCTCTAT
TCTTCCTTCACTTTCTTTCTTGAACTAGAAAAGCAAACCAGAGTTCTTTTTCCCCCTCTTCTACATATCCGGCCTCG
ATCCTCTTTTGTTTCGGTGAGATCTGTAATGGTTTAGGAAAATTATGGATCTCTGAAAAATAAGAAACATCTAGTAG
TATATGAAATTAAGAAATGTCGGACCACGTCAAATCCTACTGGTATCATATACCAGATAACTAACTTTTTGAATGGA
ACCAAACACGAGATTGTGAATATATAGCAGTAAGAAATACAACCCCGAAGGGTAAAGGAGAAAAAGGAAAAGCAGTT
TAGTGTACGAGCTGTAGGAGTAGCTTTGCTCCTGCCAAGGCCCAGATCCTTGCCTCTTCCTTCATTTCTGCGAGGAG
ACCAGGCACTGAGGTCTCATTGTGATCGAAGATTCTCCTGTTTCTCTCCTTCCAGATCTCCTTTGGGAACACCCTGT
GTGTTTGCAAGCGCTTAGCTTCATTTTCATGCATGATATGATCTCTGGATAGAAGATAAGTAGCCCCCACACATGCA
CTTCGCCACCTATAGCCAGCCTCGAGTTCTCATCTGTTTGATCCGTCGCACATGTGGAGCAACGAAGCTCTAGAGTA
CGTCTCCTAATCTCTACTTACTTTTGCAGTTTGCACACATATTGAGAAATGCTTATCAATCCTTCGATCTCTCACAG
ACAATACCTACAAGCGTCGTTTACACTTTGCATGTATAGCTAGCCATTGTTACATACGTGGAGCATGTAGCGATCAT
TCGTTCCTAGCACGTAAATTAATCGCCGTAATTTTGCCCATGCAGACACAGCACACACAGCTACAAATCGACTGTAA
TTAAGGTACGTATATATAGGTGACA [SEQ ID NO: 6]

AACGAAAACAGCTTGTTGACTGGCTCCCTAGAGCTTTTTGTAAGTTGATCATCGAAGTAGCTAGTTCTCTTCACTTA
TC*AGTCA*TCACTGTTCTATGTTCTATCTGCATTTTCCTTGATTTTGTACTTTTCCTGAACGAAAGGACAATCCTTAG
CCATCATAATGCTATGATCGACTTATTCTGA*AGTCA* [SEQ ID NO: 7]

TAATATAATATAAGAATTTGTAAATTATAAACCTAAAAAAGGTGCATACCAAATGAATAGTTTATTTCAAAAGCAAA
GATAAATTTTATACACAAAAGTGACAAAATGTGGACTTGAAAATCACATGCTAGAGCAAAGCAAGGTTCAGATGAAG
CCAAATGGCTAGAACGTAAATGCTGCAAAAATCAATTATATTTGAATCTCACGGGCATTGAACAAAAGAGAATGGAC
CCATCAATGGGGCATTGACATGGATGGATGGAACACCCTCAT*AGTCA*CATGCCACAACAGAGTAACGCTAAACAAAA
TGTATTAACAAAAACTATAGGATCATGCTTTCTTAATTTAAAAACATAGGT*GGTCA*GTTTTTGTTAACATTAATTTT
TAGGATTATTTGTTGAAGACAAATATGGAAGGTTTATAATAATTTATGTGCATTACTCAATGTAATCCTTAAAATGA
AAATAACTAAACTTTTTTTTTTTGGATAGTTAAACAACTACGAAGCTAAATGAATAATTAAATCAATATTAATTTTG
ATTAAAAATAAGATTAATAATATCCCTAATATTGTGAACAAACTTTGTTGGTAATGTAAAAAAAATTAAAAGAAACA
AGATTAAATTACGTATTTAATAATTTAAGATTAATGTTGTTTAATTTGATTTTTTAAATATTTATCTTTCTTTTGAA
TTTGATTCTTTAGTTCACTTAAGATTATGATCGTTAATAATTCTAAAAGATAAATGTCATCAATCTTGAATTGATTG
AAAGATTAAATTAAATAAAAAGAATTAAGATAAATGATGAAAATACATTTAAAAAATAAGATGAAACAAAATGTGTC
ATTTAACCAAAAAAAAAGGAAAAATAAATTAAAAAAAGGAACTTACCCTTCCCCTCAAAAAAGAAAAGAAAAAAAA
AAAGGAACTTACCCTTGGTTGTTCCGTTGAAATTGAAAAAACAAACCCTAAACTTACCTTAACCTAGGTCCTAGGGC
ACTGGTCGGATATGTTATTGTTTAGTTTACCTTATCCCACCACATACATAGTTTTTTTTTTCTTAAATTTCCCAATC
AATTCCATCCATCGGGTCTTTACTCTCTTACCCAACCCACACACACTCTTTCTCTCTCTCTTTCCCTGATCATCA
AAATCAGAAAAAATTGGGGGA [SEQ ID NO: 8]

FIG. 2C

```
TAATATAATATAAGAATTTGTAAATTATAAACCTAAAAAAGGTGCATACCAAATGAATAGTTTATTTCAAAAGCAAA
GATAAATTTTATACACAAAAGTGACAAAATGTGGACTTGAAAATCACATGCTAGAGCAAAGCAAGGTTCAGATGAAG
CCAAATGGCTAGAACGTAAATGCTGCAAAAATCAATTATATTTGAATCTCACGGGCATTGAACAAAAGAGAATGGAC
CCATCAATGGGGCATTGACATGGATGGATGGAACACCCTCATGAGTAACGCTAAACAAAATGTATTAACAAAAACTA
TAGGATCATGCTTTCTTAATTTAAAAACATAGGT*GGTCA*GTTTTTGTTAACATTAATTTTTAGGATTATTTGTTGAA
GACAAATATGGAAGGTTTATAATAATTTATGTGCATTACTCAATGTAATCCTTAAAATGAAAATAACTAAACTTTTT
TTTTTTGGATAGTTAAACAACTACGAAGCTAAATGAATAATTAAATCAATATTAATTTTGATTAAAAATAAGATTAA
TAATATCCCTAATATTGTGAACAAACTTTGTTGGTAATGTAAAAAAAATTAAAAGAAACAAGATTAAATTACGTATT
TAATAATTTAAGATTAATGTTGTTTAATTTGATTTTTTAAATATTTATCTTTCTTTTGAATTTGATTCTTTAGTTCA
CTTAAGATTATGATCGTTAATAATTCTAAAAGATAAATGTCATCAATCTTGAATTGATTGAAAGATTAAATTAAATA
AAAAGAATTAAGATAAATGATGAAAATACATTTAAAAAATAAGATGAAACAAAATGTGTCATTTAACCAAAAAAAAA
AGGAAAAATAAATTAAAAAAAGGAACTTACCCTTCCCCTCAAAAAAGAAAAGAAAAAAAAAAAGGAACTTACCCTTG
GTTGTTCCGTTGAAATTGAAAAAACAAACCCTAAACTTACCTTAACCTAGGTCCTAGGGCACTGGTCGGATATGTTA
TTGTTTAGTTTACCTTATCCCACCACATACATAGTTTTTTTTTTTCTTAAATTTCCCAATCAATTCCATCCATCGGGT
CTTTACTCTCTTACCCAACCCACACACACTCTTTCTCTCTCTCTTTCCCTGATCATCAAAATCAGAAAAAATTGG
GGGA [SEQ ID NO: 9]
```

*AGTCA*CATGCCA<u>CAACA</u> [SEQ ID NO: 10]

```
TAATATAATATAAGAATTTGTAAATTATAAACCTAAAAAAGGTGCATACCAAATGAATAGTTTATTTCAAAAGCAAA
GATAAATTTTATACACAAAAGTGACAAAATGTGGACTTGAAAATCACATGCTAGAGCAAAGCAAGGTTCAGATGAAG
CCAAATGGCTAGAACGTAAATGCTGCAAAAATCAATTATATTTGAATCTCACGGGCATTGAACAAAAGAGAATGGAC
CCATCAATGGGGCATTGACATGGATGGATGGAACACCCTCAT*AGTCA*CATGCCA<u>CAACA</u>GAGTAACGCTAAACAAAA
TGTATTAACAAAAACTATAGGATCATGCTTTCTTAATTTAAAAACATAGGTAAGACAAATATGGAAGGTTTATAATA
ATTTATGTGCATTACTCAATGTAATCCTTAAAATGAAAATAACTAAACTTTTTTTTTTTGGATAGTTAAACAACTAC
GAAGCTAAATGAATAATTAAATCAATATTAATTTTGATTAAAAATAAGATTAATAATATCCCTAATATTGTGAACAA
ACTTTGTTGGTAATGTAAAAAAAATTAAAAGAAACAAGATTAAATTACGTATTTAATAATTTAAGATTAATGTTGTT
TAATTTGATTTTTTAAATATTTATCTTTCTTTTGAATTTGATTCTTTAGTTCACTTAAGATTATGATCGTTAATAAT
TCTAAAAGATAAATGTCATCAATCTTGAATTGATTGAAAGATTAAATTAAATAAAAAGAATTAAGATAAATGATGAA
AATACATTTAAAAAATAAGATGAAACAAAATGTGTCATTTAACCAAAAAAAAAAGGAAAAATAAATTAAAAAAAGGA
ACTTACCCTTCCCCTCAAAAAAGAAAAGAAAAAAAAAAAGGAACTTACCCTTGGTTGTTCCGTTGAAATTGAAAAAA
CAAACCCTAAACTTACCTTAACCTAGGTCCTAGGGCACTGGTCGGATATGTTATTGTTTAGTTTACCTTATCCCACC
ACATACATAGTTTTTTTTTTTCTTAAATTTCCCAATCAATTCCATCCATCGGGTCTTTACTCTCTTACCCAACCCACA
CACACTCTTTCTCTCTCTCTTTCCCTGATCATCAAAATCAGAAAAAATTGGGGGA [SEQ ID NO: 11]
```

*GGTCA*GTTTTTGTTAACATTAATTTTTAGGATTATTTGTTG [SEQ ID NO: 12]

FIG. 2D

TAATATAATATAAGAATTTGTAAATTATAAACCTAAAAAAGGTGCATACCAAATGAATAGTTTATTTCAAAAGCAAA
GATAAATTTTATACACAAAAGTGACAAAATGTGGACTTGAAAATCACATGCTAGAGCAAAGCAAGGTTCAGATGAAG
CCAAATGGCTAGAACGTAAATGCTGCAAAAATCAATTATATTTGAATCTCACGGGCATTGAACAAAAGAGAATGGAC
CCATCAATGGGGCATTGACATGGATGGATGGAACACCCTCAT*AGTCA*CATGCCA<u>CAACA</u>GAGTAACGCTAAACAAAA
TGTATTAACAAAAACTATAGGATCATGCTTTCTTAATTTAAAAACATAGGT*GGTCA*GTTTTTGTTAACATTAATTTT
TAGGATTATT*TGTT*GAAGACAAATATGGAAGGTTTATAATAATTTATGTGCATTACTCAATGTAATCCTTAAAAATGA
AAATAACTAAACTTTTTTTTTTTGGATAGTTAAACAACTACGAAGCTAAATGAATAATTAAATCAATATTAATTTTG
ATTAAAAATAAGATTAATAATATCCCTAATATTGTGAACAAACTTTTTAATTTGATTTTTTAAATATTTATCTTTCT
TTTGAATTTGATTCTTTAGTTCACTTAAGATTATGATCGTTAATAATTCTAAAAGATAAATGTCATCAATCTTGAAT
TGATTGAAAGATTAAATTAAATAAAAAGAATTAAGATAAATGATGAAAATACATTTAAAAAAATAAGATGAAACAAAA
TGTGTCATTTAACCAAAAAAAAAAGGAAAAATAAATTAAAAAAAGGAACTTACCCTTCCCCTCAAAAAAGAAAAGAA
AAAAAAAAAGGAACTTACCCTTGGTTGTTCCGTTGAAATTGAAAAAACAAACCCTAAACTTACCTTAACCTAGGTCC
TAGGGCACTGGTCGGATATGTTATTGTTTAGTTTACCTTATCCCACCACATACATAGTTTTTTTTTTTCTTAAATTTC
CCAATCAATTCCATCCATCGGGTCTTTACTCTCTTACCCAACCCACACACACTCTTTCTCTCTCTCTTTCCCTGA
TCATCAAAATCAGAAAAAATTGGGGGA [SEQ ID NO: 13]

*TGTT*GGTAATGTAAAAAAAATTAAAAGAAACAAGATTAAATTACGTATTTAATAATTTAAGATTAA*TGTTG* [SEQ
ID NO: 14]

ctcagaagaa  gcctcctttc  gatctgtcag  ccattgaaga  aacctccttt  cgatctgtca  60
gccattgaag  atcagaagaa  acaagactca  cacggtcagc  cattgaagaa  gcctcctctc  120
attacctctc  atcaaacatc  tagatctgta  cccaaacctt  atcccttttt  ccttatttct  180
cgctttgtct  attcttaatc  tgattaatac  ttgttgttgt  tccaggttat  agaagatctg  240
ggttgtgtta  tatgcttcat  tttctccaca  gcgaccagtt  ggtgtttggt  tcttagattc  300
atgaagacca  atagagagca  ggaaatttac  gttgaaagaa  gcttcaaacc  aaacaattca  360
acaattcaga  atttgatgga  cattgaaagg  ttcatttttgc  ctcacacttc  tacatcaggt  420
gtcgcaaggc  tcaaaatgag  ggtcatatca  tgggtcgggc  ttcagttcta  caactactga  480
tattgggcct  tatcacaaat  tagttatagg  gccattgtat  ccaatattta  atatctctgt  540
aaacttgttt  aatggttatt  ttgttctaat  gcccattaca  actaga [SEQ ID NO: 15]

Met Lys Thr Asn Arg Glu Gln Glu Ile Tyr Val Glu Arg Ser Phe Lys
1               5                   10                  15
Pro Asn Asn Ser Thr Ile Gln Asn Leu Met Asp Ile Glu Arg Phe Ile
            20                  25                  30
Leu Pro His Thr Ser Thr Ser Gly Val Ala Arg Leu Lys Met Arg Val
        35                  40                  45
Ile Ser Trp Val Gly Leu Gln Phe Tyr Asn Tyr [SEQ ID NO: 16]

GGTCAGTTTTTGTTAACATTAATTTTTAGGAT [SEQ ID NO: 17]

CCTCCCAGGCATGGCAGTCC [SEQ ID NO: 18]

CCATCAAGGCTCCGCTGG [SEQ ID NO: 19]

FIG. 2E

AGGGCCCTGCAGCGGCGGCAGCTGGCGGGAGAGAGGCTTGGGACTGGGCC
GCCCGGCCGCGAGGAATAAACTCACTCCTGTCTTCATACGTATCCATAGC
CGGCAGGCGGCAGTACCTGTATGTGGTTTTAGCTATACGCGACCTCAGTT
CGGGCGCAAGGTTAGTCTTCGATTTAAGCATAGATTTTATTTTATCTTCT
TGGCTCCACCAAATAACACTAACAAAATCGCTTTGGCTTCTATGGGTTCA
AATTAAGCACTGGATCGTACCATTTTCTTGTTCATTTATACTTTGTCATC
CAATCCACACCGATTAATTTCTCACGGTCAACAACGCATGAAGTTTTCAT
TTCTGGGAAGAAGCATGTATTTTTTTTATCTCCGACTCGATCTAGTGGTG
AGAGGAGGAAGATGAATAGTGCATGCATATGATATCTAGAGAGGCACCAG
ATCTAGTGGCTCCATGTTCTGTTCGCGGGCTAAGAAAAAACATAAACAAG
CAGGCGCCTGAAAAATAGCTAGTCCCTAACTTTTTAGACCAATCTGTATG
TTTATTTTGACGATATTGGTATGAAAAAGTCTCTCAAGAACAATATACAT
ATGCAGCATGCATGTGCATGGTATAATTATAAATTATTAGCAGAGTTTAG
ATAAGTAGGCCCCCACGTCTGCGCTCCGCCACCTACAGCGAGCCTCCCTT
TCCTCCCTCCCTGATTCGTTTGCACTTGCTGAGAGCTCAACAGAATTTGG
TCACCGATTTCAATTCGCAGCTACTAATTCTCACCACATTGAAATTTTCG
ATTTGAAACAGTACAATTTCTGAAGAGAAATTGTACGTCTGAAACGGTTG
CATGTGTACTATGAACTGCTAGCCATTCCCTGCATACGTGGGACACGCTC
AGATCATTCATTCGCAGCACGTACGTAACCTTAATATTCTACTATACATC
CATGCAGCTACAACCCCGACCAGGCGAGAAGAAGCATCGATAGTGTGACG
AGCTAACCCACCACCAGCAACGTAATCCAAATCC [SEQ ID NO: 20]

FIG. 2F

MODIFICATION OF TRANSCRIPTIONAL REPRESSOR BINDING SITE IN NF-YC4 PROMOTER FOR INCREASED PROTEIN CONTENT AND RESISTANCE TO STRESS

CROSS REFERENCE TO RELATED APPLICATION

This application is a divisional of U.S. application Ser. No. 18/057,439, filed Nov. 21, 2022, which is a divisional of U.S. application Ser. No. 16/840,354, filed Apr. 4, 2020, now U.S. Pat. No. 11,542,520, issued Jan. 3, 2023, which is a continuation of U.S. application Ser. No. 15/550,781, filed Aug. 13, 2017, now U.S. Pat. No. 10,640,781 issued May 5, 2020, as the U.S. National Phase of International Application No. PCT/US2016/018358, which was filed Feb. 17, 2016, with a claim of priority to U.S. Provisional Application No. 62/117,924, filed Feb. 18, 2015, and U.S. Provisional Application No. 62/244,131, filed Oct. 20, 2015. All of the aforementioned applications are incorporated herein by reference in their entireties.

STATEMENT REGARDING FEDERALLY SPONSORED RESEARCH OR DEVELOPMENT

The work described herein was supported, at least in part, by grants from the National Science Foundation under MCB award nos. 0209789 and 0951170. Therefore, the Government of the United States of America has certain rights in the invention.

SEQUENCE LISTING XML

The instant application contains a sequence listing, which has been submitted in XML file format by electronic submission and is hereby incorporated by reference in its entirety. Said XML file, created on Nov. 21, 2022, is named P13242US04.xml and is 31,921 bytes in size.

TECHNICAL FIELD

The present disclosure relates to increasing protein content in a eukaryotic cell, increasing a plant's resistance to stress, such as abiotic (e.g., salt, drought, and pollution) or biotic (e.g., pathogens and pests) stress, a promoter with a modified transcriptional repressor binding site, such that the transcriptional repressor cannot prevent transcription of the gene, NF-YC4, QQS, TALENS, CRISPR/Cas9, tissue culture, crossing and backcrossing plants, hybrid plants, regenerable cells, and seeds.

BACKGROUND

Protein deficiency is a major health problem throughout the developing world. Low protein intake contributes to mental retardation, stunting, susceptibility to disease, wasting diseases and/or death in hundreds of millions of children each year (Forrester et al., PloS one 7: c35907 (2012); Gomes et al., J. Neuroscience Res. 87: 3568-3575 (2009)).

Plants provide over 60% of human dietary protein (Young et al., Am. J. Clin. Nutr. 59: 1203S-1212S (1994)). Increasing the protein content of staple crops could help alleviate protein deficiency, particularly when the use of animals requires about 100 times more water and 11 times more energy to produce an equivalent amount of protein (Pimentel et al., Am. J. Clin. Nutr. 78: 6605-6635 (2003)) and increasing the protein content of animals is often accompanied by a decrease in protein quality or yield (Bellaloui et al., Agricultural Sciences 1: 110-118 (2010); Wenefrida et al., J. Agricultural Food Chem. 61: 11702-11710 (2013)).

The *Arabidopsis thaliana* QQS (At3g30720, Qua-Quine Starch) orphan gene modulates protein content in *Arabidopsis*. *Arabidopsis thaliana* starch synthase 3 (Atss3) mutants, which are morphologically similar to wild-type (WT) control lines but differ in starch levels (Zhang et al., Plant Physiol. 138: 663-674 (2005)), have more than five-fold the amount of QQS transcripts found in WT (Li et al., Plant J. 58: 485-498 (2009)). Over-expression of QQS in *Arabidopsis* increases total protein content and decreases total starch content in leaves, while down-regulation of QQS has the converse effect (Li et al., Plant Biotech. J. 13: 177-187 (2015); Li et al. (2009), supra). Expression of QQS as a transgene increases protein content in other plants, such as soybean (var. Williams 82; Li et al. (2014), supra; Li et al. (2009), supra).

QQS expression has been observed to be tightly linked with a variety of developmental, environmental, and genetic perturbations (see, e.g., Arendsee et al., Trends in Plant Sci doi: 10.1016/j.tplants.2014.07.003 (2014); Li et al. (2009), supra; and Li et al. (2015), supra). Its role, however, in such perturbations has not been elucidated. For example, PEN3 (Penetration Resistance 3 (At1g59870, PEN3, ABC binding cassette transporter gene) confers non-host resistance to fungal and oomycete pathogens. QQS has been reported to be the only gene that is up-regulated in pen3 knock-out (KO) mutants; however, QQS is up-regulated in infected and non-infected mutants (Stein et al., Plant Cell 18(3): 731-746 (2006)). As another example, two syntaxins, namely SYP121 (At3g11820, PEN1) and SYP122 (At3g52400) confer resistance to powdery mildews. Knock-outs of these genes result in increased sensitivity to these pathogens; QQS has been reported to be the only gene that is up-regulated in both (Zhang et al. (2008)). In contrast, while PEN3 and EXL1 are up-regulated following exposure to some pathogens, QQS is down-regulated in response to infection by some pathogens, such as *Pseudomonas syringae* (Kwon et al., Planta 236(3): 887-900 (2012); and Thilmony et al., Plant J. 46(1): 34-53 (2006)). When *Arabidopsis* plants were inoculated with *Phytopthera infestans*, QQS reportedly was first down-regulated at 6 hrs post-inoculation and then up-regulated at 12 and 24 hrs post-inoculation (Scheel et al., Experiment ID "E-GEOD-5616" in ArrayExpress).

Thus, in view of the above, it is an object of the present disclosure to identify a gene with which QQS interacts. In *Arabidopsis* QQS interacts with nuclear factor Y, subunit C4 (NF-YC4, At5g63470). It is another object to provide materials and methods for manipulating a gene so identified. In an embodiment, the manipulation of such a gene results in increased protein content and/or decreased carbohydrate content. It is yet another object to provide materials and a method for increasing a plant's resistance to a pathogen or a pest. These and other objects, as well as inventive features, will be apparent from the detailed description provided herein.

SUMMARY

A method of increasing protein content in a eukaryotic cell comprising an NF-YC4 gene, which comprises a promoter comprising a transcriptional repressor binding site, is provided. The method comprises modifying the transcriptional repressor binding site, whereupon the transcriptional repressor cannot prevent transcription of the NF-YC4. Protein content in the eukaryotic cell is increased; thus, the method can further comprise selecting for increased protein content. The method can further comprise generating a collection of cells, a tissue, an organ, or an organism from the eukaryotic cell. The eukaryotic cell can be a part of a collection of cells, a tissue, an organ, or an organism. The organism can be a plant, such as a crop plant, such as soybean, rice, corn, or the like. The plant can be a monocot or a dicot. The transcriptional repressor binding site can be modified by a deletion. The transcriptional repressor binding site can comprise, consist essentially of, or consist of an ERF motif, a RAV1 motif, or both an ERF motif and a RAV1 motif. The eukaryotic cell can be a rice cell and (i) two ERF motifs are deleted, (ii) a RAF1 motif is deleted, or (iii) a RAV1 motif and an ERF motif are deleted. The eukaryotic cell can be a soybean cell and either (i) two RAV1 motifs are deleted or (ii) a RAV1 motif and an ERF motif are deleted. An ERF motif, a RAV1 motif, or both an ERF motif and a RAV1 motif can be deleted using TALENS or CRISPR/Cas9.

A method of producing a plant with increased protein content is also provided. The method comprises crossing a plant obtained in accordance with the above method with a second plant to produce progeny plants and selecting progeny plants with increased protein content. The method can further comprise crossing selected progeny plants with the second plant to produce backcross progeny plants, selecting a first backcross progeny plant that has increased protein content to produce selected backcross progeny plants, and repeating the crossing and selecting three or more times to produce a backcross progeny plant that has increased protein content.

A cell, collection of cells, tissue, organ, or organism in which the NF-YC4 gene comprises a promoter comprising a transcriptional repressor binding site that has been modified so that the transcriptional repressor cannot prevent transcription of the NF-YC4 is also provided. The cell, collection of cells, tissue, organ, or organism has an increased protein content compared to a corresponding cell, collection of cells, tissue, organ, or organism in which the NF-YC4 gene comprises a promoter comprising a transcriptional repressor binding that has not been modified. In an embodiment, the organism can be a plant or a hybrid thereof. A seed of the aforementioned plant or hybrid thereof is also provided. In another embodiment, the organism can be a non-human animal, such as livestock animals, e.g., cattle, pigs, chickens, turkeys, sheep, and bison.

Further provided is a method of increasing resistance to a pathogen or a pest in a plant cell or plant, which comprises an NF-YC4 gene, which comprises a promoter comprising a transcriptional repressor binding site. The method comprises modifying the transcriptional repressor binding site of the promoter of the NF-YC4 gene in a plant cell or a plant at risk of infection with a pathogen or a pest so that a transcriptional repressor cannot prevent transcription of the NF-YC4 gene. Resistance to the pathogen or the pest is increased in the plant cell or plant; thus, the method can further comprise selecting for increased resistance to a pathogen or a pest. The method can further comprise introducing into the plant or plant cell and expressing therein a polynucleotide comprising a nucleotide sequence encoding a Qua-Quine Starch (QQS) polypeptide having the amino acid sequence as set forth in SEQ ID NO: 16, wherein the nucleotide sequence is operably linked to a promoter. The method can further comprise regenerating a plant or part thereof from the plant cell. The transcriptional repressor binding site can comprise an ERF motif, a RAV1 motif, or both an ERF motif and a RAV1 motif. The plant cell or plant can be a rice cell or a rice plant and (i) two ERF motifs are deleted, (ii) a RAF1 motif is deleted, or (iii) a RAV1 motif and an ERF motif are deleted. The plant cell or plant can be a soybean cell or a soybean plant and either (i) two RAV1 motifs are deleted or (ii) a RAV1 motif and an ERF motif are deleted. An ERF motif, a RAV1 motif, or both an ERF motif and a RAV1 motif can be deleted using TALENS or CRISPR/Cas9. The pathogen can be a bacterium or a virus. The pest can be an aphid. The plant can be a crop plant, such as soybean. The plant can be a dicot.

Still further provided is a method of producing a plant with increased resistance to a pathogen or a pest. The method comprises crossing a plant obtained in accordance with the above with a second plant to produce progeny plants and selecting progeny plants with increased resistance to the plant pathogen or pest. The method can further comprise crossing selected progeny plants with the second plant to produce backcross progeny plants, selecting a first backcross progeny plant that has increased resistance to a pathogen or a pest to produce selected backcross progeny plants, and repeating the crossing and selecting three or more times to produce a backcross progeny plant that has increased resistance to a pathogen or a pest.

Even still further provided is a plant, which has increased resistance to a pathogen or pest. The plant comprises an NF-YC4 gene comprising a promoter comprising a transcriptional repressor binding site. The transcriptional repressor binding site has been modified so that the transcriptional repressor cannot prevent transcription of the NF-YC4. In an embodiment of the plant, the wild-type of which does not comprise and express QQS, a polynucleotide comprising a nucleotide sequence encoding a QQS polypeptide having the amino acid sequence as set forth in SEQ ID NO: 16 has been introduced and expressed. The nucleotide sequence is operably linked to a promoter.

A seed of the aforementioned plant is also provided, as is a hybrid of the plant. A seed of the hybrid plant is also provided.

BRIEF DESCRIPTION OF THE FIGURES

FIGS. 2A, 2B, 2C, 2D, 2E and 2F show sequences that are relevant to the present disclosure as follows:

Figure 1A:
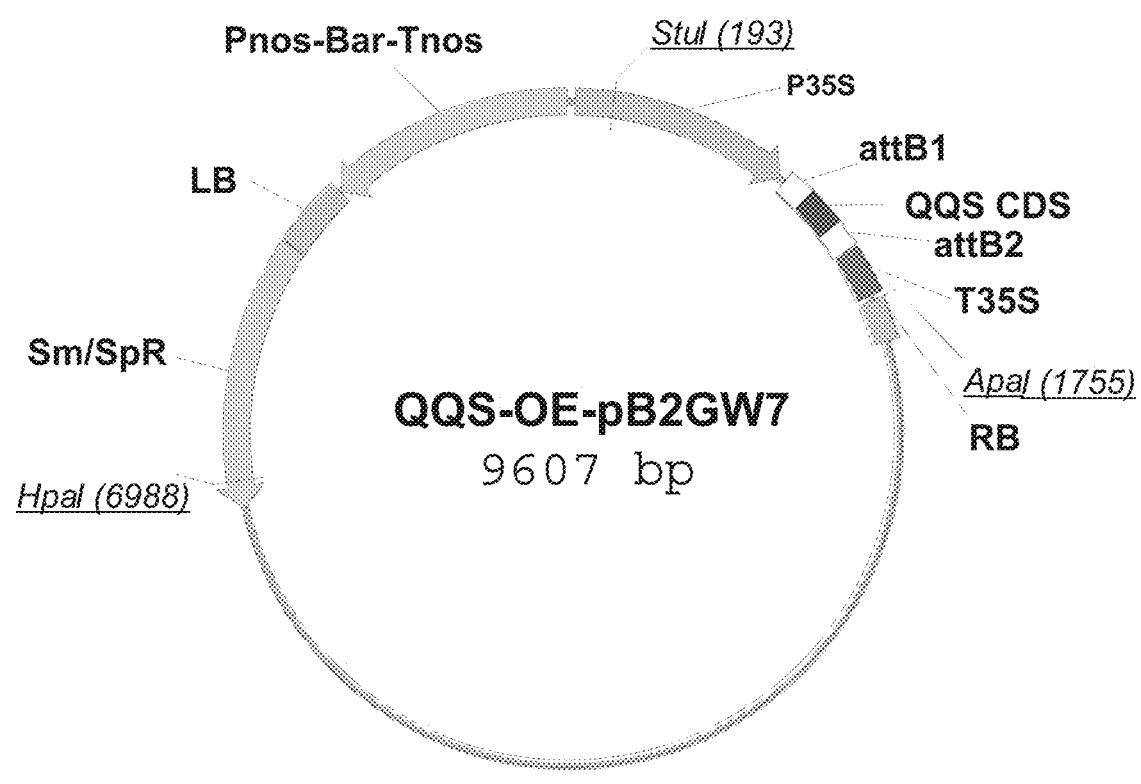
FIG. 1A is a map of a vector expressing QQS.
Figure 1B:
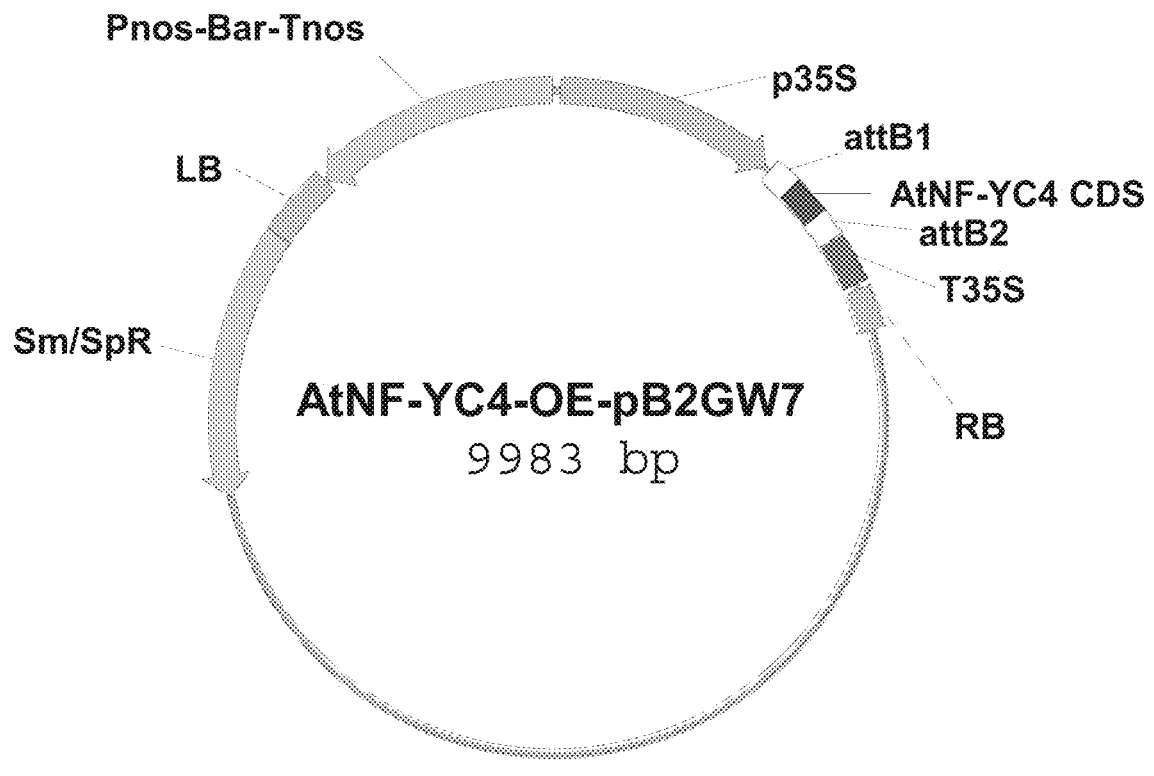
FIG. 1B is a map of a vector expressing NF-YC4 from *Arabidopsis.*

A promoter region of the NF-YC4 gene of *Oryza sativa* (Os03g14669) is shown as SEQ ID NO: 1, in which a RAV1 motif (reverse) is shown in bold, a RAV1 (reverse) and ERF (forward) motif is shown in underlined bold, and ERF motifs (reverse) are shown in italicized bold.

A promoter region of the NF-YC4 gene of *Oryza sativa* in which a RAV1 (reverse) motif (TGTTG; see bold in SEQ ID NO: 1) has been deleted is shown as SEQ ID NO: 2, in which a RAV1 (reverse) and ERF (forward) motif is shown in underlined bold and ERF motifs (reverse) are shown in italicized bold.

A promoter region of the NF-YC4 gene of *Oryza sativa* in which overlapping sequences of a RAV1 (reverse) motif and an ERF (forward) motif (TGTTGACT; see underlined bold in SEQ ID NO: 1) have been deleted is shown as SEQ ID NO: 3, in which a RAV1 motif (reverse) is shown in bold, and ERF motifs (reverse) are shown in italicized bold.

A promoter region of the NF-YC4 gene of *Oryza sativa* in which a 111 bp segment containing two ERF motifs (reverse) (AGTCATCACTGTTCTATGTTCTATCTGCATT TTCCTTGATTTTGTACTTTTCCT-GAACGAAAGGACAATCCTTAGCCATCATAATGC TATGATCGACTTATTCTGAAGTCA [SEQ ID NO: 5]; see two ERFs in bold italics in SEQ ID NO: 1 and intervening sequence) has been deleted is shown as SEQ ID NO: 4, in which a RAV1 motif (reverse) is shown in bold, and a RAV1 (reverse) and ERF (forward) motif is shown in underlined bold.

A promoter region of the NF-YC4 gene of *Oryza sativa* in which a 190 bp segment containing two ERF motifs (reverse), a RAV1 (reverse) and ERF (forward) motif, and intervening sequences (AACGAAAACAGCT GGCTCCCTAGAGCTTTT GTAAGTTGAT-CATCGAAGTAGCTAGTTCTCTTCACTTATCAGTCAT-CACTGTTCTA TGTTCTATCTGCATTTTCCTTGAT-TTTGTACTTTTCCTGAACGAAAGGACAATCCT TAGCCATCATAATGCTATGATCGACTTATTCT-GAAGTCA [SEQ ID NO: 7]; see two ERF motifs (reverse) in italicized bold, RAV1 (reverse) and ERF (forward) motif in underlined bold, and intervening sequences in SEQ ID NO: 1) have been deleted is shown as SEQ ID NO: 6, in which a RAV1 motif (reverse) is shown in bold.

A promoter region of the NF-YC4 gene of *Glycine max* (Glyma06g17780) is shown as SEQ ID NO: 8, in which ERF motifs (reverse) are shown in italicized bold, RAV1 motifs (reverse) are shown in bold, and a RAV1 motif (forward) is shown in underlined bold.

A promoter region of the NF-YC4 gene of *Glycine max* in which an ERF motif (reverse), a RAV1 motif (forward) and the intervening sequence (AGTCACATGCCACAACA [SEQ ID NO: 10]; see italicized bold and underlined bold in SEQ ID NO: 8) have been deleted is shown as SEQ ID NO: 9, in which an ERF motif (reverse) is shown in italicized bold and RAV1 motifs (reverse) are shown in bold.

A promoter region of the NF-YC4 gene of *Glycine max* in which an ERF motif (reverse), a RAV1 motif (reverse) and the intervening sequence (GGTCAGTTTTTGTT AACAT-TAATTTTTAGGATTATTTGTTG [SEQ ID NO: 12]; see italicized bold and bold in SEQ ID NO: 8) have been deleted is shown as SEQ ID NO: 11, in which an ERF motif (reverse) is shown in italicized bold, RAV1 motifs (reverse) are shown in bold, and a RAV1 motif (forward) is shown in underlined bold.

A promoter region of the NF-YC4 gene of *Glycine max* in which two RAV1 motifs and the intervening sequence ( TGTTG GTAATGTAAAAAAAATTAAAAGAAACAAGAT-TAAATTACGTATTTAATAATTTAAGATTAATGTTG [SEQ ID NO: 14]; see bold in SEQ ID NO: 8) have been deleted is shown as SEQ ID NO: 13, in which ERF motifs (reverse) are shown in italicized bold, a RAV1 motif (reverse) is shown in bold, and a RAV1 motif (forward) is shown in underlined bold.

The nucleotide sequence of the *Arabidopsis thaliana* Qua-Quine Starch (QQS) cDNA is shown as SEQ ID NO: 15.

The amino acid sequence of the *Arabidopsis thaliana* QQS protein is shown as SEQ ID NO: 16.

A nucleotide sequence from NF-YC4 of *Glycine max* between the RAV1-A motif and the W box motif having the sequence GGTCAGTTTTTGTTAACA TTAATTTTTAG-GAT is shown as SEQ ID NO: 17.

The forward primer GmNF-YC4Fd: 5'-CCTCCCAGG-CATGGCAGTCC-3' is shown as SEQ ID NO: 18.

The reverse primer GmNF-YC4Rev: 5'-CCAT-CAAGGCTCCGCTGG-3' is shown as SEQ ID NO: 19.

A promoter region of the NF-YC4 gene of *Zea mays* is shown as SEQ ID NO: 20, in which two RAV1 motifs (forward) are shown in bold.

Figure 3:
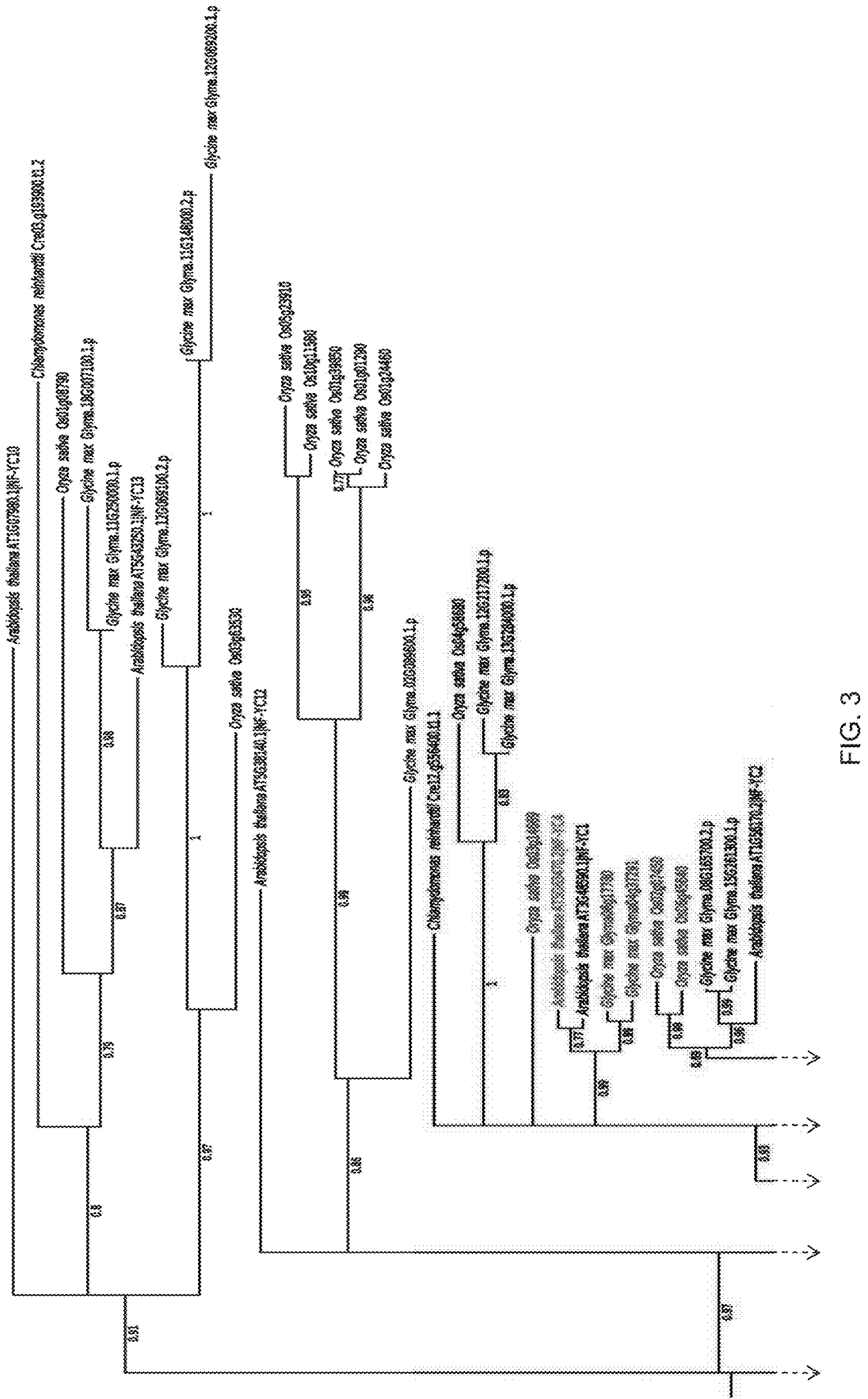
Figure 3:
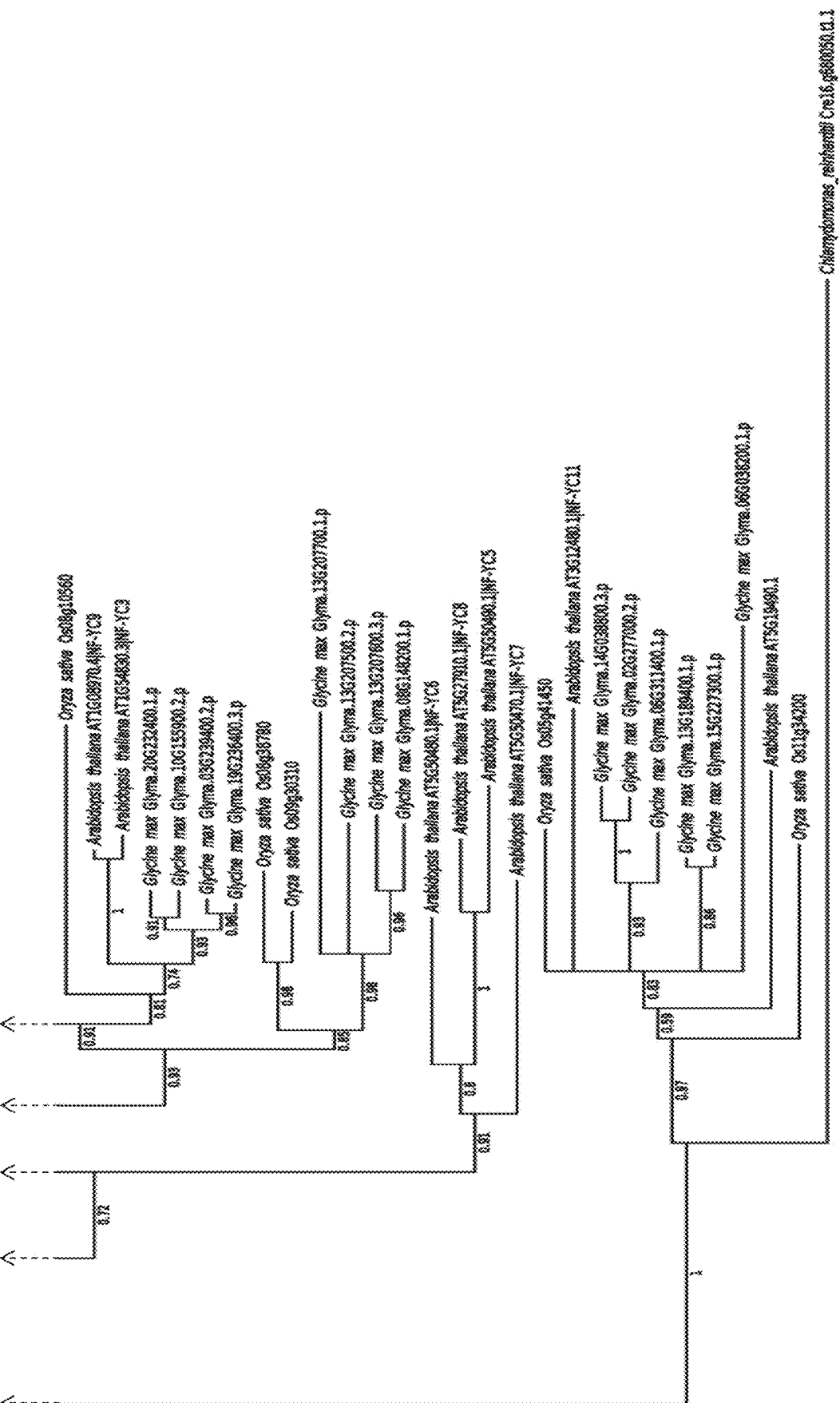

FIG. 3 is a phylogenetic tree of the NF-YC genes from evolutionarily diverse species of eukaryotes.

Figure 4B:
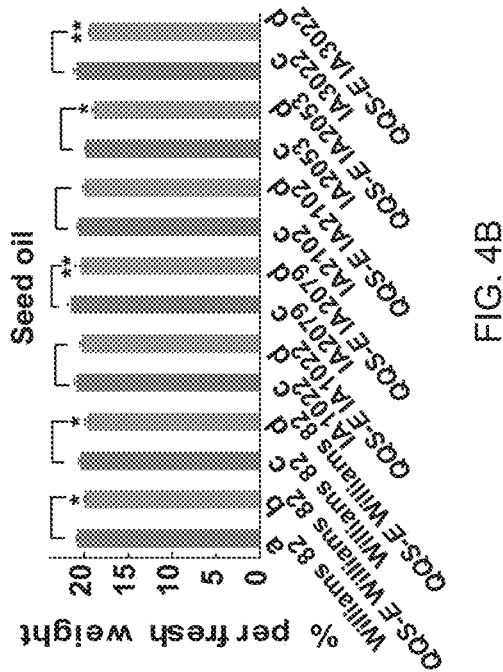
Figure 4A:
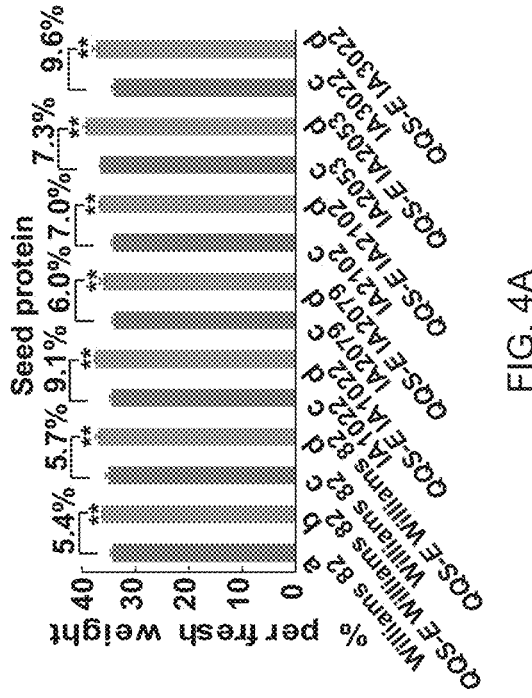

FIG. 4A is a bar graph of soybean elite lines expressing QQS and their respective segregating sibling controls vs. seed protein in the F3 generation (%/g fresh weight with 13% moisture). The percent increase in seed protein compared to the respective segregating sibling control is indicated at the top of the mutant bar. a=segregating sibling lacking the QQS gene from QQS-E Williams 82 transformants; b-QQS-E Williams 82 transformants; c=segregating sibling controls lacking the QQS gene from crosses of IA elite lines or Williams 82 and QQS-E Williams 82; d=QQS-E mutants from crosses of IA elite lines and QQS-E Williams 82. Student's t-test was used to compare QQS-E and controls. **P<0.01.

FIG. 4B is a bar graph of soybean elite lines expressing QQS and their respective segregating sibling controls vs. seed oil in the F3 generation (%/g fresh weight with 13% moisture). a=segregating sibling lacking the QQS gene from QQS-E Williams 82 transformants; b=QQS-E Williams 82 transformants; c=segregating sibling controls lacking the QQS gene from crosses of IA elite lines or Williams 82 and QQS-E Williams 82; d=QQS-E mutants from crosses of IA elite lines or Williams 82 and QQS-E Williams 82. Student's t-test was used to compare QQS-E and controls. *P<0.05. **P<0.01.

Figure 4C:
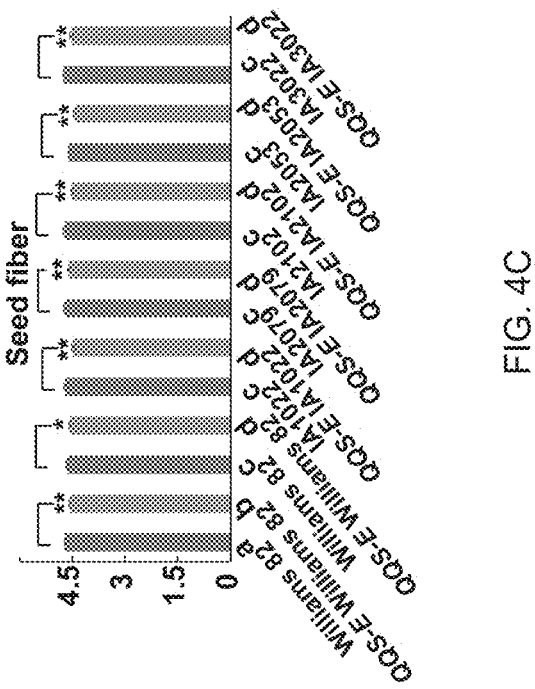

FIG. 4C is a bar graph of soybean elite lines expressing QQS and their respective segregating sibling controls vs. seed fiber in the F3 generation (%/g fresh weight with 13% moisture). a=segregating sibling lacking the QQS gene from QQS-E Williams 82 transformants; b=QQS-E Williams 82 transformants; c=segregating sibling controls lacking the QQS gene from crosses of IA elite lines or Williams 82 and QQS-E Williams 82; d=QQS-E mutants from crosses of IA elite lines or Williams 82 and QQS-E Williams 82. Student's t-test was used to compare QQS-E and controls. *P<0.05. *P<0.01.

Figure 5A:
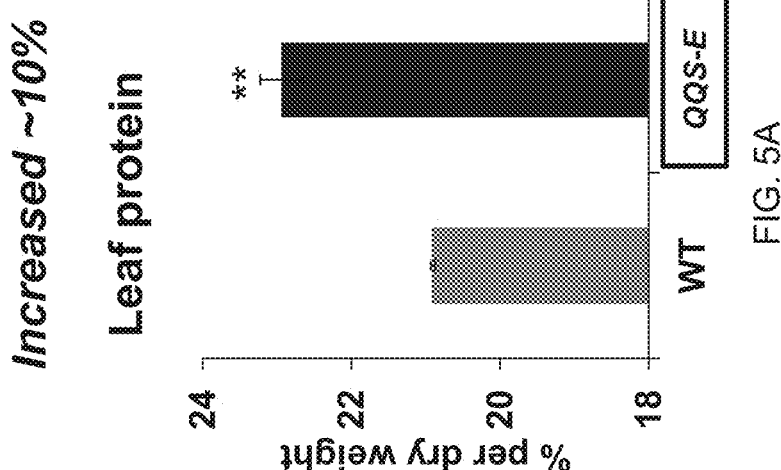

FIG. 5A is a bar graph of rice (cultivar Kitakke) expressing QQS (QQS-E) and its wild-type sibling (sibling) vs. leaf protein (%/dry weight). All data show mean±SE, n=3. Student's t-test was used to compare QQS-E and controls. **P<0.01.

Figure 5B:
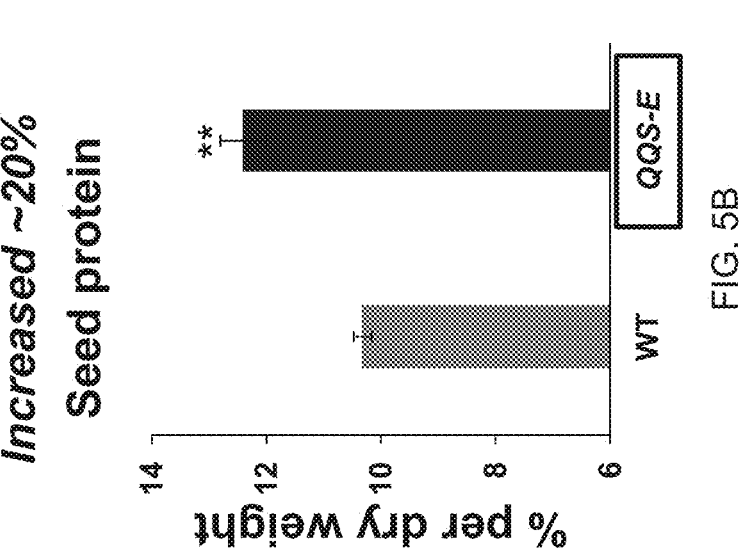

FIG. 5B is a bar graph of rice (cultivar Kitakke) expressing QQS (QQS-E) and its wild-type sibling (sibling) vs. seed protein (%/dry weight). All data show mean±SE, n=3. Student's t-test was used to compare QQS-E and controls. **P<0.01.

Figure 6:
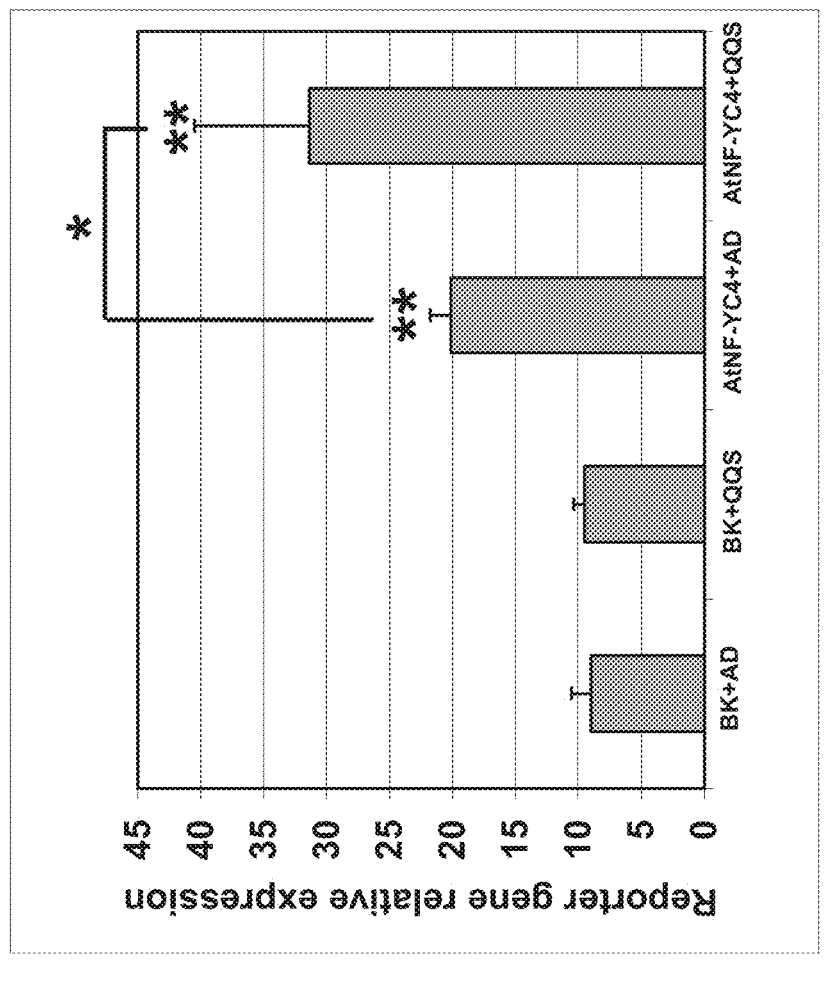

FIG. 6 is a bar graph of empty vectors of prey+bait (BK+AD), QQS-prey+empty vector of bait (BK+QQS), AtNF-YC4-bait+empty vector of prey (AtNF-YC4+AD), and AtNF-YC4-bait+QQS-prey (AtNF-YC4+QQS) plus reporter gene relative expression. *P<0.05. **P<0.01.

Figures 7A, 7B:
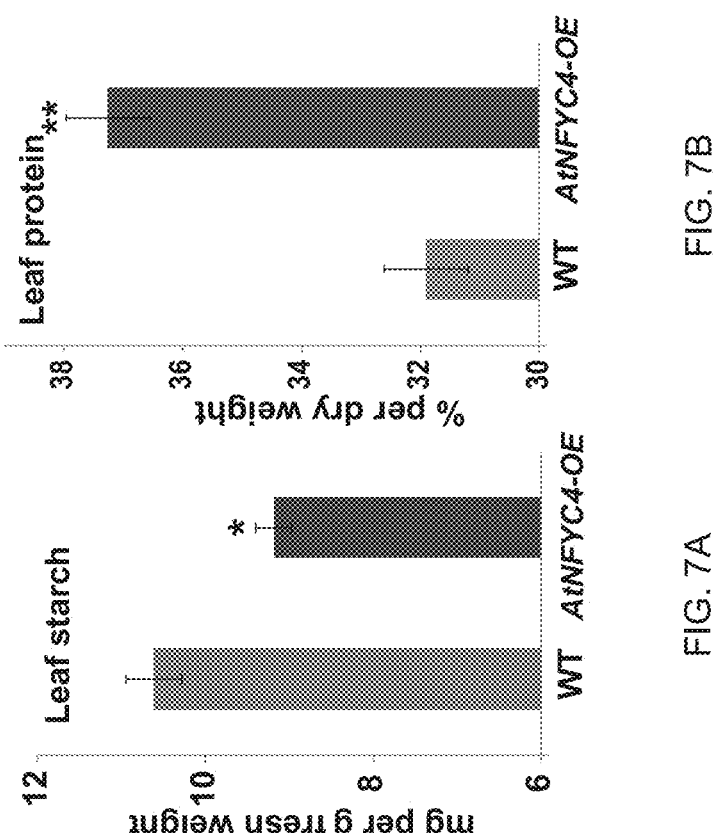

FIG. 7A is a bar graph of *Arabidopsis* over-expressing NF-YC4 (AtNF-YC4-OE) and wild-type *Arabidopsis* (WT) vs. leaf starch (mg/g fresh weight). All data in bar graph show mean±SE, n=3. Student's t-test was used to compare starch composition in the WT and AtNF-YC4-OE lines. *P<0.05.

FIG. 7B is a bar graph of *Arabidopsis* over-expressing NF-YC4 (AtNF-YC4-OE) and wild-type *Arabidopsis* (WT)

vs. leaf protein (mg/g dry weight). All data in bar graph show mean±SE, n=3. Student's t-test was used to compare protein composition in the WT and AtNF-YC4-OE lines. **P<0.01.

Figure 8:
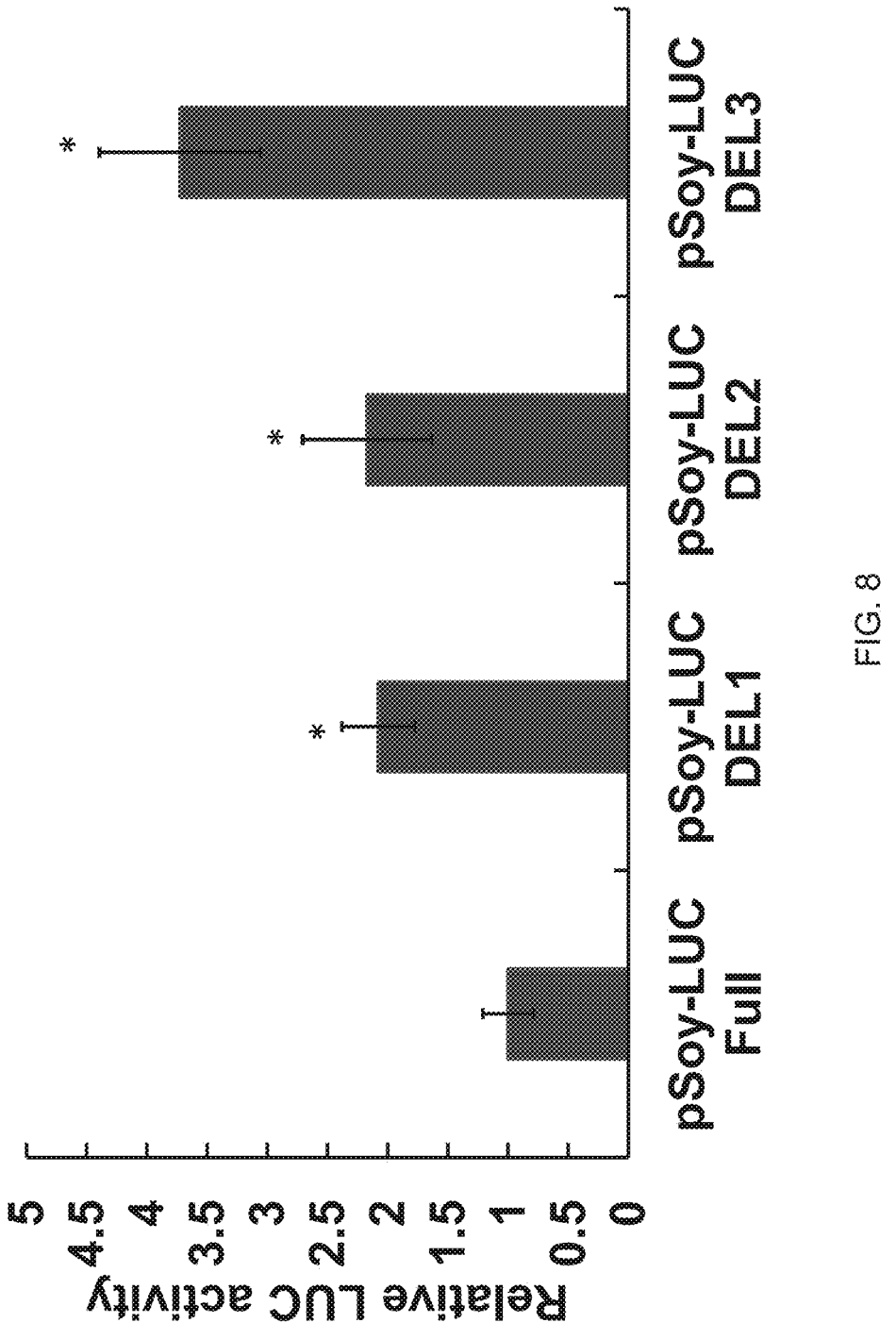

FIG. 8 is a graph of LUC (luciferase) activity from tobacco, in which the transcription repressor motif in the promoter region of soybean NF-YC4 has been deleted (pSoy-LUC DEL1, pSoy-LUC DEL2, and pSoy-LUC DEL3), vs. relative LUC activity as compared to control (pSoy-LUCFull). Data represent mean±SEM, n=3. Student's t-test was used to compare the LUC activity driven by promoters with deletions and the full-length promoter. *P<0.05. Error bars indicate the standard errors.

Figure 9:
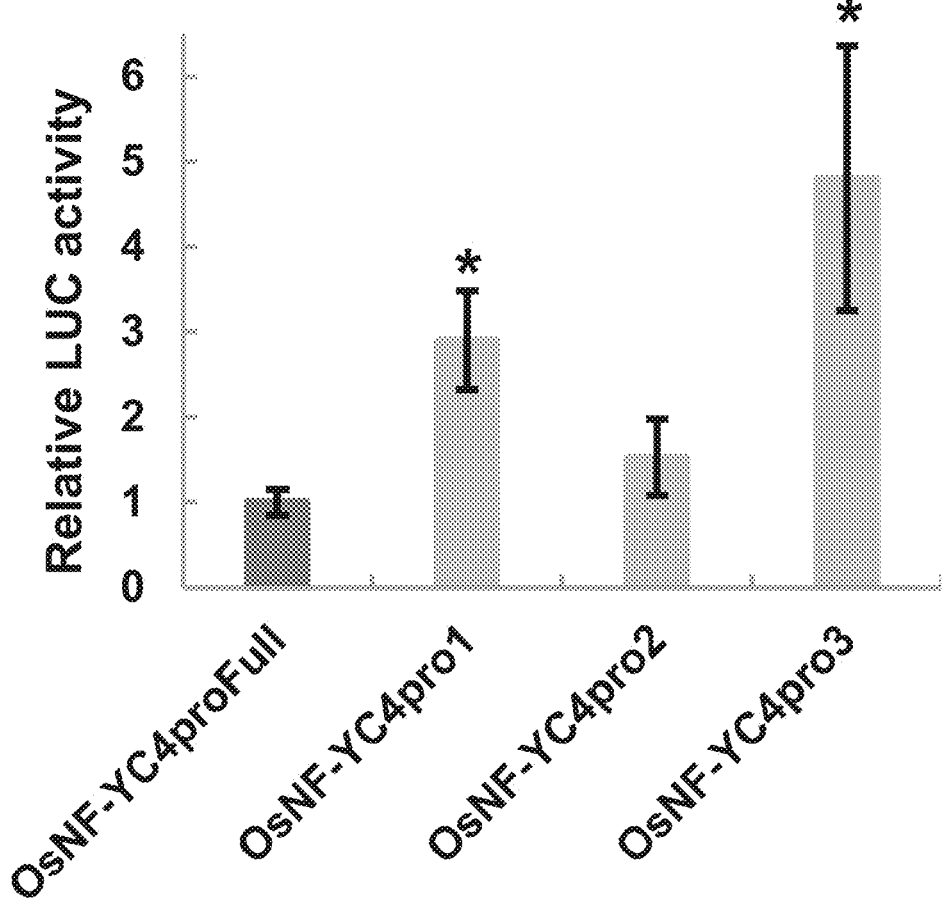

FIG. 9 is a graph of LUC activity from tobacco, in which the transcription repressor motif in the promoter region of rice NF-YC4 has been deleted (OsNF-YC4pro1, Os-NF-YC4pro2, and Os-NF-YC4pro3), vs. relative luciferase (LUC) activity as compared to control (OsNF-YC4proFull). Data represent mean±SEM, n=3. Student's t-test was used to compare the LUC activity driven by promoters with deletions and the full-length promoter. *P<0.05. Error bars indicate the standard errors.

Figures 10A, 10B:
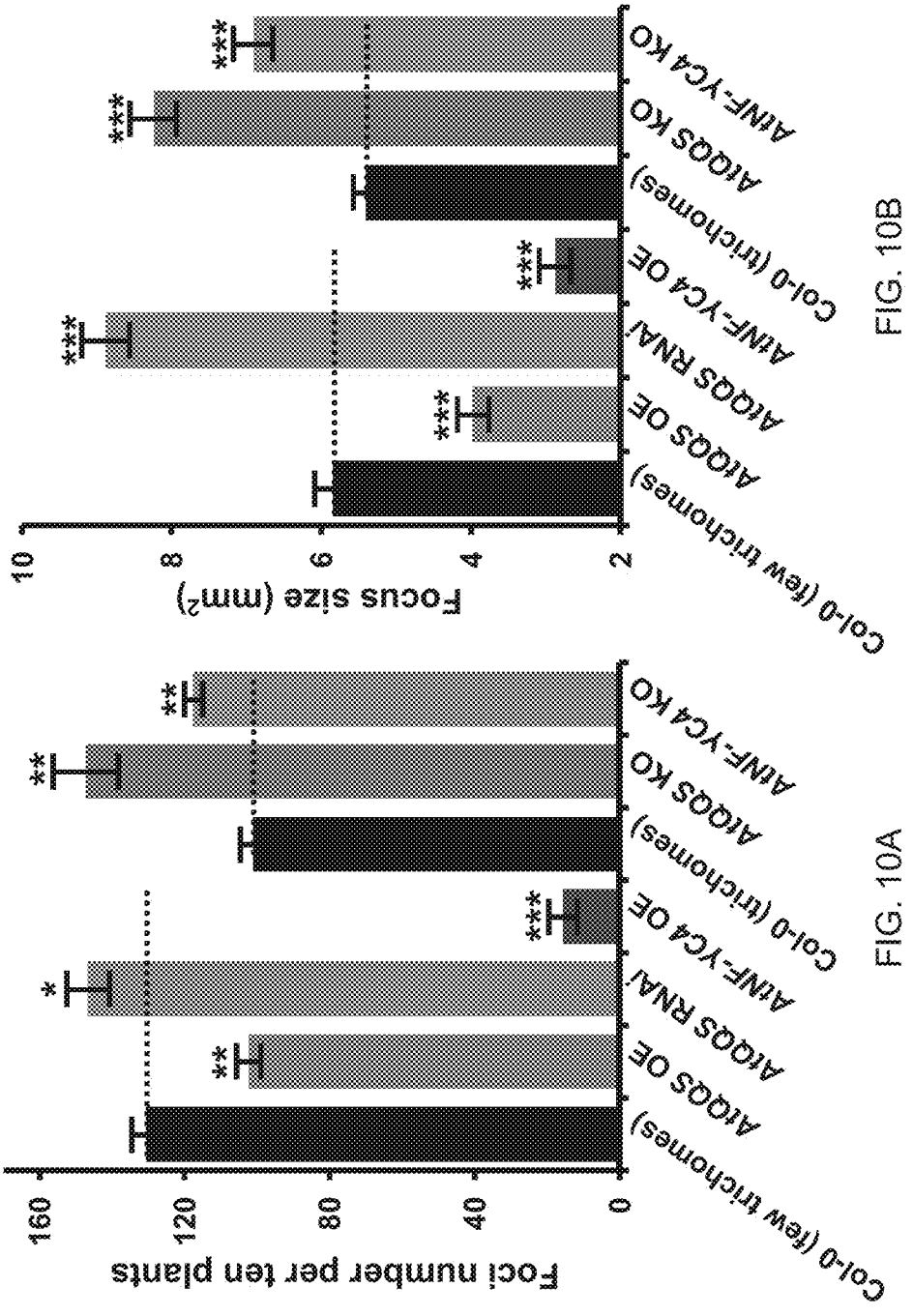

FIG. 10A is a graph of mutant vs. controls for average foci number per 10 *Arabidopsis* plants (±standard error at 120 hours after virus inoculation (hai)). Student's t-test was used to compare foci number in the control and QQS or NF-YC4 mutants. *P<0.05. P<0.01. *P<0.001.

FIG. 10B is a graph of mutant vs. controls for average focus size (mm$^2$) (±standard error at 120 hai after virus inoculation (n=40)). Student's t-test was used to compare foci number in the control and QQS or NF-YC4 mutants. ***P<0.001.

Figure 11:
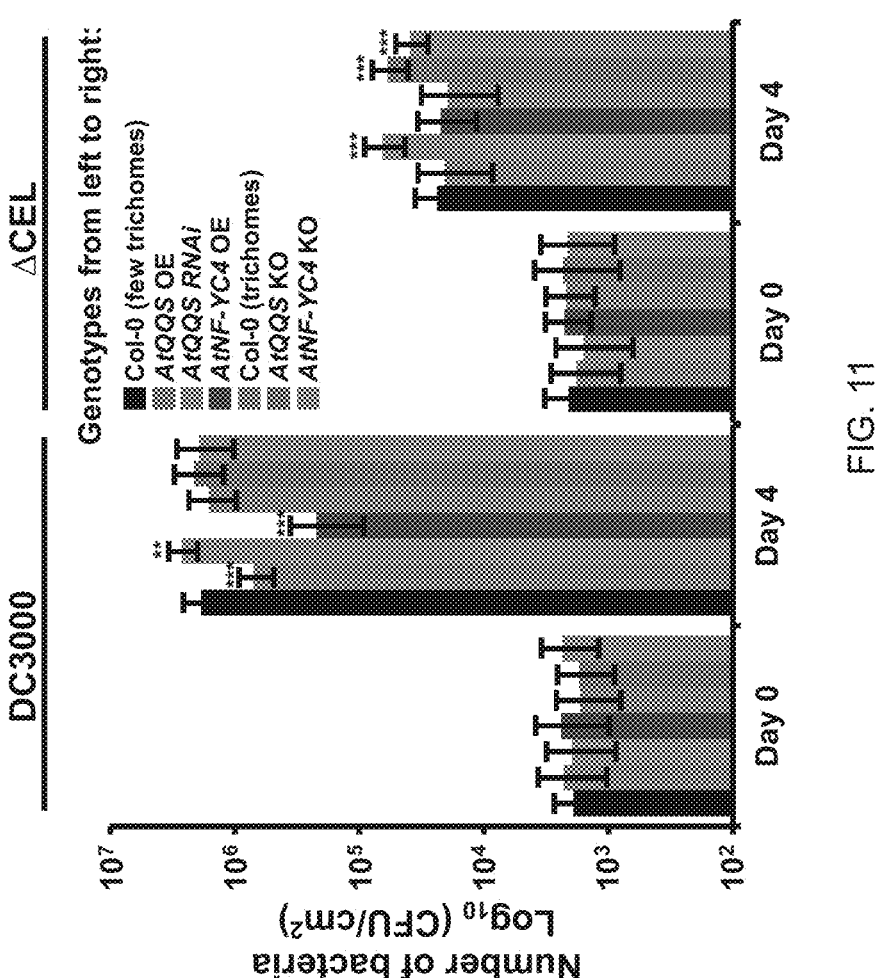

FIG. 11 is a graph of Day 0 (0 dpi) and Day 4 (4 dpi) after inoculation in *Arabidopsis* plants for Pst DC3000 and A CEL vs. number of bacteria (log$_{10}$ (CFU/cm$^2$)). Error bars indicate the standard errors. Student's t-test was used to compare bacterial number in the control and QQS or NF-YC4 mutants. P<0.01. *P<0.001.

Figures 12A, 12B:
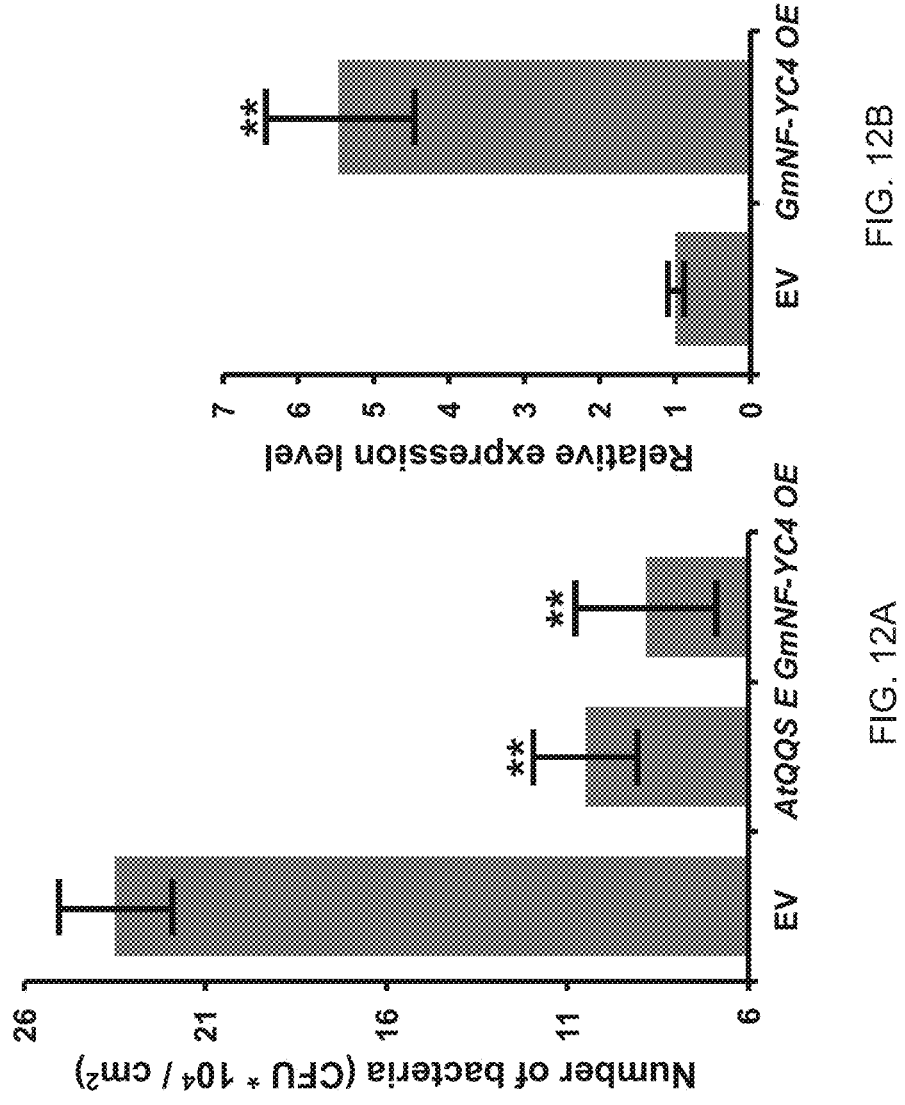

FIG. 12A is a graph of soybean line for number of bacteria (CFU*10$^4$/cm$^2$). Error bars indicate the standard errors. Student's t-test was used to compare bacterial number in the control and QQS-E or NF-YC4-OE mutants. **P<0.01. (EV=empty vector)

FIG. 12B is a graph of NF-YC4-OE soybean line for relative expression level. Error bars indicate the standard errors. **P<0.01. (EV=empty vector)

Figure 13:
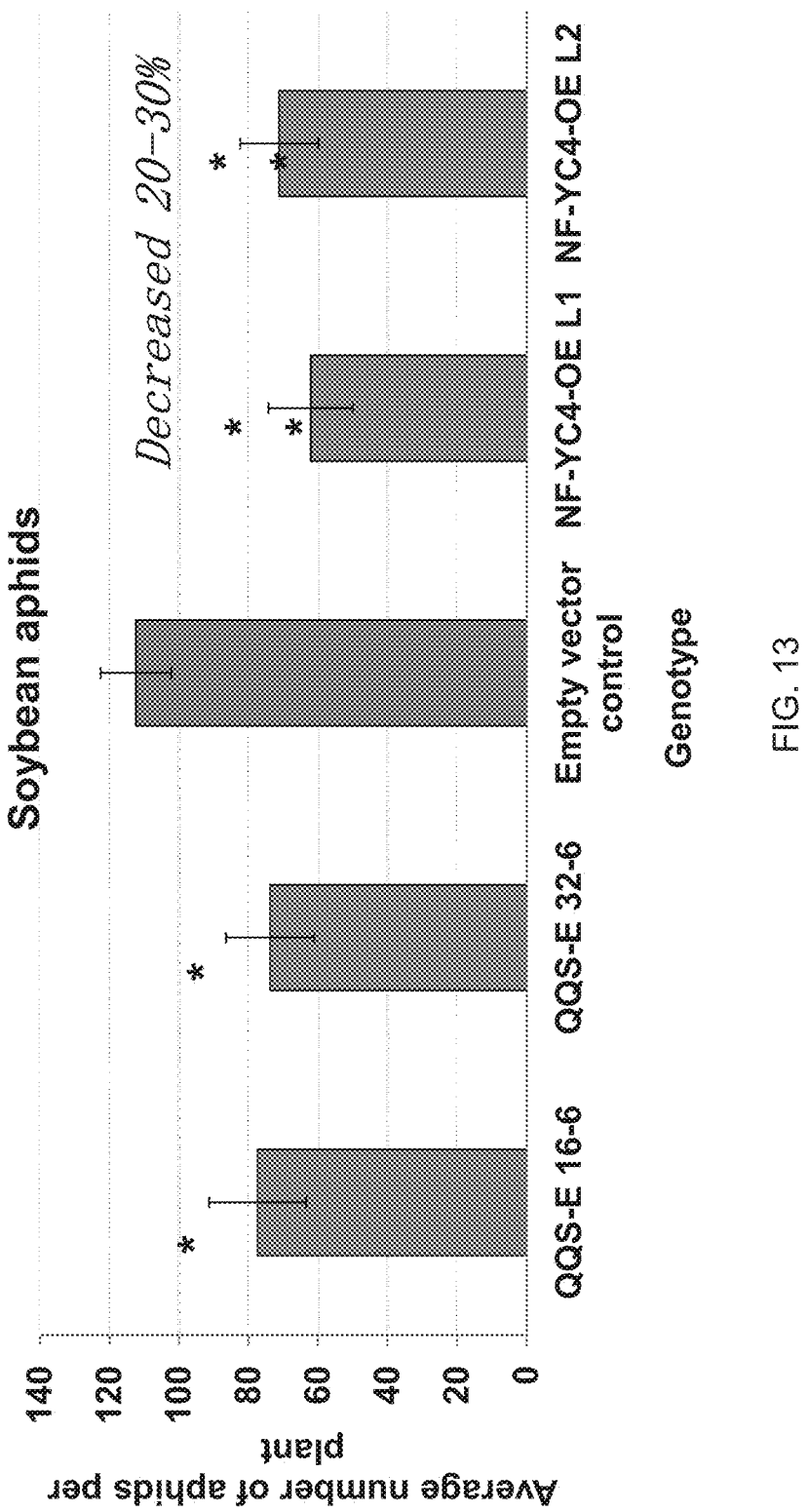

FIG. 13 is a graph of soybean genotype QQS-E 16-6 (QQS-expressing line 16-6), QQS-E 32-6 (QQS-expressing line 32-6), control, NF-YC4-OE L1 (NF-YC4 overexpressing line 1), and NF-YC4-OE L2 (NF-YC4 overexpressing line 2) vs. average number of aphids per plant. Errors bars indicate the standard errors. Student's t-test was used to compare aphid number in the control and QQS-E or NF-YC4-OE mutants. *P<0.05. **P<0.01. (EV=empty vector)

Figures 14A, 14B, 14C:
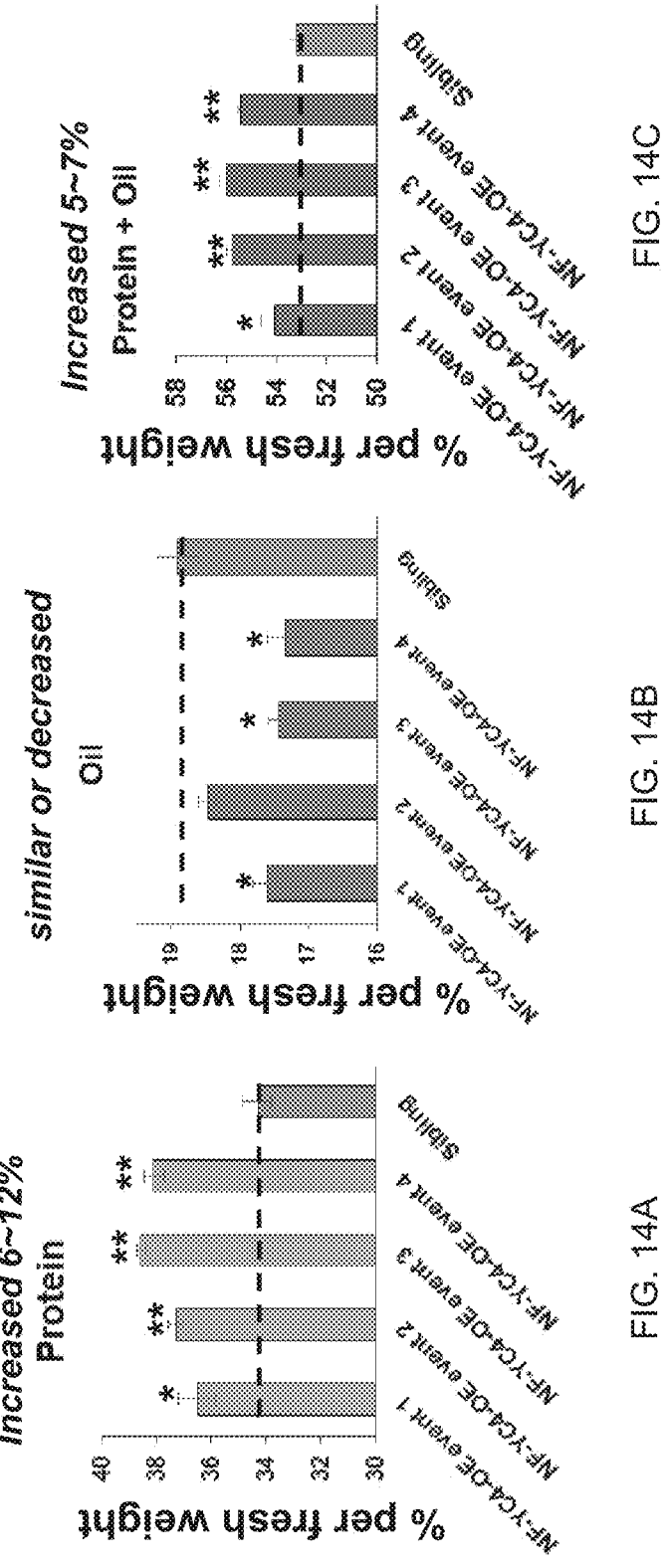

FIG. 14A is a graph of transformation event (1, 2, 3 and 4; each number indicates a different transformation event) of transformed soybean overexpressing NF-YC4 (NF-YC4-OE) vs. protein content as compared to sibling control. Error bars indicate the standard errors. Student's t-test was used to compare protein content in the NF-YC4-OE mutants and sibling controls. *P<0.05. **P<0.01.

FIG. 14B is a graph of transformation event (1, 2, 3 and 4; each number indicates a different transformation event) of transformed soybean overexpressing NF-YC4 (NF-YC4-OE) vs. oil content as compared to sibling control. Error bars indicate the standard errors. Student's t-test was used to compare oil content in the NF-YC4-OE mutants and sibling controls. *P<0.05.

FIG. 14C is a graph of transformation event (1, 2, 3 and 4; each number indicates a different transformation event) of transformed soybean overexpressing NF-YC4 (NF-YC4-OE) vs. protein+oil content as compared to sibling control. Error bars indicate the standard errors. Student's t-test was used to compare protein+oil content in the NF-YC4-OE mutants and sibling controls. *P<0.05. **P<0.01.

FIG. 14D is a graph of transformation event (1, 2, 3 and 4; each number indicates a different transformation event) of transformed soybean overexpressing NF-YC4 (NF-YC4-OE) vs. seed fiber (% per fresh weight with 13% moisture) as compared to sibling control. Error bars indicate the standard errors. Student's t-test was used to compare fiber content in the NF-YC4-OE mutants and sibling controls. **P<0.01.

FIG. 14E a graph of transformation event (1, 2, 3 and 4; each number indicates a different transformation event) of transformed soybean overexpressing NF-YC4 (NF-YC4-OE) vs. seed weight per plant (grams per plant) as compared to sibling control. Error bars indicate the standard errors. Student's t-test was used to compare seed weight per plant in the NF-YC4-OE mutants and sibling controls.

Figures 15A, 15B, 15C:
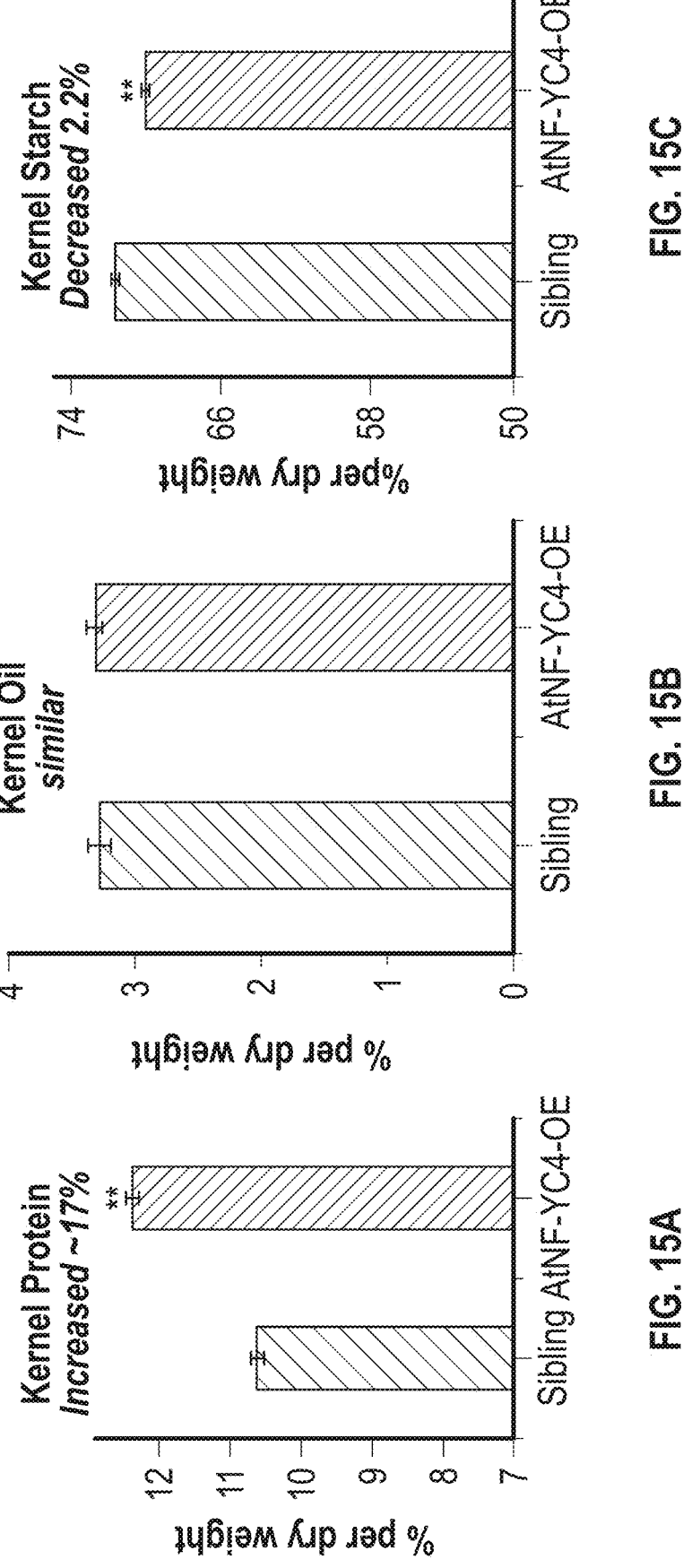

FIG. 15A is a graph of transformed corn overexpressing *Arabidopsis* NF-YC4 (AtNF-YC4-OE) vs. kernel protein (% per dry weight) as compared to sibling control. Error bars indicate the standard errors. Student's t-test was used to compare protein content in the NF-YC4-OE mutants and sibling controls. **P<0.01.

FIG. 15B is a graph of transformed corn overexpressing *Arabidopsis* NF-YC4 (AtNF-YC4-OE) vs. kernel oil (% per dry weight) as compared to sibling control. Error bars indicate the standard errors. Student's t-test was used to compare oil content in the NF-YC4-OE mutants and sibling controls.

FIG. 15C is a graph of transformed corn overexpressing *Arabidopsis* NF-YC4 (AtNF-YC4-OE) vs. kernel starch (% per dry weight) as compared to sibling control. Error bars indicate the standard errors. Student's t-test was used to compare starch content in the NF-YC4-OE mutants and sibling controls. **P<0.01.

Figures 16A, 16B:
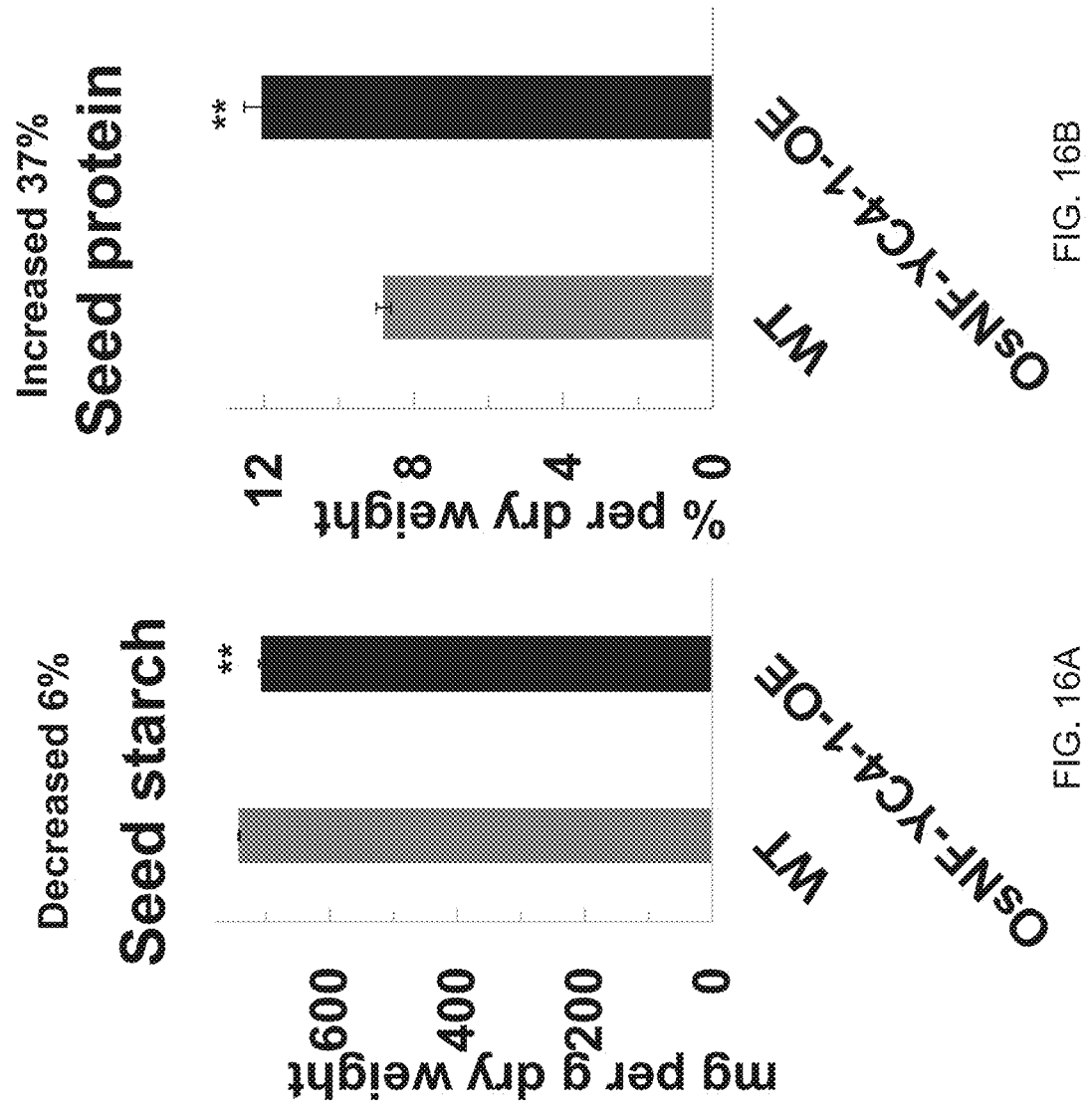

FIG. 16A is a graph of transformed rice overexpressing rice NF-YC4 (OsNF-YC4-1-OE) vs. seed starch (mg per g dry weight) as compared to wild-type. Error bars indicate the standard errors. Student's t-test was used to compare seed starch content in the NF-YC4-OE mutants and controls. **P<0.01.

FIG. 16B is a graph of transformed rice overexpressing rice NF-YC4 (OsNF-YC4-1-OE) vs. seed protein (mg per g dry weight) as compared to wild-type. Error bars indicate the standard errors. Student's t-test was used to compare seed protein content in the NF-YC4-OE mutants and controls. **P<0.01.

DETAILED DESCRIPTION

The present disclosure is based, at least in part, on the discovery of a gene with which QQS interacts. The gene is a transcriptional regulator known as NF-YC4. The gene is conserved across eukaryotic species, being present in diverse plant species from *Arabidopsis* to staple crop species, e.g., soybean, rice, and corn. Over-expression of NF-YC4 in *Arabidopsis* mimics QQS over-expression; protein content is increased and carbohydrate content is decreased. Thus, the present disclosure provides materials and methods for manipulating a gene, such as NF-YC, in particular NF-YC4 (aliases include, but are not limited to, MLE2.10, MLE2_10, and nuclear factor Y, subunit C), that interacts with QQS (referred to herein as "interactor genes"). In embodiments, the manipulation of the gene results in increased protein content and/or decreased carbohydrate content and/or increased resistance to a pathogen or a pest. The manipulation of the gene can involve mutation, such as by a deletion (or an insertion, a substitution, an inversion, and the like), of a transcriptional repressor binding site comprising a transcriptional repressor binding motif (or more than one site/motif, if more than one is present, in which case they can be mutated in the same manner or in different manners). The transcriptional repressor binding site can be manipulated, such as by mutation, e.g., by a deletion, of one or more transcriptional repressor binding motifs present therein. "Modification," "modify," "modifying," and "modified" may be used herein to describe such manipulations.

NF-YC is part of the NF-Y transcription factor complex. NF-Y is comprised of three subunits, namely NF-YA, NF-YB, and NF-YC. Each of the three subunits comprises a region that has been evolutionarily conserved. The conserved region is at the C-terminus of the NF-YA subunit, at the N-terminus of the NF-YC subunit, and centrally located in the NF-YB subunit. The NF-YA and NF-YC subunits have glutamine-rich regions, which contain an activation domain function and show some degree of conservation. NF-Y has been shown to contain two transcription activation domains—one in the NF-YA subunit and another in the NF-YC subunit. A histone-fold motif (HFM) of about 65 amino acids in length is present in the NF-YB and the NF-YC subunits. The NF-YB and NF-YC subunits form a tight dimer, which then associates with the NF-YA subunit. The resulting trimer can bind to DNA.

Plant transcription factors include a superfamily referred to as AP2/ERF. The AP2/ERF superfamily is defined by the AP2/ERF domain, which consists of about 60-70 amino acids and is involved in DNA binding. The superfamily comprises three families—the AP2 family, the ERF family, and the RAV family. The AP2 family of proteins contains two repeated AP2/ERF domains, the ERF family of proteins contains a single AP2/ERF domain, and the RAV family of proteins contains a single AP2/ERF domain and a B3 domain, which is a DNA-binding domain that is conserved in other plant-specific transcription factors. Additional information is available from the Plant Transcription Factor Database (Plant TFDB) website.

An example of a transcriptional repressor binding motif found in the promoter region of NF-YC4 is one that is bound by RAV1. A sequence of a RAV1 motif is CAACA. RAV1 binds as a monomer to a bipartite target consisting of a motif having a CAACA and a motif having a CACCTG. The two motifs can be separated by 2-8 nucleotides and can be oriented differently relative to each other (Kagaya et al., Nucleic Acids Res. 27: 470-478 (1999)). As indicated above, RAV1 is a single AP2/ERF and B3 domain-containing transcription factor. Aliases include, but are not limited to, At1g13260, EDF4, ethylene response DNA binding factor 4, ethylene-responsive transcription factor RAV1, protein related to ABI3/VP1 1, related to ABI3/VP1 1, T6J4_2, and T6J4.2. Additional information is available from the iHOP (information hyperlinked over proteins) website and the Plant TFDB website. RAV1 has the following designations: UniProt Q9ZWM9, PDB structure 1WID, NCBI Gene 837886, NCBI RefSeq NP_172784, NCBI RefSeq NM_101197, NCBI UniGene 837886, NCBI Accession Nos. BAA34250 and AAG09554. Homologues of RAV1 include AT3G25730 (*Arabidopsis thaliana*), TEM1 (*Arabidopsis thaliana*), RAV2 (*Arabidopsis thaliana*), Os01g0693400 (*Orzya sativa* Japonica Group), and Os05g0549800 (*Orzya sativa* Japonica Group). All of the preceding sequence/structural information available from UniProt, PDB, and NCBI is hereby specifically incorporated by reference.

Another example of a transcriptional repressor binding motif found in the promoter region of NF-YC4 is one that is bound by ERF (ethylene response factor), more specifically a "W box" motif (e.g., found in promoter of ERF3 gene, for example; may be referred to herein as ERF motif). A sequence of a W box motif is TGACY, wherein Y=C or T). As indicated above, ERF is a single AP2/ERF domain-containing transcription factor. Additional information is available from the Plant TFDB website. For a discussion of the genome-wide analysis of the ERF gene family in *Arabidopsis* and rice, see Nakano et al., Plant Physiol. 140(2): 411-432 (2006), which is hereby incorporated by reference for its teachings regarding same.

Thus, in view of the above, the present disclosure provides a method of increasing protein content in a eukaryotic cell comprising an NF-YC4 gene. The NF-YC4 gene comprises a promoter comprising a transcriptional repressor binding site. A method of producing a plant with increased protein content is also provided. Further provided is a method of increasing resistance to stress, such as an abiotic stress (e.g., salt, drought, pollution) or a biotic stress, such as a pathogen or a pest, in a plant cell or a plant, in particular a plant at risk of infection with a pathogen or a pest. The plant comprises an NF-YC4 gene, which comprises a promoter comprising a transcriptional repressor binding site. Still further provided is a method of producing a plant with increased resistance to a pathogen or a pest.

The above methods comprise manipulating or modifying the transcriptional repressor binding site, whereupon the transcriptional repressor cannot prevent transcription of the NF-YC4. The transcriptional repressor binding site can comprise, consist essentially of, or consist of an ERF motif and/or a RAV1 motif, either one or both of which can be manipulated or modified, such as deleted, such as deleted by using TALENS or CRISPR/Cas9. When two or more motifs are manipulated or modified, they can be manipulated or modified in the same manner or differently. The method does not encompass the replacement of the entire promoter with another promoter, such as a constitutive promoter.

The NF-YC4 gene can be any eukaryotic NF-YC4 gene, such as an NF-YC4 gene from an animal, an NF-YC4 gene from a fungus, an NF-YC4 gene from an alga, or an NF-YC4 gene from a plant. Examples of NF-YC4 genes include, but are not limited to, those present in *Brassica napus* (CDS is available as GenBank Accession No. KC797143.1), *Medicago truncatula* (CDS is available as GenBank Accession No. JQ918296.1), *Arabidopsis thaliana* (Gene ID 836466; TAIR AT5G63470 (AT5G63470.1 and AT5G63470.2); genomic sequence is available as NC_003076.8 (25415701.25417117, complement), CDS is available as GenBank Accession Nos. NM_125742.5 and NM_001037053.1)), *Glycine max* (Glyma06g17780 and Glyma04g37291), *Oryza sativa* (Os3g14669, Os02g07450, and Os06g45640), and *Zea mays* (GrmZm2g089812). Another gene also has been identified in *Chlamydomonas reinhardtii* (Cre12.g556400; Cre12.g556400.t1.3). In an embodiment of the method, the coding region of the NF-YC4 gene is not manipulated or modified. In another embodiment of the method, the coding region of the NF- YC4 gene is manipulated or modified, such as manipulated or modified (e.g., insertion, deletion, substitution, inversion, or truncation at N- or C-terminus) to increase further protein content.

Other NF-YC4 genes (including homologs, orthologs, and paralogs) can be identified by methods known in the art. For example, genes can be identified by searching databases for conserved domains that share amino acid sequence identity with the NF-YC4 genes identified herein. The degeneracy of the genetic code allows highly variable nucleotide sequences to be translated into proteins having highly similar, and even identical, amino acid sequences. Programs, such as MEGALIGN (DNAStar, Inc., Madison, WI), can create alignments between two or more sequences according to different methods, e.g., clustal analysis (Higgin et al., Gene 73: 237-244 (1988)). Other alignment algorithms and programs include FASTA, BLAST, and ENTREZ (NCBI; Altschul et al., J. Mol. Evol. 36: 290-300 (1993); Altschul et al., J. Mol. Biol. 215: 403-410 (1990)). Sec, also, the GCG program (U.S. Pat. No. 6,262,333) and other techniques for alignment described by Doolittle, Methods in Enzymology 266, "Computer Methods for Macromolecular Sequence Analysis," Academic Press, Inc., San Diego, CA (1996). The Smith-Waterman algorithm permits gaps in sequence alignments; the algorithm can be carried out using a MASPAR computer and MPSRCH software. The GAP program using the Needleman and Wunsch alignment method also can be used to align sequences. Additionally or alternatively, transcript profiles upon overexpression or knockout of two or more related transcription factors can be compared. Manual methods also can be used to identify regions of similarity and conserved domains and can involve comparison of tertiary structure. Once identified, such genes can be cloned in accordance with methods known in the art.

Other NF-YC4 genes also can be identified by hybridization under stringent or highly stringent conditions. Stringency is influenced by a variety of factors, such as temperature, salt concentration and composition, organic and nonorganic additives, solvents, etc. in the hybridization and wash solutions (sec, e.g., Sambrook et al., supra; Nucleic Acid Hybridization: A Practical Approach, Hames and Higgins, eds., IRL Press, Washington, DC (1985)). Hybridization assays, such as Southern blot, Northern blot, solution hybridization, and the like can be used (see, e.g., Sambrook et al., supra).

With respect to sequences described herein, the percentage of sequence identify can range from about 55% to 100%. Given that the NF-YC4 gene is highly conserved across a wide range of eukaryotes, the percentage of sequence identity, particularly at the amino acid level, can range from about 60% to 100%, such as about 65% to 100%, about 70% to 100%, about 75% to 100%, about 80% to 100%, about 85% to 100%, about 90% to 100%, or about 95% to 100%, such as about 96%, about 97%, about 98% or about 99%.

The region of NF-YC4 to be manipulated or modified is the promoter region. More specifically, a transcriptional repressor binding site to which a transcriptional repressor binds is manipulated or modified, such as by mutation, specifically deletion (or insertion, substitution, inversion, or the like), to prevent or inhibit binding of a transcriptional repressor to the binding site, thereby modifying the biochemical composition of a eukaryote, such as a plant. In particular, a transcriptional repressor binding site motif is manipulated or modified. For example, the composition of storage products, such as proteins, carbohydrates, and lipids can be modified. More specifically, protein content can be increased and/or carbohydrate content can be decreased.

The promoter region of the NF-YC4 gene of *Oryza sativa* (Os03g14669) is shown as SEQ ID NO: 1 (see FIG. 2A). A RAV1 motif (reverse) is shown in bold, whereas a RAV1 (reverse) and ERF (forward) motif is shown in underlined bold, and ERF motifs (reverse) are shown in italicized bold.

A promoter region of the NF-YC4 gene of *Oryza sativa* in which a RAV1 (reverse) motif (TGTTG; see bold in SEQ ID NO: 1) has been deleted is shown as SEQ ID NO: 2 (sec FIG. 2A). A RAV1 (reverse) and ERF (forward) motif is shown in underlined bold, whereas ERF motifs (reverse) are shown in italicized bold.

A promoter region of the NF-YC4 gene of *Oryza sativa* in which overlapping sequences of a RAV1 (reverse) motif and an ERF (forward) motif (TGTTGACT; see underlined bold in SEQ ID NO: 1) have been deleted is shown as SEQ ID NO: 3 (see FIG. 2B). A RAV1 motif (reverse) is shown in bold, whereas ERF motifs (reverse) are shown in italicized bold.

A promoter region of the NF-YC4 gene of *Oryza sativa* in which a 111 bp segment containing two ERF motifs (reverse) (AGTCATCACTGTTCTATGTTCTATCTGCATT TTCCTTGATTTTGTACTTTTCCT-GAACGAAAGGACAATCCTTAGCCATCATAATGC TATGATCGACTTATTCTGAAGTCA [SEQ ID NO: 5; see two ERFs in bold italics in SEQ ID NO: 1 and intervening sequence) has been deleted is shown as SEQ ID NO: 4 (see FIG. 2B). A RAV1 motif (reverse) is shown in bold, and a RAV1 (reverse) and ERF (forward) motif is shown in underlined bold.

A promoter region of the NF-YC4 gene of *Oryza sativa* in which a 190 bp segment containing two ERF motifs (reverse), a RAV1 (reverse) and ERF (forward) motif, and intervening sequences (AACGAAAACAGCT TGTTGACT GGCTCCCTAGAGCTTTTT GTAAGTTGAT-CATCGAAGTAGCTAGTTCTCTTCACTTATCAGTCAT-CACTGTTCTA TGTTCTATCTGCATTTTCCTTGAT-TTTGTACTTTTCCTGAACGAAAGGACAATCCT TAGCCATCATAATGCTATGATCGACTTATTCT-GAAGTCA [SEQ ID NO: 7]; see two ERF motifs (reverse) in italicized bold, RAV1 (reverse) and ERF (forward) motif in underlined bold, and intervening sequences in SEQ ID NO: 1) have been deleted is shown as SEQ ID NO: 6 (see FIG. 2C). A RAV1 motif (reverse) is shown in bold.

In embodiments of the methods involving a rice cell or a rice plant, (i) two ERF motifs can be deleted, (ii) a RAF1 motif can be deleted, or (iii) a RAV1 motif and an ERF motif can be deleted.

The promoter region of the NF-YC4 gene of *Glycine max* (Glyma06g17780) is shown as SEQ ID NO: 8 (see FIG. 2C). ERF motifs (reverse) are shown in italicized bold, RAV1 motifs (reverse) are shown in bold, and a RAV1 motif (forward) is shown in underlined bold.

A promoter region of the NF-YC4 gene of *Glycine max* in which an ERF motif (reverse), a RAV1 motif (forward), and the intervening sequence (AGTCACATGCCA CAACA [SEQ ID NO: 10]; see italicized bold and underlined bold in SEQ ID NO: 8) have been deleted is shown as SEQ ID NO: 9 (see FIG. 2D). An ERF motif (reverse) is shown in italicized bold, and RAV1 motifs (reverse) are shown in bold.

A promoter region of the NF-YC4 gene of *Glycine max* in which an ERF motif (reverse), a RAV1 motif (reverse), and the intervening sequence (GGTCAGTTTTTGTT AACAT-TAATTTTTAGGATTATT TGTTG [SEQ ID NO: 12]; see italicized bold and bold in SEQ ID NO: 8) have been deleted is shown as SEQ ID NO: 11 (see FIG. 2D). An ERF motif (reverse) is shown in italicized bold, RAV1 motifs (reverse) are shown in bold, and a RAV1 motif (forward) is shown in underlined bold.

A promoter region of the NF-YC4 gene of *Glycine max* in which two RAV1 motifs and the intervening sequence (TGTTG GTAATGTAAAAAAAATTAAAAGAAACAAGAT-TAAATTACGTATTTAATAATTTAAGATTAA TGTTG [SEQ ID NO: 14]; see bold in SEQ ID NO: 8) have been deleted is shown as SEQ ID NO: 13 (see FIG. 2E). ERF motifs (reverse) are shown in italicized bold, a RAV1 motif (reverse) is shown in bold, and a RAV1 motif (forward) is shown in underlined bold.

In embodiments of the methods involving a soybean cell or a soybean plant, (i) two RAV1 motifs can be deleted or (ii) a RAV1 motif and an ERF motif can be deleted.

The promoter region of the NF-YC4 gene of *Zea mays* is shown as SEQ ID NO: 20. Two RAV1 motifs (forward) are shown in bold. In embodiments of the methods involving a corn cell or a corn plant, either one or both RAV1 motifs can be deleted.

The region can be modified by any suitable methodology known in the art. For example, site-directed or site-specific mutagenesis, optimized directed evolution, gene site-saturation mutagenesis (GSSM), synthetic ligation reassembly (SLR), error-prone PCR, shuffling, oligonucleotide-directed mutagenesis, assembly PCR, sexual PCR mutagenesis, in vivo mutagenesis, cassette mutagenesis, recursive ensemble mutagenesis, exponential ensemble mutagenesis, gene reassembly, SLR recombination, recursive sequence recombination, phosphorothioate-modified DNA mutagenesis, uracil-containing template mutagenesis, gapped duplex mutagenesis, point mismatch repair mutagenesis, repair-deficient host strain mutagenesis, chemical mutagenesis, radiogenic mutagenesis, deletion mutagenesis, restriction-selection mutagenesis, restriction-purification mutagenesis, artificial gene synthesis, ensemble mutagenesis, chimeric nucleic acid multimer creation, or other targeted mutagenesis techniques, such as genomic engineering with meganucleases, transposons, recombinases, chemical DNA cutters, and programmable nucleases like zinc-finger nucleases (ZFNs), transcription activator-like effector nucleases (TALENs), RNA-guided, engineered nucleases (RGENs), and the bacterial, type II clustered regularly interspaced short palindromic repeat (CRISPR)-Cas (CRISPR-associated) adaptive immune system. Genomic engineering with ZFNs (zinc-finger protein (ZFP) at amino terminus and Fok I or other nuclease domain at carboxyl terminus), TALENs (transcription activator-like effector (TALE) at amino terminus and Fok I or other nuclease domain at carboxyl terminus), RGENs, and the CRISPR-Cas system enable targeted genetic modifications in cultured cells, plants, and animals by cleaving chromosomal DNA in a site-specific manner, which triggers endogenous DNA repair systems that result in targeted genomic modification. For a review, see Kim et al., Nature Reviews (Genetics) 15: 321-334 (May 2014), which is hereby incorporated by reference for its teachings regarding same. See, also, references 178-180 cited therein (and incorporated by reference) for the use of engineered nucleases to improve genetically crops and references 32 and 168 cited therein (and incorporated by reference) for the use of engineered nucleases to enrich livestock with certain nutrients or render them disease-resistant.

Off-target effects of RGENs and other nucleases can be minimized or avoided. For example, choosing a unique target site that lacks highly homologous sequences elsewhere in the genome is important. Such sites can be identified by searching using a computer algorithm for TALENs.

In addition, web-based programs are available for TALENs and RGENs as mentioned herein below. Also important is optimizing nuclease expression levels for RGENs. The use of either modified guide RNAs with two additional guanines at the 5' terminus or truncated sgRNAs reduces off-target mutations. The use of recombinant proteins over plasmids to introduce programmable nucleases reduces off-target mutations due to rapid degradation of the recombinant proteins in the cells. Finally, DNA-nicking enzymes ("nickases") that introduce single-strand breaks into DNA can minimize off-target mutations.

In an embodiment, TALENs are used (see, for example, U.S. Pat. App. Pub. No. 2011/0201118, which is hereby incorporated by reference in its entirety, particularly page 50, line 14, through page 58, line 4, page 64, line 2, through page 66, line 29, and FIGS. 1-3 and 10-16; see, also, U.S. Pat. No. 8,586,363, which is hereby incorporated by reference in its entirety; see, also, U.S. Pat. App. Pub. No. 2014/335618, which is hereby incorporated by reference in its entirety; see, also, U.S. Pat. App. Pub. No. 2014/335592, which is hereby incorporated by reference in its entirety; see, also, U.S. Pat. App. No. 2013/0122581 and U.S. Pat. No. 8,697,853, both of which are hereby incorporated by reference in their entireties; see, also, U.S. Pat. App. Pub. No. 2012/214228 and U.S. Pat. No. 8,450,471, both of which are hereby incorporated by reference in their entireties; see, also, U.S. Pat. App. Pub. No. 2012/178169 and U.S. Pat. No. 8,440,432, both of which are hereby incorporated by reference in their entireties; see, also, U.S. Pat. App. Pub. No. 2012/178131 and U.S. Pat. No. 8,440,431, both of which are hereby incorporated by reference in their entireties; see, also, U.S. Pat. App. Pub. No. 2011/0301073 and U.S. Pat. No. 8,586,526, both of which are hereby incorporated by reference in their entireties; U.S. Pat. App. Pub. No. 2014/087426, which is hereby incorporated by reference in its entirety; see, also, U.S. Pat. App. Pub. No. 2014/0073015, and U.S. Pat. No. 8,748,134, both of which are hereby incorporated by reference in their entireties). Since TALENs can be designed to target almost any given DNA sequence, TALENs offer a crucial advantage over other types of nucleases, although choosing a target sequence with a thymine at the 5' end is recommended as is either avoiding a target sequence with a methylated cytosine or replacing the His-Asp RVD repeat, which recognizes cytosines, with an Asn-Gly RVD repeat, which recognizes thymine and will recognize a methylated cytosine. The TAL effector can be any suitable TAL effector. For example, a naturally occurring TAL effector (i.e., a wild-type TAL effector or a naturally occurring mutant TAL effector) or a man-made TAL effector (e.g., a mutated, naturally occurring TAL effector or a synthetic TAL effector) can be used. An example of a TAL effector is AvrXa7 from the *Xanthomonas* spp. bacteria or *Ralstonia* spp. bacteria (see, for example, Int'l Pat. App. Pub. No. WO 2013/101877, which is hereby incorporated by reference in its entirety). The endonuclease cleaves both strands of DNA and allows for modification of the DNA sequence at the site of cleavage. The size of the construct is ~3 kb×2. The specificity-determining length of the target site is from about 30 bp to about 40 bp. Desirably, the target site starts with a thymine and ends with an adenine. Online resources, such as E-TALEN, Genome engineering resources, Scoring algorithm for predicting TALE(N) activity, ToolGen TALEN Designer, and ZiFiT Targeter software can be used to design TALENs; see, also, Addgene and TALEN library resource. TALENs can be obtained from commercial suppliers, such as Cellectis Bioresearch, Life Technologies, ToolGen, and Transposagen Biopharmaceuticals.

Thus, in an embodiment, the present disclosure provides a method of increasing protein content in a eukaryotic cell comprising an NF-YC4 gene, which comprises a promoter comprising a transcriptional repressor binding site. The method comprises modifying the transcriptional repressor binding site in the NF-YC4 gene so that the transcriptional repressor cannot prevent transcription of the NF-YC4 gene. The method comprises introducing a first transcription activator-like (TAL) effector endonuclease monomer and a second TAL effector endonuclease monomer into the cell. The monomers can be introduced into the cell by any suitable method, such as by transfecting the cell with a nucleic acid encoding the first or second monomer and/or mechanically injecting the first or second monomer into the cell as a protein. When delivered as a protein, use can be made of the bacterial type III secretion system or electroporation. Each TAL effector endonuclease monomer comprises an endonuclease domain, such as a non-specific endonuclease domain, e.g., a Fok I endonuclease domain, and a TAL effector domain comprising a plurality of TAL effector repeat sequences. The plurality of TAL effector repeat sequences (e.g., 15 or more DNA binding repeats, such as DNA binding repeats, each of which comprises a repeat variable-di-residue (RVD) that determines recognition of a base pair in the NF-YC4 promoter region and is responsible for recognizing one base pair in the NF-YC4 promoter region) of the first TAL effector endonuclease monomer, in combination, bind to a first specific nucleotide sequence in the promoter region of the NF-YC4 gene. The plurality of TAL effector repeat sequences (e.g., 15 or more DNA binding repeats, such as DNA binding repeats, each of which comprises a RVD that determines recognition of a base pair in the NF-YC4 promoter region and is responsible for recognizing one base pair in the NF-YC4 promoter region) of the second TAL effector endonuclease monomer, in combination, bind to a second specific nucleotide sequence in the promoter region of the NF-YC4 gene. The first specific nucleotide sequence and the second specific nucleotide sequence are different and are separated by a spacer sequence, such as a spacer sequence that is about 12 to 30 nucleotides in length, e.g., 18 nucleotides. The first specific nucleotide sequence and the second specific nucleotide sequence are selected to achieve modification, such as by deletion, of a transcription repressor binding site in the promoter region of the NF-YC4 gene. The transcription repressor binding site can comprise an ERF motif or a RAV1 motif; in this regard, two or more ERF motifs, two or more RAV1 motifs, or a combination of ERF and RAV1 motifs can be modified, such as by deletion. The endonuclease domain of the first TAL effector endonuclease monomer and the endonuclease domain of the second TAL effector endonuclease monomer form a dimer that cleaves the target DNA sequence within the cell or progeny thereof when the TAL effector domain of the first TAL effector endonuclease monomer is bound to the first specific nucleotide sequence and the TAL effector domain of the second TAL effector endonuclease monomer is bound to the second specific nucleotide sequence. The method can further comprise providing to the cell a nucleic acid comprising a sequence homologous to at least a portion of the target DNA sequence, such that homologous recombination occurs between the target DNA sequence and the nucleic acid. Protein content in the eukaryotic cell is increased and, thus, the method can further comprise selecting for increased protein content.

The eukaryotic cell can be part of a collection of cells, a tissue, an organ, or an organism. When a cell or a collection of cells or progeny thereof, the method can further comprise generating a genetically modified tissue, organ, or organism therefrom. The organism can be a plant, such as a crop plant, such as soybean, rice, or corn, a monocot, a dicot, an alga, such as a unicellular flagellate, such as a species of *Chlamydomonas*. In embodiments, the organism is soybean, rice, or corn. Plants can be crossed and backcrossed and selected for increased protein content in accordance with methods known in the art and described herein.

In another embodiment, the present disclosure provides a method of increasing resistance to a pathogen or pest in a plant cell comprising an NF-YC4 gene, which comprises a promoter comprising a transcriptional repressor binding site. The pathogen can be a bacterium, a virus, a fungus, or a seed plant and wherein the pest is an insect, a plasmodiophorid, a mite, or a nematode, examples of all of which are known in the art and descried herein. In embodiments, the pathogen is a bacterium or a virus, and the pest is an aphid. The method comprises modifying the transcriptional repressor binding site in the NF-YC4 gene so that the transcriptional repressor cannot prevent transcription of the NF-YC4 gene. The method comprises introducing a first transcription activator-like (TAL) effector endonuclease monomer and a second TAL effector endonuclease monomer into the cell. The monomers can be introduced into the cell by any suitable method, such as by transfecting the cell with a nucleic acid encoding the first or second monomer and/or mechanically injecting the first or second monomer into the cell as a protein. When delivered as a protein, use can be made of the bacterial type III secretion system or electroporation. Each TAL effector endonuclease monomer comprises an endonuclease domain, such as a non-specific endonuclease domain, e.g., a Fok I endonuclease domain, and a TAL effector domain comprising a plurality of TAL effector repeat sequences. The plurality of TAL effector repeat sequences (e.g., 15 or more DNA binding repeats, such as DNA binding repeats, each of which comprises a repeat variable-di-residue (RVD) that determines recognition of a base pair in the NF-YC4 promoter region and is responsible for recognizing one base pair in the NF-YC4 promoter region) of the first TAL effector endonuclease monomer, in combination, bind to a first specific nucleotide sequence in the promoter region of the NF-YC4 gene. The plurality of TAL effector repeat sequences (e.g., 15 or more DNA binding repeats, such as DNA binding repeats, each of which comprises a RVD that determines recognition of a base pair in the NF-YC4 promoter region and is responsible for recognizing one base pair in the NF-YC4 promoter region) of the second TAL effector endonuclease monomer, in combination, bind to a second specific nucleotide sequence in the promoter region of the NF-YC4 gene. The first specific nucleotide sequence and the second specific nucleotide sequence are different and are separated by a spacer sequence, such as a spacer sequence that is about 12 to 30 nucleotides in length, e.g., 18 nucleotides. The first specific nucleotide sequence and the second specific nucleotide sequence are selected to achieve modification, such as by deletion, of a transcription repressor binding site in the promoter region of the NF-YC4 gene. The transcription repressor binding site can comprise an ERF motif or a RAV1 motif; in this regard, two or more ERF motifs, two or more RAV1 motifs, or a combination of ERF and RAV1 motifs can be modified, such as by deletion. The endonuclease domain of the first TAL effector endonuclease monomer and the endonuclease domain of the second TAL effector endonuclease monomer form a dimer that cleaves the target DNA sequence within the cell or progeny thereof when the TAL effector domain of the first TAL effector endonuclease monomer is bound to the first specific nucleotide sequence and the TAL effector domain of the second TAL effector endonuclease monomer is bound to the second specific nucleotide sequence. The method can further comprise providing to the plant cell a nucleic acid comprising a sequence homologous to at least a portion of the target DNA sequence, such that homologous recombination occurs between the target DNA sequence and the nucleic acid. Resistance to a pathogen or pest in the plant cell is increased and, thus, the method can further comprise selecting for increased resistance to a pathogen or pest.

The method can further comprise introducing into the plant cell and expressing therein a polynucleotide comprising a nucleotide sequence encoding a Qua-Quine Starch (QQS) polypeptide having the amino acid sequence as set forth in SEQ ID NO: 16, wherein the nucleotide sequence is operably linked to a promoter.

The plant cell can be part of a collection of cells, a tissue, an organ, or an organism. When a cell or a collection of cells or progeny thereof, the method can further comprise generating a genetically modified tissue, organ, or plant therefrom. The plant can be a crop plant, such as soybean, rice, or corn, a monocot, or a dicot. Plants can be crossed and backcrossed and selected for increased resistance to a pathogen or pest in accordance with methods known in the art and described herein.

In another embodiment, the CRISPR-Cas system is used. Target-specific crRNA and target-independent trans-activating crRNA (tracrRNA) are complexed with CRISPR-associated protein 9 (Cas9) to form an active DNA endonuclease, i.e., dualRNA-Cas9. The endonuclease cleaves a 23-bp target DNA sequence that is composed of the 20-bp guide sequence in the crRNA and the proto-spacer adjacent motif (PAM; 5'-NGG-3' or 5'-NAG-3'). Any suitable Cas9 can be used, such as the Cas9 from *Streptococcus pyogenes*. Since CRISPR-Cas/RGENs are simple to design and prepare, CRISPR/Cas offers a crucial advantage over TALENs, although RGEN target sites are limited by the requirement for the PAM sequence, which is recognized by Cas9 (i.e., 5'-X$_{20}$NGG-3' or 5'-X$_{20}$NAG-3', where X$_{20}$ corresponds to the 20-bp crRNA sequence), and either the presence of a 5' guanine in the target sequence or the addition of one or two guanine bases at the 5' ends of the guide RNAs is recommended. The size of the construct is typically around 4.2 kb (Cas9 from *S. pyogenes*)+0.1 kb (sgRNA). The specificity-determining length of the target site is typically 22 bp (for a total length of 23 bp). Desirably, the target site ends with an NGG or NAG (i.e., PAM, as indicated above). Online resources, such as E-CRISP, Genome engineering resources, RGEN tools, and ZiFiT Targeter software can be used; see, also, Addgene. Components of the CRISPR/Cas system can be obtained from commercial suppliers, such as Life Technologies, Sigma-Aldrich, System Biosciences, ToolGen, and Transposagen Biopharmaceuticals.

Thus, in another embodiment, the present disclosure provides a method of increasing protein content in a eukaryotic cell comprising an NF-YC4 gene, which comprises a promoter comprising a transcriptional repressor binding site. The method comprises modifying the transcriptional repressor binding site in the NF-YC4 gene so that the transcriptional repressor cannot prevent transcription of the NF-YC4 gene. The method comprises introducing a dualRNA-Cas9, i.e., an active DNA endonuclease formed by the complexation of a target-specific crRNA and a target-independent trans-activating crRNA (tracrRNA) with CRISPR-associated protein 9 (Cas9), into the cell. The endonuclease cleaves a 23-bp target DNA sequence (see, e.g., SEQ ID NOs: 6 and 7 and Example 18 herein) that is composed of the 20-bp guide sequence in the crRNA and the proto-spacer adjacent motif (PAM; 5'-NGG-3' or 5'-NAG-3'). Any suitable Cas9 can be used, such as the Cas9 from *Streptococcus pyogenes*. Embryonic calli of plants can be transformed via *Agrobacterium*-mediated gene transfer. Primary transgenic lines can be screened for site-specific DNA changes and identified, and PCR genotyping can be used to identify mutants with deleted sequences. Protein content in the eukaryotic cell is increased and, thus, the method can further comprise selecting for increased protein content.

The eukaryotic cell can be part of a collection of cells, a tissue, an organ, or an organism. When a cell or a collection of cells or progeny thereof, the method can further comprise generating a genetically modified tissue, organ, or organism therefrom. The organism can be a plant, such as a crop plant, such as soybean, rice, or corn, a monocot, a dicot, or an alga, such as a unicellular flagellate, such as a species of *Chlamydomonas*. In embodiments, the organism is soybean, rice, or corn. Plants can be crossed and backcrossed and selected for increased protein content in accordance with methods known in the art and described herein.

In another embodiment, the present disclosure provides a method of increasing resistance to a pathogen or pest in a plant cell comprising an NF-YC4 gene, which comprises a promoter comprising a transcriptional repressor binding site. The pathogen can be a bacterium, a virus, a fungus, or a seed plant and wherein the pest is an insect, a plasmodiophorid, a mite, or a nematode, examples of all of which are known in the art and described herein. In embodiments, the pathogen is a bacterium or a virus, and the pest is an aphid. The method comprises modifying the transcriptional repressor binding site in the NF-YC4 gene so that the transcriptional repressor cannot prevent transcription of the NF-YC4 gene. The method comprises introducing a dualRNA-Cas9, i.e., an active DNA endonuclease formed by the complexation of a target-specific crRNA and a target-independent trans-activating crRNA (tracrRNA) with CRISPR-associated protein 9 (Cas9), into the cell. The endonuclease cleaves a 23-bp target DNA sequence that is composed of the 20-bp guide sequence in the crRNA and the proto-spacer adjacent motif (PAM; 5'-NGG-3' or 5'-NAG-3'). Any suitable Cas9 can be used, such as the Cas9 from *Streptococcus pyogenes*. Resistance to a pathogen or pest in the plant cell is increased and, thus, the method can further comprise selecting for increased resistance to a pathogen or pest.

The method can further comprise introducing into the plant cell or plant and expressing therein a polynucleotide comprising a nucleotide sequence encoding a Qua-Quine Starch (QQS) polypeptide having the amino acid sequence as set forth in SEQ ID NO: 16, wherein the nucleotide sequence is operably linked to a promoter.

The plant cell can be part of a collection of cells, a tissue, an organ, or an organism. When a cell or a collection of cells or progeny thereof, the method can further comprise generating a genetically modified tissue, organ, or plant therefrom. The plant can be a crop plant, such as soybean, rice, or corn, a monocot, or a dicot. Plants can be crossed and backcrossed and selected for increased resistance to a pathogen or pest in accordance with methods known in the art and described herein.

Programmable nucleases and/or homologous templates, such as targeting vectors or single-stranded oligodeoxynucleotides (ssODNs), are delivered into target cells using any suitable method as known in the art. Such methods include, for example, delivery of plasmid DNA, in vitro-transcribed mRNA, viral vectors, or purified proteins into cultured cells, embryos, or whole organisms. Programmable nucleases are frequently introduced into cell lines by electroporation or liposome transfection of plasmid DNA. In vitro-transcribed mRNA is frequently micro-injected into one-cell embryos. Non-integrating viral vectors, such as integrase-deficient, lentiviral vectors (IDLVs), adenoviruses, and adeno-associated viruses (AAVs) can be used in vitro and in vivo, although IDLVs can be incompatible with TALENs due to the presence of highly homologous TALE repeats, which can lead to unwanted recombination events. The use of proteins avoids unwanted incorporation of foreign DNA and obviates concerns over codon optimization and choice of promoters and, since de novo purification of Cas9 is not required to construct a new nuclease, can be convenient for RGENs.

The translocation of TAL-cleavage domain fusion proteins across a cell membrane can be facilitated by the use of peptide sequences, such as the third helix of Antennapedia (Prochiantz, Curr. Opi. Neurobiol. 6: 629-634 (1996); Derossi et al., J. Biol. Chem. 269: 10444 (1994)), or the hydrophobic domain of signal peptides, such as the signal peptide K-FGF (Lin et al., J. Biol. Chem. 270: 14255-14258 (1995)). Other peptides include an 11-amino acid peptide of the tat protein of HIV, a 20-residue peptide sequence corresponding to amino acids 84-103 of the p16 protein (Fahracus et al., Curr. Biol. 6: 84 (1996)), the VP22 translocation domain from HSV (Elliot et al., Cell 88: 223-233 (1997)), and binary toxins (Arora et al., J. Biol. Chem. 268: 3334-3341 (1993); Perelle et al., Infect. Immun. 61: 5147-5156 (1993); Stennark et al., J. Cell Biol. 113: 1025-1032 (1991); Donnelly et al., PNAS USA 90: 3530-3534 (1993); Carbonetti et al., Abstr. Ann. Mect. Am. Soc. Microbiol. 95: 295 (1995); Sebo et al., Infect. Immun. 63: 3851-3857 (1995); Klimpel et al., PNAS USA 89: 10277-10281 (1992); and Novak et al., J. Biol. Chem. 267: 17186-17193 (1992)). The peptide sequences can be fused with TAL-cleavage fusion proteins. Optionally, a linker, such as a peptide linker, can be used.

The method of increasing resistance to a pathogen or a pest in a plant cell or a plant at risk of infection with the pathogen or pest can further comprise introducing into the plant and expressing therein a polynucleotide comprising a nucleotide sequence encoding a Qua-Quine Starch (QQS) polypeptide (SEQ ID NO: 16). The nucleotide sequence is operably linked to a promoter. Thus, in an embodiment, the method further comprises (a) transforming plant cells with a polynucleotide comprising a nucleotide sequence encoding QQS polypeptide having the amino acid sequence of SEQ ID NO: 16, wherein the nucleotide sequence is operably linked to a promoter, (b) regenerating transgenic plants from the transformed plant cells, and (c) identifying and selecting a transformed plant from the transgenic plants which exhibits increased resistance to a pathogen or pest as compared to an untransformed plant of the same species lacking QQS and grown under similar conditions.

QQS can be expressed in the plant using any suitable method as is known in the art (see, for example, U.S. Pat. No. 9,157,091, which issued Oct. 13, 2015, and which is hereby incorporated by reference for its teachings regarding same; see, for example, Examples 1 and 2 therein and the detailed description, portions of which have been reproduced in this paragraph and the next two paragraphs for ease of reference). For example, QQS can be introduced into the plant as a transgene using electroporation, microprojectile bombardment, Agrobacterium-mediated transformation (as exemplified in Examples 1 and 2 of U.S. Pat. No. 9,157, 091), and direct contact of protoplasts. Transformation/ transfection (as well as other techniques used to introduce DNA into a plant or fungus) and regeneration of monocots and dicots is a matter of routine. The particular method employed will depend, in part, on the type of plant or fungus to be transformed/transfected. For example, numerous protocols are described in Agrobacterium Protocols, $2^{nd}$ ed., Vols. 1 and 2, Methods in Molecular Biology, which was edited by Kan Wang and published by Humana Press, Totowa, New Jersey, and which is specifically incorporated herein by reference in its entirety. Such protocols include the floral dip transformation method and methods of transforming leaf explants, cotyledon explants, and root explants, as well as specific protocols for transformation of barrel clover, tobacco, barley, corn, rice (indica and japonica), rye, sorghum, wheat, canola, cotton, Indian mustard, sunflower, alfalfa, chickpea, clover, pea, peanut, pigeon pea, red clover, soybean, tepary bean, taro, cabbage, cucumber, eggplant, lettuce, tomato, carrot, cassava, potato, sweet potato, yam, Bermuda grass, perennial ryegrass, switchgrass, tall fescue, turf grasses, American elm, cork oak, eucalyptus tree, pine, poplar, rubber trec, banana, citrus, coffee, papaya, pineapple, sugarcane, American chestnut, apple, blueberry, grapevine, strawberry, walnut, carnation, chrysanthemum, orchids, petunia, rose, ginseng, hemp, opium poppy, and mushroom. Other methods of Agrobacterium-mediated transformation of cereals are described by Shrawat et al., Plant Biotech. J. 4(6): 575-603 (November 2006), which is specifically incorporated herein by reference in its entirety. Other methods of transformation of legumes are described by Somers et al., Plant Physiol. 131(3): 892-899 (March 2003), which is specifically incorporated herein by reference in its entirety. Methods useful for the transformation of rice are described by Giri et al., Biotech. Adv. 18(8): 653-683 (December 2000), and Hici et al., Plant Mol. Biol. 35(1-2): 205-218 (September 1997), both of which are specifically incorporated herein by reference in their entireties. Vasil et al., Methods Molec. Biol. 111: 349-358 (1999), and Jones et al., Plant Methods 1(1): 5 (Sep. 5, 2005), both of which are specifically incorporated herein by reference in their entireties, describe methods useful for the transformation of wheat. The use of direct DNA uptake in barley has been described by Lazzeri, Methods Molec. Biol. 49: 95-106 (1996), which is specifically incorporated herein by reference in its entirety. The use of temporary immersion in a bioreactor system to transform strawberries is described by Hanhineva et al., BMC Biotech. 7: 11 (2007), which is specifically incorporated herein by reference in its entirety. The introduction of transgenes into plastids, such as chloroplasts, specifically chloroplasts in tobacco, has been described by Daniell et al., Trends Biotech. 23(5): 238-245 (May 2005), which is specifically incorporated herein by reference in its entirety. In this regard, Lutz et al., Plant Physiol. 145(4): 1201-1210 (2007) (specifically incorporated herein by reference in its entirety), provides guidance in the selection of vectors for transformation of the plastid genome in higher plants. Somatic embryogenesis of species-specific chloroplast vectors also has application in plants, such as soybean, carrot, and cotton, for example. Other methods useful for the transformation of beets have been described by Golovko et al., Tsitol. Genet. 39(3): 30-36 (May-June 2005), which is specifically incorporated herein by reference in its entirety.

A nucleotide sequence, which encodes the coding domain sequence (CDS) of QQS, can be incorporated into a vector or a cassette (collectively referred to herein as vectors) for expression in a plant. Numerous expression vectors suitable for stable transformation of plant cells or for the establishment of transgenic plants have been described (see, e.g., Weissbach et al., Methods for Plant Molecular Biology, Academic Press, New York, NY (1989); and Gelvin et al., Plant Molecular Biology Manual, Kluwer Academic Publishers, Norwell, MA (1990)). The Ti plasmid from *Agrobacterium tumefaciens* or a binary *Agrobacterium* vector (Bevan, Nucl. Acids Res. 12: 8711-8721 (1984)) can be used to transform monocots and dicots. Non-Ti vectors, such as viral vectors, can be used to transfer DNA into plant cells, tissues, embryos, and plants. Non-Ti vectors can be introduced through the use of liposome-mediated transformation, polyethylene glycol (PEG)-mediated transformation, viral transfection, micro-injection, vacuum infiltration, electroporation of plant protoplasts, microprojectile bombardment, silicon carbide wiskers, and the like. Sec, e.g., Ammirato et al., Handbook of Plant Cell Culture—Crop Species, MacMillan Pub. Co. (1984); Shimamoto et al., Nature 338: 274-276 (1989); Fromm et al., Bio/Technology 8: 833-839 (1990); and Vasil et al., Biol. Technology 8: 429-434 (1990).

In addition to a coding sequence, a plant transformation/transfection vector comprises one or more 5' and 3' transcriptional regulatory sequences. Transcriptional regulatory sequences can include a promoter, a transcription initiation site, a transcription termination site, a polyadenylation signal, and a 3' terminator region (e.g., PI-II terminator region of potato, octopine synthase 3' terminator region, or nopaline synthase 3' terminator region). If a conventional, nuclear processed intron is present, one or more RNA processing signals, such as intron splice sites, also can be included. Any suitable promoter can be used. In this regard, the QQS promoter can be used. Alternatively, a non-QQS promoter can be used. The promoter can be constitutive, synthetic (e.g., hybrid), inducible, developmentally regulated, environmentally regulated, hormonally regulated, chemically regulated, cell-specific, or tissue-specific (e.g., seed-specific), for example. Constitutive promoters include the cauliflower mosaic virus (CaMV) 35S promoter, the nopaline synthase promoter, and the octopine synthase promoter. Environmentally regulated, inducible promoters include promoters that are induced by light, for example. The napin promoter, the phascolin promoter, and the DC3 promoter are examples of seed-specific promoters, whereas the drul promoter, the 2A11 promoter, and the tomato polygalacturonase promoter are examples of fruit-specific promoters, and PTA29, PTA26, and PTA13 are examples of pollen-specific promoters. The pBAN promoter is a seed coat promoter in *Arabidopsis*, whereas p26, p63, and p63tr are carly seed promoters from *Arabidopsis* (see, e.g., U.S. Pat. App. Pub. No. 2009/0031450). Examples of root-specific promoters are described in U.S. Pat. Nos. 5,618,988; 5,837,848; and 5,905,186. Other promoters are induced by auxin, cytokinin, gibberellin, methyl jasmonate, salicylic acid, heat, light, and the like.

Practice of the methods employs conventional techniques known in the art and described in the literature and herein. See, for example, Sambrook et al., Molecular Cloning: A Laboratory Manual, $2^{nd}$ and $3^{rd}$ ed., Cold Spring Harbor Laboratory Press, Cold Spring Harbor, NY (1989 and 2001); Ausubel et al., Current Protocols in Molecular Biology, John Wiley & Sons, New York, NY (1987); Methods in Enzymology, Academic Press, San Diego, CA, in particular Vol. 34 "Chromatin"; Chromatin Structure and Function, $3^{rd}$ ed., Academic Press, San Diego, CA (1998); and Methods in Molecular Biology, Humana Press, Totowa, NJ, in particular Vol. 119, "Chromatin Protocols."

For conventional techniques used to introduce DNA constructs into the genome of a host plant see, e.g., Weissbach & Weissbach, Methods for Plant Molecular Biology, Section VIII, pp. 421-463, Academic Press, New York, NY (1988), and Grierson & Corey, Plant Molecular Biology, $2^{nd}$ ed., Blackie, London, UK (1988). For example, the DNA construct may be introduced directly into the genomic DNA of a plant cell using techniques, such as electroporation and microinjection of plant cell protoplasts, or the DNA constructs can be introduced directly to plant tissue using biolistic methods, such as DNA particle bombardment (see, e.g., Klein et al., Nature 327: 70-73 (1987)). Alternatively, the DNA constructs may be combined with suitable T-DNA flanking regions and introduced into a conventional *Agrobacterium tumefaciens* host vector. *Agrobacterium tumefaciens*-mediated transformation techniques, including disarming and use of binary vectors, are described in the literature (see, e.g., Horsch et al., Science 233: 4967-498 (1984), and Fraley et al., PNAS USA 80: 4803 (1983)). The virulence functions of the *Agrobacterium tumefaciens* host will direct the insertion of the construct and adjacent marker into the plant cell DNA when the cell is infected by the bacteria using binary T DNA vector (Bevan, Nucleic Acid Research 12: 8711-8721 (1984)) or the co-cultivation procedure (Horsch et al., Science 227: 1229-1231 (1985)). Generally, the *Agrobacterium* transformation system is used to engineer dicots (Bevan et al., Ann. Rev. Genet. 16: 357-384 (1982); Rogers et al., Methods Enzymol. 118: 627-641 (1986)). The *Agrobacterium* transformation system also may be used to transform monocots (Hernalsteen et al., EMBO J. 3: 3039-3041 (1984); Hooykass-Van Slogteren et al., Nature 311: 763-764 (1984); Grimsley et al., Nature 325: 1677-1679 (1987); Boulton et al., Plant Mol. Biol. 12: 31-40 (1989); and Gould et al., Plant Physiol. 95: 426-434 (1991)).

Alternative gene transfer and transformation methods include, but are not limited to, protoplast transformation through calcium-mediated, polyethylene glycol (PEG)-mediated, or electroporation-mediated uptake of naked DNA (Paszkowski et al., EMBO J 3: 2717-2722 (1984); Potrykus et al., Molec. gen. Genet. 199: 169-177 (1985); Fromm et al., PNAS USA 82: 5824-5828 (1985); and Shimamoto, Nature 338: 274-276 (1989)) and electroporation of plant tissues (D'Halluin et al., Plant Cell 4: 1495-1505 (1992)). Additional methods for plant cell transformation include microinjection, silicon carbide-mediated DNA uptake (Kaeppler et al., Plant Cell Reporter 9: 415-418 (1990)), and microprojectile bombardment (Klein et al., PNAS USA 85: 4305-4309 (1988); and Gordon-Kamm et al., Plant Cell 2: 603-618 (1990)).

Transformed cells (or collection of cells, callus, tissue, organ, or organism, e.g., plant) can be identified and isolated by selecting or screening cells for particular traits, such as expression of a marker gene, increased protein content, or increased resistance to a pathogen or a pest. Such screening and selection methodologies are well-known in the art. In addition, physical and biochemical methods can be used to identify transformants. These include Southern blots, PCR amplification, Northern blots, S1 RNase protection, primer-extension, RT-PCR, enzymatic assays, protein gel electrophoresis, western blots, immune-precipitation, enzyme-linked immunoassays, in situ hybridization, enzyme staining, and immuno-staining.

Transformed cells, such as transformed plant cells, can be cultured to regenerate a whole plant, which possesses the transformed genotype and, thus, the desired phenotype.

Such regeneration techniques rely on manipulation of certain phytohormones in a tissue culture growth medium, typically relying on a biocide and/or herbicide marker, which has been introduced together with the desired nucleotide sequences (see, e.g., Evans et al., "Protoplasts Isolation and Culture," in Handbook of Plant Cell Culture, pp. 124-176, Macmillian Publishing Co., New York, NY (1983); Binding, Regeneration of Plants, Plant Protoplasts, pp. 21-73, CRC Press, Boca Raton, FL (1985); and Klee et al., Ann. Rev. Plant Phys. 38: 467-486 (1987)).

An NF-YC4 with a manipulated or modified promoter, desirably one which increases protein production or resistance to a pathogen or a pest, can be isolated and transferred to another eukaryote, such as another plant, which can be the same species, the same genus but a different species, or from a different family or other level of phylogeny. An NF-YC4 with a manipulated or modified transcriptional repressor binding site can be introduced into another eukaryote, such as another plant, using standard breeding techniques and backcrossing. For example, a plant having an NF-YC4 with a manipulated or modified promoter can be crossed with a plant that lacks the NF-YC4 with the manipulated or modified promoter, the resulting generations can be crossed, and plants exhibiting increased protein production or increased resistance to a pathogen or a pest can be selected. Accordingly, when a plant, which has an NF-YC4 with a manipulated or modified promoter, is crossed with a plant, which does not have an NF-YC4 with a modified promoter or has a different gene with a manipulated or modified promoter, hybrid seed can be harvested and planted to obtain hybrid plants or parts thereof. A plant, which has an NF-YC4 with a manipulated or modified promoter and which is amenable to tissue culture, can be a source of cells for tissue culture and regeneration of plants using tissue culture methods known in the art. Similar breeding techniques can be used for non-human animals.

The eukaryotic cell can be a part of a collection of cells, a tissue, an organ, or an organism. In one embodiment, the organism can be a plant, such as a crop plant, a root crop, or a horticultural crop. Examples of a crop plant include soybean, rice, corn, wheat, millet, barley, alfalfa, tomato, apple, pear, strawberry, orange, watermelon, pepper, carrot, potato, sugar beets, yam, lettuce, spinach, sunflower, and rape seed, a flowering plant, such as petunia, rose, and chrysanthemum, conifers and pine trees (e.g., pine, fir, and spruce), a plant used in phytoremediation (e.g., heavy metal-accumulating plants), and a plant used for experimental purposes (e.g., *Arabidopsis*). The plant can be a monocot or a dicot. Examples of monocots include, but are not limited to, oil palm, sugarcane, banana, Sudan grass, corn, wheat, rye, barley, oat, rice, millet and sorghum. Examples of dicots include, but are not limited to, safflower, alfalfa, soybean, coffee, amaranth, rapeseed, peanut, and sunflower. Orders of dicots include Magniolales, Illiciales, Laurales, Piperales, Aristochiales, Nymphacales, Ranunculales, Papeverales, Sarraceniaceae, Trochodendrales, Hamamelidales, Eucomiales, Leitneriales, Myricales, Fagales, Casuarinales, Caryophyllales, Batales, Polygonales, Plumbaginales, Dilleniales, Theales, Malvales, Urticales, Lecythidales, Violales, Salcicales, Capparales, Ericales, Diapensales, Ebenales, Primulales, Rosales, Fabales, Podostemales, Haloragales, Myrtales, Cornales, Proteales, San tales, Rafflesiales, Celastrales, Euphorbiales, Rhamnales, Sapindales, Juglandales, Geraniales, Polygalales, Umbellales, Gentianales, Polemoniales, Lamiales, Plantaginales, Scrophulariales, Camapnulales, Rubiales, Dipsacales, and Asterales. Genera of dicots include *Atropa, Alscodaphne, Anacardium, Ara-*

*chis, Beilschmiedia, Brassica, Carthamus, Cocculus, Croton, Cucumis, Citrus, Citrullus, Capsicum, Catharanthus, Cocos, Coffea, Cucurbita, Daucus, Duguctia, Eschscholzia, Ficus, Fragaria, Galucium, Glycine, Gossypium, Helianthus, Hevea, Hyoscyamus, Lactuca, Landolphia, Linum, Litsca, Lycopersicon, Lupinus, Manihot, Majorana, Malus, Medicago, Nicotiana, Olea, Parthenium, Papaver, Persea, Phaseolus, Pistacia, Pisum, Pyrus, Prunus, Raphanus, Ricinus, Senecio, Sinomenium, Stephania, Sinapsis, Solanum, Theobroma, Trifolium, Trigonella, Vicia, Vinca, Vilis,* and *Vigna.* Orders of monocots include *Alismatales, Hydrocharitales, Najadales, Triuridales, Commelinales, Eriocaulales, Restionales, Poales, Juncales, Cyperales, Typhales, Bromeliales, Zingiberales, Arecales, Cyclanthales, Pandanales, Arales, Lilliales,* and *Orchidales.* Genera of monocots include *Allium, Andropogon, Aragrostis, Asparagus, Avena, Cynodon, Elacis, Festuca, Festulolium, Heterocallis, Hordeum, Lemna, Lolium, Musa, Oryza, Panicum, Pannesetum, Phleum, Poa, Secale, Sorghum, Triticum,* and *Zea.* Other plants include Gymnospermae, such as the orders Pinales, Ginkgoales, Cycadales, and Gnetales, such as the genera *Abies, Cunninghamia, Picca, Pinus,* and *Pseudotsuga,* such as fir and pine. In another embodiment, the organism can be an alga, such as a unicellular flagellate, such as a species of *Chlamydomonas.* In yet another embodiment, the organism can be a non-human animal, such as livestock animals, e.g., cattle, pigs, chickens, turkeys, sheep, and bison.

The pathogen can be a bacterium, a virus, a fungus, or a seed plant. The pest can be an insect (such as an aphid), a plasmodiophorid, a mite, or a nematode. In embodiments, the pathogen is a bacterium or a virus, and the pest is an aphid.

The bacterium can be any plant bacterium. Examples include, but are not limited to, a Firmicute, an Actinobacterium, or a Proteobacterium. The Proteobacterium can be an Alphaproteobacterium, a Betaproteobacterium, or a Gammaproteobacterium. The Alphaproteobacterium can be an *Agrobacterium,* a *Sphingomonas,* or a *Candidatus Liberibacter.* The Betaproteobacterium can be an *Acidovorax,* a *Burkholderia,* a *Ralstonia,* or a *Xylophilus.* The Gammaproteobacterium can be an Enterobacteriaceae, a Pseudomonodaceae, or a Xanthomonodaceae. The Enterobacteriaceae can be *Brenneria, Dickeya, Enterobacter, Erwinia, Ewingella, Pantoea, Pectobacterium, Candidatus Phlomobacter, Samsonia,* or *Serratia.* The Pseudomonodaceae can be *Pseudomonas.* The Xanthomonodaceae can be *Xanthomonas* or *Xylella.* The bacterium can be a *Clavibacter, Curtobacterium, Rathayibacter, Leifsonia, Nocardia, Rhodococcus, Streptomyces, Bacillus, Clostridium, Spiroplasma, Candidatus Phytoplasma,* or Microbacteria. Specific examples of bacteria include, but are not limited to, *Clavibacter michiganensis* or a subspecies thereof, *Curtobacterium flaccumfaciens, Rathayibacter rathayi, Rathayibacter tritici, Rathayibacter toxicus, Leifsonia xyli* or subspecies thereof, *Rhodococcus fascians, Sphingomonas suberifaciens, Sphingomonas melonis, Agrobacterium vitis, Agrobacterium tumefaciens, Agrobacterium rubi, Acrobacterium larrymoorei, Acidovorax avenae, A. avenae citrulli, A. avenae avenae, Burkholderia cepacia, Burkholderia gladioli, Burkholderia andropogonis, Burkholderia caryophylli, Burkholderia glumae, Burkholderia plantarii, Dickeya dadantii, Dickeya solani, Erwinia amylovora, Ralstonia solanacearum, Ralstonia syzygii, Candidatus Phlomobacter fragariae, Candidatus Liberibacter asiaticus, Pectobacterium carotovorum, Pectobacterium atrosepticum, Pseudomonas syringae, Pseudomonas savastanoi, Pseudomonas marginalis, Pseudomonas viridiflava,*

*Xanthomonas arboricola, Xanthomonas axonopodis, Xanthomonas campestris, Xanthomonas hortorum, Xanthomonas oryzae, Xanthomonas axonopodis, Xanthomonas translucens, Xanthomonas vasicola,* or *Xylella fastidiosa.* According to Mansfield et al. (Mol. Plant Pathol. 13: 614-629 (2012)), the top bacterial plant pathogens are *Pseudomonas syringae* pathovars, *Ralstonia solanacearum, Agrobacterium tumefaciens, Xanthomonas oryze* pv. *oryze, Xanthomonas campestris pathovars, Xanthomonas axonopodis* pv. *manihotis, Erwinia amylovora, Xylella fastidiosa, Dickeya dadantii, Dickeya solani, Pectobacterium carotovorum,* and *Pectobacterium atrosepticum.*

The fungus can be any plant fungus. Examples include, but are not limited to, Ascomycetes, such as *Fusarium* spp. (causal agents of *Fusarium* wilt disease), *Fusarium graminearum, Fusarium oxysporum, Thielaviopsis* spp. (causal agents of canker rot, black root rot, and *Thielaviopsis* root rot), *Verticillium* spp., *Magnaporthe grisea* (causal agent of blast of rice and gray leaf spot in turfgrasses), *Magnaporthe oryzae, Sclerotinia sclerotiorum* (white mold), and powdery mildews. Other examples include Basidiomycetes, such as *Ustilago* spp., *Ustilago maydis, Rhizoctonia* spp., *Rhizoctonia solani, Phakospora pachyrhizi* (causal agent of soybean rust), *Puccinia* spp. (causal agents of severe rusts of virtually all cereal grains and cultivated grasses), and *Armillaria* spp. ("honey fungus" species; virulent pathogens of trees and produce-eligible mushrooms). According to Dean et al. (Mol. Plant Pathol. 13: 414-430 (2012)), the top ten plant fungal pathogens are *Magnaporthe oryzae, Botrytis cinerea, Puccinia* spp., *Fusarium graminearum, Fusarium oxysporum, Blumeria graminis, Mycosphaerella graminicola, Colletotrichum* spp., *Ustilago maydis,* and *Melampsora lini.* According to Kamoun et al. (Mol. Plant Pathol. 16: 413-434 (2015)), the top ten oomycetes are *Phytophthora infestans* (late blight), *Hyaloperonospora arabidopsidis* (downy mildew), *Phytophthora ramorum* (sudden oak death and Ramorum disease), *Phytophthora sojae* (stem and root rot), *Phytophthora capsici* (blight, stem and fruit rot, and various others), *Plasmopara viticola* (downy mildew), *Phytophthora cinnamomi* (root rot and dieback), *Phytophthora parsitica* (root and stem rot and various others), *Pythium ultimum* (damping off and root rot), and *Albugo candida* (white rust).

The seed plant can be dodder, mistletoe, or witchweed. Such plants are hemi-parasitic or parasitic on other plants.

The virus can be any plant virus. The virus can be transmitted through sap, by an insect, by a nematode, by a plasmodiophorid, by a mite, by a seed, or by pollen. Examples include, but are not limited to, members of the genera Alfamoviruses (e.g., Bromoviridae), Alphacryptoviruses (e.g., Partitiviridae), Badnaviruses, Betacryptoviruses (e.g., Partitiviridae), Bigeminiviruses (e.g., Geminiviridae), Bromoviruses (e.g., Bromoviridae), Bymoviruses (e.g., Potyviridae), Capilloviruses, Carlaviruses, Carmoviruses (e.g., Tombusviridae), Caulimoviruses, Closteroviruses, Comoviruses (e.g., Comoviridae), Cucumoviruses (e.g., Bromoviridae), Cytorhabdoviruses (e.g., Rhabdoviridae), Dianthoviruses, Enamoviruses, Fabaviruses (e.g., Comoviridae), Cucumoviruses (e.g., Bromoviridae), Cytorhabdoviruses (e.g., Rhabdoviridae), Dianthoviruses, Enamoviruses, Fabaviruses (e.g., Comoviridae), Fijiviruses (e.g., Reoviridae), Furoviruses, Hordeiviruses, Hybrigeminiviruses (e.g., Geminiviridae), Idacoviruses, Ilarviruses (e.g. Bromoviridae), Ipomoviruses (e.g. Potyviridae), Luteoviruses, Machlomoviruses, Macluraviruses, Marafiviruses, Monogeminiviruses (e.g., Geminiviridae), Nanaviruses, Ncroviruses, Nepoviruses (e.g., Comoviridae), Nucleorhabdoviruses (e.g., Rhabdoviridae), Oryzaviruses (e.g., Reoviridae), Ourmiaviruses, Phytoreoviruses (e.g., Reoviridae), Potexviruses, Potyviruses (e.g., Potyviridae), Rymoviruses (e.g., Potyviridae), Sequiviruses (e.g., Sequiviridae), Sobemoviruses, Tenuiviruses, Tobamoviruses, Tobraviuses, Tombusviruses (e.g., Tombusviridae), Tospoviruses (e.g. Bunyaviridae), Trichoviruses, Tymoviruses, Umbraviruses, unassigned Potyviruses (e.g., Potyviridae), unassigned Rhabdoviruses (e.g. Rhabodiviridae), Varicosaviruses, Waikaviruses (e.g., Sequiviridae), and ungrouped viruses. Other examples of viruses include, but are not limited to, citrus tristeza virus, barley yellow dwarf virus, potato leafroll virus, and tomato bushy stunt virus. According to Scholthof et al. (Mol. Plant Pathol. 12: 938-954 (2011)), the top ten plant viruses are tobacco mosaic virus, tomato spotted wilt virus, tomato yellow leaf curl virus, cucumber mosaic virus, potato virus Y, cauliflower mosaic virus, African cassava mosaic virus, plum pox virus, Brome mosaic virus, and potato virus X.

Examples of viruses transmitted through sap include, but are not limited to, tobacco mosaic virus, potato virus X, potato virus Y, and a cucumber mosaic virus.

Examples of viruses transmitted by insects include, but are not limited to, Rhabdoviridae, Reoviridae, Potyvirus, Cucumovirus, Luteovirus, Begomovirus, Tospovirus, Comovirus, Sobemovirus, tomato yellow leaf curl virus, tomato pseudo-curly top virus, tomato spotted wilt virus, and lettuce infectious yellow virus. The insect can be an aphid, a whitefly, a hopper, a thrip, or a beetle. Aphids can spread Potyvirus, Cucumovirus, and Luteovirus. Whiteflies can spread Begomovirus, tomato yellow leaf curl virus, and lettuce infectious yellow virus. Hoppers can spread Rhabdoviridae, Reoviridae, and tomato pseudo-curly top virus. Thrips can spread Tospovirus and tomato spotted wilt virus. Beetles can spread Comovirus and Sobemovirus.

Nematodes can spread Nepovirus, Tobravirus, tobacco ringspot virus, and tobacco rattle virus, for example. According to Jones et al. (Mol. Plant Pathol. 14: 946-961 (2013)), the top ten nematodes are root-knot nematodes (i.e., *Meloidogyne* spp.), cyst nematodes (i.e., *Heterodera* spp. and *Globodera* spp.), root lesion nematodes (i.e., *Pratylenchus* spp.), the burrowing nematode (ie., *Radopholus similis*), *Ditylenchus dipsaci,* the pine wilt nematode (i.e., *Bursaphelenchus xylophilus*), the reniform nematode (i.e., *Rotylenchulus reniformis*), *Xiphinema index, Nacobbus aberrans,* and *Aphelenchoides besseyi.*

Plasmodiophorids can spread Benyvirus, Bymovirus, Furovirus, Pecluvirus, Pomovirus, barley yellow mosaic virus, and beet necrotic yellow vein virus, for example.

Mites can spread Rymovirus, Tritimovirus, and wheat streak mosaic virus.

Seed can spread Hordeivirus, bean common mosaic virus, and barley stripe mosaic virus, for example.

Once the exogenous DNA is stably incorporated in a transgenic plant and confirmed to be operable, it can be introduced into other plants by sexual crossing. Thus, a method of producing a plant with increased protein content or increased resistance to a pathogen or a pest is also provided. The method comprises crossing a plant obtained in accordance with the above with a second plant to produce progeny plants and selecting progeny plants with increased protein content or increased resistance to a pathogen or a pest. The method can further comprise crossing selected progeny plants with said second plant to produce backcross progeny plants, selecting a first backcross progeny plant that has increased protein content or increased resistance to a pathogen or a pest to produce selected backcross progeny plants, and repeating the crossing and selecting three or more times to produce a backcross progeny plant that has increased protein content or increased resistance to a pathogen or a pest. Similar procedures can be used, or adapted for use, in algae, which reproduce vegetatively, asexually, and sexually, and non-human animals.

A cell, collection of cells, tissue, organ, or organism in which the NF-YC4 gene comprises a promoter comprising a transcriptional repressor binding site that has been manipulated or modified so that the transcriptional repressor cannot prevent transcription of the NF-YC4 is also provided. The cell, collection of cells, tissue, organ, or organism has an increased protein content compared to a corresponding cell, collection of cells, tissue, organ, or organism in which the NF-YC4 gene comprises a promoter comprising a transcriptional repressor binding site that has not been manipulated or modified. In embodiments, the organism can be a plant or an alga, such as a unicellular flagellate. In another embodiment, the organism can be a non-human animal, such as livestock animals, e.g., cattle, pigs, chickens, turkeys, sheep, and bison.

A seed of the aforementioned plant is also provided, as is a hybrid of the aforementioned organism, such as a hybrid plant. A seed of the hybrid plant is also provided, as are corresponding structures resulting from vegetative, asexual, and sexual reproduction of algae, and fertilized eggs of non-human animals. Other progeny, clones, cell lines, and cells are also provided.

EXAMPLES

The following examples serve to illustrate the present disclosure. The examples are not intended to limit the scope of the invention as claimed.

Example 1

This example describes the making of 35S::QQS and 35S::AtNF-YC4 fusion constructs and transformation.

The 35S::QQS and 35S::AtNF-YC4 fusion constructs were made by cloning the amplified full-length coding sequence into the binary vector pB2GW7 as previously described (Li et al. (2015), supra). Briefly, the QQS coding domain sequence (CDS) or the NF-YC4 CDS from *Arabidopsis* (AtNF-YC4) was inserted in vector pB2GW7 (see FIGS. 1*a* and 1*b*, which are maps of the vectors), which contains a Bar gene (phosphinotricin acetyltransferase gene) under the control of Pnos (nos promoter) and Tnos (nos terminator) from nopaline synthase from *Nicotiana tabacum*. The CDS on this vector is controlled by p35S (cauliflower mosaic virus (CaMV) 35S promoter) and terminated by T35S (CaMV 35S). Only the region between LB and RB was introduced to plants to generate transgenic plants.

Constructs were introduced into *Agrobacterium tumefaciens* strain GV3101 for transformation in *Arabidopsis thaliana* ecotype Columbia (Col-0), and *Agrobacterium tumefaciens* strain EHA101 for transformation into soybean (*Glycine max*) cultivar William 82 (Li et al. (2015), supra), rice (*Oryza sativa*) cultivar Kitakke, and corn (*Zea mays*) line B104.

Transformants expressing QQS (QQS-E) were identified on the basis of BAR selection followed by polymerase chain reaction (PCR) analysis for presence of the QQS gene as previously described (Li et al. (2015), supra).

Soybean QQS-E Williams 82 was used as pollen donor to cross with Iowa soybean elite lines (IA1022, IA2079, IA2102, IA2053, and IA3022) in the field (Williams 82 was used as a control). The F1 generation was grown in the greenhouse in pots with three plants/pot under a controlled environment of 16 hrs of light and 8 hrs of dark at 27/20° C. The F2 generation was planted in the field in Ames, IA. QQS-E mutants were identified on the basis of BAR selection followed by PCR analysis for the presence of the QQS gene. The segregating wild-type (WT) plants that were not resistant to herbicide and did not express QQS were used as sibling controls.

Rice plants were grown in a growth chamber under a controlled environment of 16 hrs of light and 8 hrs of dark at 28/25° C. T3 generation plants were analyzed. Similarly, the plants were tested by herbicide and PCR analysis to identify transformants and WT sibling controls.

Corn plants were grown in the field in Ames, IA. The plants were backcrossed to B104. Similarly, the plants were tested by herbicide and PCR analysis to identify transformants and WT sibling controls.

*Arabidopsis* were transformed, grown and harvested as previously described. See Li et al. (2009), supra.

Example 2

This example describes analysis of plant composition.

Composition of leaves (starch staining and quantification and protein) was determined in *Arabidopsis* seedling shoots 20 days after planting (DAP) in a growth chamber and in rice second leaves (next to flag leaves) of the primary tillers from plants 30 DAP. Three (for starch) or five (for protein) plants per replicate and three replicates from each independent T2 line (*Arabidopsis*) and T3 line (rice) were analyzed. Leaves were harvested at the end of the light period. Seeds were harvested per individual plant for *Arabidopsis*, rice and soybean. For leaf and seed protein quantification, plant materials were baked at 71° C. Dry leaf/seed tissue (0.07 g) was used for each determination. Total protein content was measured. Total nitrogen was determined by using a LECO CHN-2000 (LECO, St. Joseph, MI), and converted to protein content (Li et al. (2015), supra).

The entire aerial portion of *Arabidopsis* was stained with $I_2$/KI, whereas the middle part of the second leaf (next to the flag leaf) of the primary tiller of rice was collected and cut into small pieces (about 1-1.5 cm long).

Soybean and corn seeds were analyzed (protein, oil and fiber for soybean; protein, oil and starch for corn) by near infrared spectroscopy (NIRS) using a Bruins Grain Analyzer S/N 106110 (Munich, Germany). About 60 g of seeds per plant were tested, with three biological replicates for each line.

Example 3

This example describes yeast two-hydrid assays.

The Matchmaker System 3 (Clontech, Mountain View, CA) was used to identify QQS-interacting proteins using an *Arabidopsis* Columbia cDNA library constructed with three-day-old etiolated seedlings (Arabidopsis.org/servlets/TairObject?type=library&id=23). For reciprocal yeast two-hybrid assays, QQS and AtNF-YC4 were cloned into pGBKT7 (bait vector) and pGADT7 (prey vector), respectively (Clontech).

Example 4

This example describes bimolecular fluorescence complementation (BiFC) assays.

QQS and AtNF-YC4 were fused in-frame to the N-terminus of nYFP (N-terminal end of yellow fluorescent protein (YFP)) and cYFP (C-terminal end of YFP), respectively. *Agrobacterium* strain GV3101 transformed with QQS-nYFP and AtNF-YC4-cYFP constructs were co-infiltrated into *Nicotiana tabaccum*. The reconstituted YFP signal was observed 48 h after infiltration under a Zeiss Axioplan II fluorescence microscope.

Example 5

This example describes the purification of HIS-MBP-tagged recombinant NF-Y.

*E. coli* transformants containing the AtNF-YC4 gene (or other NF-Y genes or gene fragments) were grown in 0.6 L of Luria-Bertani (LB) medium at 37° C. until an $OD_{600}$ of 0.90, and then isopropyl-$\beta$-D-thiogalactopyranoside (IPTG) was added to a final concentration of 0.075 mM. After incubation at 12° C. for 20 h, the induced cells were harvested by centrifugation at 5,000×g for 5 min. His-MBP-tagged (i.e., 6×histidine-maltose binding protein-tagged) protein was purified using Ni sepharose 6 Fast Flow (GE Healthcare Life Sciences, Pittsburgh, PA) affinity chromatography under native conditions at 4° C. The cell pellet was re-suspended in 15 ml of binding buffer (50 mM $NaH_2PO_4$, pH 8.0, 500 mM NaCl, and 30 mM imidazole). The cells were lysed by intermittent sonication. After centrifugation at 10,000×g for 20 min, the resins were added to the cleared lysate. After shaking at 4° C. for 30 min, the lysate-resins mixture was loaded in a column. The resins were washed with wash buffer (50 mM $NaH_2PO_4$, pH 8.0, 500 mM NaCl, and 60 mM imidazole). The binding protein was eluted off the column with elution buffer (50 mM NaH₂PO4, pH 8.0, 500 mM NaCl, and 250 mM imidazole). The eluted proteins were dialyzed twice against PBS buffer (140 mM NaCl, 2.7 mM KCl, 10 mM $Na_2HPO_4$, and 1.8 mM $KH_2PO_4$, pH 7.3). The protein concentration was determined by BCA protein assay kit (Thermo Scientific, St. Louis, MO) with bovine serum albumin (BSA) as the standard.

Example 6

This example describes the expression and purification of GST-tagged QQS.

*E. coli* transformants expressing the QQS gene were grown in 1.2 L of Luria-Bertani (LB) medium at 37° C. until an $OD_{600}$ of 0.9, and then isopropyl-$\beta$-D-1-thiogalactopyranoside (IPTG) was added to a final concentration of 0.075 mM. After incubation at 12° C. for 20 h, the induced cells were harvested by centrifugation at 5,000×g for 5 min. Purification of the GST-tagged (i.e., glutathione-S-transferase-tagged) QQS was conducted using glutathione sepharose 4B (GE Healthcare Life Sciences) affinity chromatography under native conditions at 4° C. The cell pellet was re-suspended in 15 ml of PBS buffer (140 mM NaCl, 2.7 mM KCl, 10 mM $Na_2HPO_4$, and 1.8 mM $KH_2PO_4$, pH 7.3), and cells were lysed by intermittent sonication. After centrifugation at 10,000×g for 20 min, the resins were added to the cleared lysate. After shaking at 4° C. for 30 min, the lysate-resins mixture was loaded onto a column. The resins were washed with PBS. The binding protein was eluted off the column with elution buffer (50 mM Tris-HCl, 10 mM reduced glutathione, 5 mM DTT, pH 8.0). The eluted proteins were dialyzed twice against PBS buffer. The protein concentration was determined by BCA protein assay kit (Thermo Scientific) with BSA as the standard.

Example 7

This example describes pull-down assays.

Purified His-MBP-tagged protein (5 μg) was mixed with bead-immobilized GST-QQS fusion protein (10 μg) in 1 ml of PBS buffer containing 1% NP-40, 1 mM DTT, and 0.5 μg/μl BSA. The mixture was incubated at 4° C. for 2 hr. GST protein immobilized on beads was used in incubations with His-MBP-tagged proteins as a negative control. The beads were recovered by centrifugation, washed six times with 1 ml of PBS buffer, and re-suspended in 50 μl SDS-sample buffer. Fifteen μl of the resultant sample were analyzed by SDS-PAGE on a 12% gel, following by immunoblotting and analysis with antiserum against MBP.

Example 8

This example describes statistical design and analyses.

Plants were grown, collected and analyzed in a randomized complete block design or completely randomized design. Qualitative and quantitative analyses were conducted with a minimum of three biological determinations from each independent transgenic line and each control. For compositional analyses, plant samples were assigned randomized numbers and provided to the analysis facilities for determination in a randomized order with no designator of genotype.

Data are presented as mean±SE. Two sets of independent samples were compared using Student's t-test (two-tailed) with assumption of equal variances (n=3). P<0.05 was considered significant (*); P<0.01 was considered very significant (**).

Example 9

This example describes phylogenetic inference.

Sequences were selected as potential NF-Y genes with a HMMER 3.0 (Finn et al., Nucleic Acids Res. 39: W29-37 (2011)) search (hmmsearch) of the PF00808.18 PFam domain (histone fold-like domain) against the protein sequences of *Glycine max, Oryza sativa, Arabidopsis thaliana, Chlamydomonas reinhardtii, Zea mays, Homo sapiens, Mus musculus, Danio rerio, Saccharomyces cerevisiae*, and *Dictyostelium discoideum*. The trees were built using the PhyML package (Guindon et al., Systematic Biology 52: 696-704 (2003)) (with parameters '-a e-f m') and visualized in Archaeopteryx (sites.google.com/site/cmzmasek/home/software/archaeopteryx). See FIGS. 2*a-c*, which show NF-YC4 sequences, and FIG. 3, which is a phylogenetic tree of NF-YC4 genes from evolutionarily diverse species.

Example 10

This example demonstrates that the QQS transgene affects protein content and carbohydrate content in elite soybean lines with varied seed protein contents; thus, the effect of QQS is not limited to the soybean line Williams 82.

The QQS transgene was introduced into elite soybean lines with varied seed protein contents by crossing with QQS-expressing (QQS-E) Williams 82 soybean as the pollen donor. The self-pollinated offspring of F2 and F3 generations of these crosses containing the QQS transgene were similar to the respective segregating siblings in morphology, development, seed size, seed shape, seed weight, and seed yield per plant. Seed composition (F3 generation) was analyzed by near infrared spectroscopy (NIRS).

Expression of QQS increased seed protein content in each elite line regardless of the initial protein level in the line (FIG. 4A). Seed protein content is shown in FIG. 4A, which is a bar graph of soybean elite lines expressing QQS and their respective segregating sibling controls vs. seed protein in the F3 generation (%/g fresh weight with 13% moisture). The percent increase in seed protein compared to the respective segregating sibling control is indicated at the top of the mutant bar. a=segregating sibling lacking the QQS gene from QQS-E Williams 82 transformants; b=QQS-E Williams 82 transformants; c=segregating sibling controls lacking the QQS gene from crosses of IA elite lines or Williams 82 and QQS-E Williams 82; d=QQS-E mutants from crosses of IA elite lines and QQS-E Williams 82. Student's t-test was used to compare QQS-E and controls. **P<0.01. Specifically, expression of QQS increased the seed protein content by 9% in the low-protein line IA1022, 6-7% in the medium-protein lines IA2079 and IA2102, and 7-11% in the high-protein lines IA2053 and IA3022, when compared to the respective segregating siblings.

FIG. 4B is a bar graph of soybean elite lines expressing QQS and their respective segregating sibling controls vs. seed oil in the F3 generation (%/g fresh weight with 13% moisture). a=segregating sibling lacking the QQS gene from QQS-E Williams 82 transformants; b=QQS-E Williams 82 transformants; c=segregating sibling controls lacking the QQS gene from crosses of IA elite lines or Williams 82 and QQS-E Williams 82; d=QQS-E mutants from crosses of IA elite lines or Williams 82 and QQS-E Williams 82. Student's t-test was used to compare QQS-E and controls. *P<0.05. **P<0.01.

FIG. 4C is a bar graph of soybean elite lines expressing QQS and their respective segregating sibling controls vs. seed fiber in the F3 generation (%/g fresh weight with 13% moisture). a=segregating sibling lacking the QQS gene from QQS-E Williams 82 transformants; b=QQS-E Williams 82 transformants; c=segregating sibling controls lacking the QQS gene from crosses of IA elite lines or Williams 82 and QQS-E Williams 82; d=QQS-E mutants from crosses of IA elite lines or Williams 82 and QQS-E Williams 82. Student's t-test was used to compare QQS-E and controls. *P<0.05. *P<0.01.

Example 11

This example demonstrates that the QQS transgene affects protein content in rice and corn.

The QQS transgene was introduced into rice (cultivar Kitakke; see FIG. 1A, which is a map of the vector). Rice plants were grown in a growth chamber in a randomized complete block design. Leaves of T3 plants and the mature T4 seeds from three independent transformation events were analyzed in triplicate. Independent transgenic lines of rice plants expressing the QQS gene (QQS-E) and their seed were visually and developmentally similar to their respective wild-type (WT) sibling controls. However, the expression of the QQS gene in three independent transgenic lines decreased starch content in leaves expressing QQS (QQS-E) and its wild-type sibling (sibling) and increased protein content in leaves (see FIG. 5A, which is a bar graph of rice (cultivar Kitakke) expressing QQS (QQS-E) and its wild-type sibling (sibling) vs. leaf protein (%/dry weight); all data show mean±SE, n=3; Student's t-test was used to compare QQS-E and controls; P<0.01). The mean protein increase in mature rice seeds across the three transgenic lines was 20% (see FIG. 5B, which is a bar graph of rice (cultivar Kitakke) expressing QQS (QQS-E) and its wild-type sibling (sibling) vs. seed protein (%/dry weight); all data show mean±SEM, n=3; Student's t-test was used to compare QQS-E and controls; P<0.01).

The QQS transgene was also introduced into corn, which was grown in the field. Kernel protein (% per dry weight) increased from about 10% to about 20% in QQS-expressing corn as compared to sibling controls (see Li et al., PNAS USA 112(47): 14734-14739 (2015), which is hereby incorporated by reference).

Example 12

This example describes yeast two-hybrid screening using QQS as bait against a cDNA library from *Arabidopsis* seedlings to identify a gene with which QQS interacts.

Yeast two-hybrid screening using QQS as bait against a cDNA library from *Arabidopsis* seedlings identified *Arabidopsis* Nuclear Factor YC4 (AtNF-YC4) as a gene with which QQS interacts. Reciprocal yeast two-hybrid assays are consistent with a QQS and AtNF-YC4 interaction; AtNF-YC4 on bait has an auto-signal, and QQS-prey+ AtNF-YC4-bait signal is higher than AtNF-YC4-bait. The interaction between QQS and AtNF-YC4 was further confirmed by yeast two-hybrid pairwise reciprocal studies (FIG. 6). FIG. 6 is a bar graph of empty vectors of prey+bait (BK+AD), QQS-prey+empty vector of bait (BK+QQS), AtNF-YC4-bait+empty vector of prey (AtNF-YC4+AD), and AtNF-YC4-bait+QQS-prey (AtNF-YC4+QQS) plus reporter gene relative expression. *P<0.05. **P<0.01. Statistical analysis indicates AtNF-YC4-bait+QQS-prey expression is higher than AtNF-YC4-bait (*P<0.05). Bimolecular fluorescence complementation assay in tobacco leaves indicated that QQS and AtNF-YC4 interact with the cytosol and the nucleus; no YFP signal was detected without a QQS and AtNF-YC4 interaction.

Example 13

This example describes glutathione-S-transferase (GST) pull-down assaying using purified recombinant AtNF-YC4-GST fusion proteins to identify the region in AtNF-YC4 required for QQS binding.

Proteins containing different regions of AtNF-YC4 (i.e., full-length, amino acids 1-72, amino acids 73-162, amino acids 163-250, amino acids 1-162, and amino acids 73-250) fused with GST were expressed. The fusion proteins were used in pull-down assays. Analysis indicated that QQS binds to amino acids in the region from amino acid 73 to amino acid 162 of AtNF-YC4. This region corresponds to the location of the histone-fold-like domain. Bimolecular fluorescence complementation assay in tobacco leaves indicated QQS and NF-YC4 interact with the cytosol and the nucleus. An interaction localized in the nucleus was used as a positive control. GST pull-down assay also showed an interaction between QQS and the soybean and rice NF-YC4 homologs.

Example 14

This example describes GST pull-down assaying using purified recombinant *Arabidopsis* Nuclear Factor YB7 (AtNF-YB7)-GST fusion proteins to determine whether QQS generally binds to histone-fold-like domain proteins.

AtNF-YB7 contains a histone-fold-like domain and is predicted to complex with AtNF-YC4 (Hackenberg et al., Mol. Plant 5: 876-888 (2012)). AtNF-YB7, however, was not bound by QQS in GST pull-down assays, indicating that QQS binds proteins with histone-fold-like domains having certain characteristic features.

Example 15

This example describes the in vivo co-expression of QQS and AtNF-YC4 in tobacco leaf.

QQS and AtNF-YC4 were co-expressed in vivo in tobacco leaf. QQS-NF-YC4 complexes were detected in the cytosol and the nucleus. These data (see FIGS. 1a and 1b for vector maps) suggest that predominantly cytosolic QQS (Li et al. (2009), supra) and NF-YC (Kahle et al., Molec. Cell. Biol. 25: 5339-5354 (2005)) bind in the cytosol and move into the nucleus akin to the model of NF-YB binding NF-YC in the cytosol and NF-YB-NF-YC complexes moving into the nucleus.

Example 16

This example describes the interaction of QQS with rice and soybean proteins having amino acid sequences similar to amino acids 73-162 of AtNF-YC4.

Rice and soybean proteins having amino acid sequences similar to amino acids 73-162 of AtNF-YC4 were selected by phylogenetic analysis of all NF-Y histone-fold-like domains in protein-coding genes from genomes of ten diverse eukaryotic species (FIG. 3, which is a phylogenetic tree of the NF-YC genes from evolutionarily diverse species of eukaryotes and which shows the analysis for rice, soybean, and *Arabidopsis*). Physical interaction of QQS with soybean (Glyma06g17780 and Glyma04g37291) and rice (Os3g14669, Os2g07450, and Os6g45640) homologs was examined by GST pull-down assay. QQS interacted with all homologs. These findings are consistent with the expression of QQS conferring a high-protein phenotype to soybean and rice via interaction with NF-YC4.

Example 17

This example describes the over-expression of AtNF-YC4 and OsNF-YC4 in *Arabidopsis*.

The AtNF-YC4 (At=*Arabidopsis thaliana*) transgene was over-expressed in *Arabidopsis*. Seedlings of 20-day-old T2 plants from three independent transformation events were analyzed. Over-expression of AtNF-YC4 decreased starch content in leaves by approximately 16% (see FIG. 7A, which is a bar graph of *Arabidopsis* over-expressing NF-YC4 (AtNF-YC4-OE) and wild-type *Arabidopsis* (WT) vs. leaf starch (mg/g fresh weight); all data in bar graph show mean±SE, n=3; Student's t-test was used to compare starch composition in the WT and AtNF-YC4-OE lines; *P<0.05) and increased protein content in leaves by around 17% (see FIG. 7B, which is a bar graph of *Arabidopsis* over-expressing NF-YC4 (AtNF-YC4-OE) and wild-type *Arabidopsis* (WT) vs. leaf protein (mg/g dry weight); all data in bar graph show mean±SE, n=3; Student's t-test was used to compare protein composition in the WT and AtNF-YC4-OE lines; **P<0.01).

These data suggest that QQS acts in conjunction with AtNF-YC4 to alter the allocation of nitrogen and carbon. QQS is believed to bind NF-YC4, and the resulting complex moves to the nucleus and alters transcription of the genes that are repressed and activated by the NF-YC4-associated NF-Y complex. These shifts in expression result in increased protein content and decreased starch content.

The OsNF-YC4 (Os=*Orzya sativa*; Os3g14669) transgene also was over-expressed in *Arabidopsis*. The NF-YC4 CDS from *Oryza sativa* was inserted in vector pB2GW7, which contains a Bar gene (phosphinotricin acetyltransferase gene) under the control of Pnos (nos promoter) and Tnos (nos terminator) from nopaline synthase from *Nicotiana tabacum*. The OsNF-YC4 on this vector is controlled by p35S (cauliflower mosaic virus (CaMV) 35S promoter) and terminated by T35S (CaMV 35S). Only the region between LB and RB was introduced to *Arabidopsis* plants to generate transgenic *Arabidopsis* OsNF-YC4-OE plants (see FIG. 1D, which is a map of the vector). Over-expression of OsNF-YC4 decreased starch content in leaves by ~16% compared to *Arabidopsis* WT. Protein content is being analyzed.

Example 18

This example describes the targeted removal of an identified repressor motif in the promoter region of the NF-YC4 gene.

A binding motif of RAV1, specifically RAV1-A, was identified in the promoter region of the NF-YC4 gene. The RAV1-A motif has the sequence CAACA (see, e.g., Kagaya et al., Nucleic Acids Res. 27: 470-478 (1999), for discussion of RAV1). A "W box" motif also was identified in the promoter region of the NF-YC4 gene (see, e.g., Nishiuchi et al., J. Biol. Chem. 279: 55355-55361 (2004), for discussion of W box in promoter region of ERF3 gene). A W box motif has the sequence TGACY, wherein Y=C or T. Such motifs were identified in the plant cis-acting regulatory DNA elements (PLACE) database: 1999 (Nucleic Acids Res. 27(1): 297-300 (1999)); such motifs were identified using SIGNAL SCAN (Prestridge, CABIOS 7: 203-206 (1991); available on the worldwide web at dna.affrc.go.jp/PLACE/ signalscan.html). Motifs also can be found using Plantcare (bioinformatics.psb.ugent.be/webtools/plantcare/html). The repressor motifs in the promoter region of the NF-YC4 gene in soybean and rice were deleted. With regard to soybean, specifically the region between the RAV1-A motif and the W box motif was deleted (i.e., nts 360-391 having the sequence GGTCAGTTTTTGTTAACATTAATTTTTAGGAT [SEQ ID NO: 17]; see FIG. 2E). With regard to rice, specifically the RAV1-A motif was deleted (i.e., nts 250-254 having the sequence of CAACA). A construct with the mutated promoter and a construct with a full-length promoter were separately fused with luciferase as a reporting gene. Each construct on a binary vector was separately transformed into *Agrobacterium* GV3101 and then transformed into *Nicotiana benthamiana* (Leuzinger et al., Vis. Exp. 77 (2013)). The recommended developmental stage of *N. benthamiana* and *Agrobacterium* growth and infiltration concentration were used. The recombinant luciferase protein was transiently expressed. Luciferase expression was quantified in tobacco leaves that had been *Agrobacterium*-infiltrated. At least three replicates in three plants were included per construct. Removal of the repressor motif from the NF-YC4 gene from soybean resulted in increased expression of luciferase in ⅔ replicates. Similarly, removal of the repressor motif from the NF-YC4 gene from rice resulted in increased expression of luciferase in ⅔ replicates. Overall, the total luciferase expression of all three replicates increased for the NF-YC4 gene from soybean and the NF-YC4 gene from rice.

In a separate experiment, three separate mutations to the promoter region of OsNF-YC4 were generated to remove the transcription repressor motif. In the "pro1" mutation the "RAV1" motif at 1164 bp upstream was deleted (see SEQ ID NO: 2 and FIG. 2A). In the "pro2" mutation the "RAV1" motif at 982 bp upstream and the "Class II ERF" motif at 979 bp upstream were deleted (sec SEQ ID NO: 3 and FIG. 2B). The RAV1 motifs and the intervening sequence were deleted in the "pro3" mutation (see SEQ ID NO: 4 and FIG. 2B). The control "proFull" contained the full-length promoter region, i.e., 1,448 bp upstream of the start codon (see SEQ ID NO: 1 and FIG. 2A). The promoter regions were fused with the luciferase coding region, transformed into *Agrobacterium*, and then transformed into tobacco as described above. The results are shown in FIG. 9.

FIG. 9 is a graph of LUC activity from tobacco, in which the transcription repressor motif in the promoter region of rice NF-YC4 has been deleted (OsNF-YC4pro1, Os-NF-YC4pro2, and Os-NF-YC4pro3), vs. relative luciferase (LUC) activity as compared to control (OsNF-YC4proFull). Data represent mean±SEM, n=3. Student's t-test was used to compare the LUC activity driven by promoters with deletions and the full-length promoter. *P<0.05. Error bars indicate the standard errors.

As shown, NF-YC4 expression is up-regulated when the transcription repressor motif in the promoter region is removed. Deletion of two ERF motifs had a greater effect than deletion of one RAV1 motif or the combined deletion of one RAV1 motif and one ERF motif.

In yet another experiment, three separate mutations to the promoter region of GmNF-YC4 were generated to remove the transcription repressor motif. In the "pro1" mutation an ERF motif (reverse), a RAV1 motif (forward) and the intervening sequence were deleted (see SEQ ID NO: 9 and FIG. 2D). In the "pro2" mutation an ERF motif (reverse), a RAV1 motif (reverse) and the intervening sequence were deleted (see SEQ ID NO: 11 and FIG. 2D), whereas two RAV1 motifs and the intervening sequence were deleted in the "pro3" mutation (see SEQ ID NO: 13 and FIG. 2E). The control "proFull" contained the full-length promoter region, i.e., 1,448 bp upstream of the start codon (see SEQ ID NO: 8 and FIG. 2C). The promoter regions were fused with the luciferase coding region, transformed into *Agrobacterium*, and then transformed into tobacco as described above. The results are shown in FIG. 8.

FIG. 8 is a graph of LUC (luciferase) activity from tobacco, in which the transcription repressor motif in the promoter region of soybean NF-YC4 has been deleted (pSoy-LUC DEL1, pSoy-LUC DEL2, and pSoy-LUC DEL3), vs. relative LUC activity as compared to control (pSoy-LUCFull). Data represent mean±SEM, n=3. Student's t-test was used to compare the LUC activity driven by promoters with deletions and the full-length promoter. *P<0.05. Error bars indicate the standard errors. As shown, NF-YC4 expression is up-regulated when the transcription repressor motif in the promoter region is removed. Deletion of both RAV1 motifs had a greater effect than the combined deletion of one RAV1 motif and one ERF motif.

In still yet another experiment, rice T0 plants (Kitaake) were transformed with a CRISPR/Cas9 construct targeted to introduce mutations in the promoter region of OsNF-YC4. The use of gRNA/Cas9 technology involved multiple steps for targeted gene editing in rice. A target sequence in OsNF-YC4 was selected (see SEQ ID NOs: 6 and 7), a plasmid expressing the nucleases (i.e., Cas9 and gRNA) was designed and constructed, embryonic calli were transformed via *Agrobacterium*-mediated gene transfer, primary transgenic lines were screened for site-specific DNA changes and identified, and PCR genotyping was used to identify mutants with deleted sequences. More than 19 mutant plants (T0) with heterozygous mutations were identified. T0 plants were self-crossed for progeny with homozygous mutations and segregation out of T-DNA. The T1 seeds have been harvested. Mutants with homozygous mutations and free of T-DNA insertions will be selected.

Example 19

This example describes the screening of the promoter region of the NF-YC4 gene to identify a region that may contain a transcriptional repressor binding site.

Genomic DNA of Kitakke leaves is used as a template for PCR to generate mutated OsNF-YC4 promoter constructs. The promoter region (the 1 kb region upstream from the start codon) of the NF-YC4 gene is mutated by sequential deletion of 100 bp segments, starting from position −1000 bp (upstream from start codon). The mutated NF-YC4 promoter with a 100-bp deletion in the middle of the promoter (i.e., position −900 bp to −100 bp) is constructed by double-joint PCR (Yu et al., Fungal Genet. Biol. 41: 973-981 (2004)).

Constructs with mutated promoters and one construct with a full-length promoter are separately fused with luciferase as a reporting gene. Each construct on a binary vector is separately transformed into *Agrobacterium* GV3101 and then transformed into *Nicotiana benthamiana* (Leuzinger et al. (2013), supra). The recommended developmental stage of *N. benthamiana* and *Agrobacterium* growth and infiltration concentration are used. The recombinant luciferase protein is transiently expressed. Luciferase expression is quantified in tobacco leaves that have been *Agrobacterium*-infiltrated to identify which deletion results in increased expression compared to the full-length promoter. The promoter with increased expression is proposed to contain a transcriptional repressor binding site. At least three replicates in three plants are included per construct.

Example 20

This example describes the effects of over-expression and under-expression of QQS on the expression of genes involved in plant defense.

Total RNA was extracted from pooled leaf samples using TRIzol (Life Technologies, Carlsbad, CA). The RNA was further purified using the QIAGEN RNeasy Mini Kit (QIAGEN, Valencia, CA) with the DNAse I (Life Technologies, Carlsbad, CA) treatment to remove DNA contamination.

A 200-bp short-insert library was constructed. Transcriptome sequencing was performed with an Illumina HiSeq2000 system using V3 Reagent (91 air end sequencing). Low-quality reads were filtered out by removing reads with adaptors, reads with more than 5% unknown nucleotides, and reads with more than 20% bases having a quality of ≤10. The cleaned reads were aligned to the reference *Arabidopsis thaliana* genome in Phytozome version 8.0 (phytozome.net) using TopHat. The mapped reads were counted by htseq-count (huber.embl.de/users/anders/HT-Seq/doc/count.html).

Analysis of RNA-Seq data from QQS RNAi (down-regulating QQS), QQS OE (over-expressing QQS) and wild-type Col-0 *Arabidopsis* plants revealed that plant defense-related marker genes had perturbed transcript levels relative to wild-type *Arabidopsis* as shown in Table 1.

TABLE 1

| Locus | Gene | Mean (three replicates) | | | Ratio | | P value | |
| --- | --- | --- | --- | --- | --- | --- | --- | --- |
| | | QS RNAi | QS OE | T (Col-0) | QS RNAi to WT | QS OE to WT | QS RNAi vs WT | QS OE vs WT |
| AT1G19640 | JMT jasmonic acid carboxyl methyltransferase | 4.5 | 5 | 9.7 | .75 | .78 | .06 | .03 |
| AT1G32640 | MYC2 transcription factor MYC2 | 23.5 | 39 | 85.7 | .13 | .54 | .67 | .04 |
| AT1G43160 | RAP2.6 ethylene-responsive transcription factor RAP2-6 | .5 | 1.5 | .3 | .38 | .63 | .45 | .09 |
| AT1G56650 | PAP1 transcription factor MYB75 | 17 | 19.5 | 2.3 | .42 | .45 | .04 | .01 |
| AT1G64280 | NPR1 Regulatory protein NPR1 | 13 | 9 | 12.3 | .01 | .79 | .87 | .18 |
| AT1G80840 | WRKY40 putative WRKY transcription factor 40 | 0 | 6.5 | 8.3 | .09 | .99 | .89 | .07 |
| AT2G14610 | PR1 pathogenesis-related protein 1 | 28.5 | 20.5 | 07.3 | .42 | .02 | .16 | .19 |
| AT2G26020 | PDF1.2b putative defensin-like protein | | .5 | .3 | .23 | .19 | .14 | .19 |
| AT2G43790 | MPK6 MAP kinase 6 | 69.5 | 25.5 | 62.0 | .05 | .77 | .87 | .09 |
| AT3G05500 | AT3G05500 Rubber elongation factor protein; stress related protein | 4.5 | 02.5 | 0.7 | .05 | .45 | .90 | .04 |
| AT3G14620 | CYP72A8 cytochrome P450, family 72, subfamily A, polypeptide 8 | 04.5 | 11 | 16.0 | .96 | .98 | .67 | .81 |
| AT4G01720 | WRKY47 putative WRKY transcription factor 47 | 9.5 | 5.5 | 5.0 | .56 | .44 | .01 | .00 |
| AT5G22570 | WRKY38 putative WRKY transcription factor 38 | .5 | 9.5 | 8.0 | .42 | .64 | .06 | .14 |

The patterns can be categorized into three groups. The first group is comprised of one gene with decreased expression in both mutants, namely WRKY47, which is highly activated by bacterial infection and is involved in the induction of basal defense (Truman et al., Plant J. 46(1): 14-33 (2006)). The second group is comprised of four genes with increased expression in both mutants. The four genes are JMT, which is a key metabolic enzyme of jasmonate (JA)-regulated plant responses (Seo et al., PNAS USA 98(8): 4788-4793 (2001)), MYC2, which is a JA-responsive transcriptional factor that modulates antagonism between jasmonate and ethylene (ET) signaling (Chico et al., Plant Cell 26(5): 1967-1980 (2014); Song et al., Plant Cell 26(1): 263-279 (2014); and Zhang et al., Plant Cell 26(3): 1105-1117 (2014)), PAP1, a JA-responsive transcriptional factor that activates anthocyanin biosynthesis depending on the activation of Col1 by JA (Shan et al., J. Exp. Bot. 60(13): 3849-3860 (2009)), and RAB2-6, which is an ET-responsive transcriptional factor that triggers callose deposition in planta (Ali et al., BMC Plant Biol. 13: 47 (2013)). The third group is comprised of three genes with decreased expression in mutants in which QQS is down-regulated and increased expression in mutants in which QQS is over-expressed. The three genes are WRKY38, which is an NPR-dependent basal defense negative regulator that regulates SA-triggered immunity (Caillaud et al., PLOS Biol. 11(12): e1001732 (2013); Kim et al., Plant Cell 20(9): 2357-2371 (2008); Pre et al., Plant Physiol. 147(3): 1347-1357 (2008); and Seo et al. (2001), supra), NPR1 regulatory protein, and PRI pathogenesis-related protein 1.

Example 21

This example demonstrates that viral infection decreased in transgenic *Arabidopsis thaliana* plants overexpressing NF-YC4 or QQS.

Turnip mosaic virus carrying green fluorescent protein (TuMV-GFP) inoculation assay was performed as previously described (Yang et al., Molecular Plant-Microbe Interactions 20(4): 358-370 (2007)) with some minor modifications. Frozen TuMV-GFP-infected turnip (Seven Top) leaves were ground in 20 mM sodium phosphate buffer (pH 7.2, 1:6 wt/vol) and filtered through Miracloth (Calbiochem, San Diego, CA) to obtain the inoculum. The titer of the inoculum was adjusted to yield well-separated GFP loci.

*Arabidopsis thaliana* plants were grown for seven weeks in 10 hr of light at 22° C. to allow large rosette leaves to develop. Rosette leaves were dusted with Carborundum and rub-inoculated with TuMV-GFP using a cotton-stick applicator. At 120 hr after inoculation (hai), GFP foci on the inoculated rosette leaves were counted under UV illumination (100-W Blak-Ray longwave UV lamp; UVP, Upland, CA). Each line had three biological replicates of 10 randomly selected plants. The average foci number of 10 plants for each line was calculated, and the significance of foci number differences between lines was determined using the Student's t-test ($P < 0.01$ or $0.05$).

For each genotype, 40 single GFP foci were randomly selected and photographed on a Zeiss Stemi SV11 fluorescence dissecting microscope using a Zeiss AxioCam MRc5 digital camera (Hewezi et al., Plant Cell 20(11): 3080-3093 (2008)). The digital files were then processed using Zeiss AxioVision software. Each photographed GFP focus was processed with the ImageJ measure tool (NIH) and calibrated against the correct scaling of the original image from the Stemi SV11. The total area for the GFP focus was calculated as square millimeters. The individual measurements for the GFP focus of each line were used to calculate an average focus size for each line tested. Significance of size differences between lines was determined via the Student's t-test ($P < 0.01$ or $0.05$).

TuMV-GFP was inoculated on *A. thaliana* plants with different genetic backgrounds of QQS and NF-YC4. GFP foci (number indicates the ability of TuMV to initiate the infection process) were counted and the sizes of GFP foci (size indicates the ability of TuMV to reproduce in planta) were measured at five days after inoculation. *Arabidopsis thaliana* Col-0 lines with altered QQS expression and altered expression of the QQS interactor NF-YC4 were used in all infection assays. The lines used were Col-0 (few trichomes, control for transformants) for AtQQS RNAi (QQS-downregulating), AtQQS OE (QQS-overexpressing), and AtNF-YC4 OE (NF-YC4-overexpressing) and Col-0

(trichomes, control for T-DNA knock-out (KO) mutants) for AtQQS KO and AtNF-YC4 KO.

As shown in FIG. 10A (a graph of mutant vs. controls for average foci number per 10 *Arabidopsis* plants (±standard error at 120 hours after virus inoculation (hai); Student's t-test was used to compare foci number in the control and QQS or NF-YC4 mutants; *P<0.05; P<0.01; *P<0.001) and 10B (a graph of mutant vs. controls for average focus size (mm$^2$) (±standard error at 120 hai after virus inoculation (n=40); Student's t-test was used to compare foci number in the control and QQS or NF-YC4 mutants; ***P<0.001), AtNF-YC4 OE plants had significantly decreased numbers of GFP foci, approximately 88% fewer than the controls. In contrast, AtNF-YC4 KO plants had slightly increased foci numbers, approximately 16.5% more than the controls; though small, the Student's t-test suggested that the difference was significant. Similarly, the AtQQS OE plants had 21.7% fewer foci compared to the control plants, while the AtQQS RNAi plants had 12.2% more foci than the control plants, and the AtQQS KO plants had 45.9% more foci than the controls. These results showed that over-expressing either AtQQS or AtNF-YC4 impaired the viral infection initiation, while silencing or knocking-out AtQQS or AtNF-YC4 facilitated the viral infection initiation. YC4 over-expression almost blocked the viral infection.

The changes in foci sizes had a similar trend. The foci in AtNF-YC4 KO, AtQQS KO and AtQQS-silenced plants were 27.8%, 52.5% and 51.9% larger, respectively, than the controls, whereas the foci in AtNF-YC4 OE and AtQQS OE plants were 51% and 32% smaller, respectively, than the controls.

These results showed that overexpressing AtNF-YC4 or AtQQS impairs viral reproduction, while silencing or knocking-out AtNF-YC4 or AtQQS facilitates viral reproduction. The assays indicate that QQS and its interactor, NF-YC4, decrease initiation of infection and decrease viral reproduction in planta. Thus, they are positive regulators of plant immune response, since over-expression of each increases plant resistance to virus.

Example 22

This example demonstrates that bacterial growth decreased in transgenic *Arabidopsis thaliana* plants overexpressing NF-YC4 or QQS.

*A. thaliana* plants were grown in growth chamber under 10 hr of light and 14 hr of dark at 22° C. for 4-5 weeks. *Pseudomonas syringae* were washed and re-suspended in inoculation buffer (10 mM $MgCl_2$, 0.05% Silwet L-77). Plants were sprayed with a bacterial inoculum with the bacterial level adjusted to $10^8$ colony-forming units (CFU)/mL (Katagiri et al., The *Arabidopsis thaliana-Pseudomonas syringae* Interaction. *The Arabidopsis Book/American Society of Plant Biologists,* 1:e0039, doi.org/10.1199/tab.0039 (2002)). Bacterial levels in planta were determined by cutting leaf disks with a cork borer (inner diameter 0.5 cm) and completely homogenizing them in 500 μl of the inoculation buffer. The resulting suspensions containing the bacteria was diluted and plated on KB plates with the appropriate antibiotics.

Bacterial growth in planta of Pst DC3000 and the ACEL strain in the same set of *A. thaliana* plants listed in Example 21 was examined. Pst DC3000 is a bacterial pathogen that robustly infects *A. thaliana* plants, while ΔCEL, a mutated Pst DC3000 strain with mutations in multiple effector genes, is a non-virulent strain that grows slowly in planta. Pst DC3000 grew approximately 1,000-fold in four days, while ΔCEL grew approximately 10-fold. The growth of Pst DC3000 was greatly impaired in plants over-expressing AtNF-YC4 or AtQQS, with 88% and 63% decreases, respectively. In contrast, in the AtQQS or AtNF-YC4 RNAi and KO lines, the growth of Pst DC3000 was increased by approximately 30%. The increased growth of Pst DC3000 was quite significant in the AtQQS RNAi plants, while that in AtQQS or AtNF-YC4 KO lines was not significant at the level of p=0.05.

On the other hand, it was quite obvious that the growth of ΔCEL in the AtQQS or AtNF-YC4 RNAi or KO lines was strongly enhanced with approximately a 2.6-fold increase. The growth change of ΔCEL was not similarly significant in the AtQQS or AtNF-YC4 over-expression plants. Overall, the data about the altered growth of both bacterial strains in *A. thaliana* plants of different genetic backgrounds indicate that over-expressing AtNF-YC4 or AtQQS enhances the plant immune responses, making the robustly infectious bacterial pathogen less virulent and slow-growing, while silencing or knocking out AtNF-YC4 or AtQQS impairs the plant immune responses, making the non-virulent bacterial pathogen grow better. So, these data consistently suggest that AtNF-YC4 and AtQQS are positive regulators of plant immune responses.

The results are summarized in FIG. 11. FIG. 11 is a graph of Day 0 (0 dpi) and Day 4 (4 dpi) after inoculation in *Arabidopsis* plants for Pst DC3000 and ΔCEL vs. number of bacteria ($\log_{10}$ ($CFU/cm^2$)). Initial inoculum was adjusted uniformly to $10^8$ CFU/mL. Error bars indicate the standard errors. Student's t-test was used to compare bacterial number in the control and QQS or NF-YC4 mutants. P<0.01. *P<0.001.

Example 23

This example demonstrates that bacterial growth decreased in transgenic soybean plants overexpressing NF-YC4 or expressing QQS.

Figure 1C:
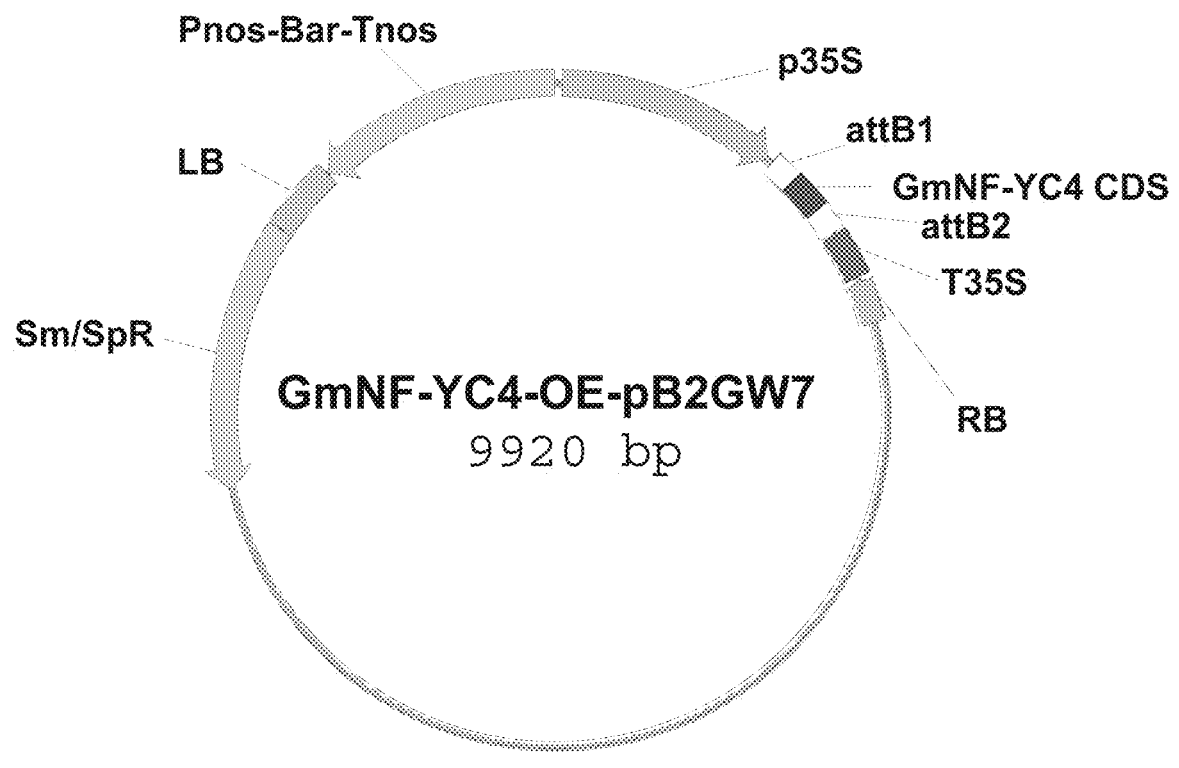
FIG. 1C is a map of a vector expressing NF-YC4 from soybean.
Figure 1D:
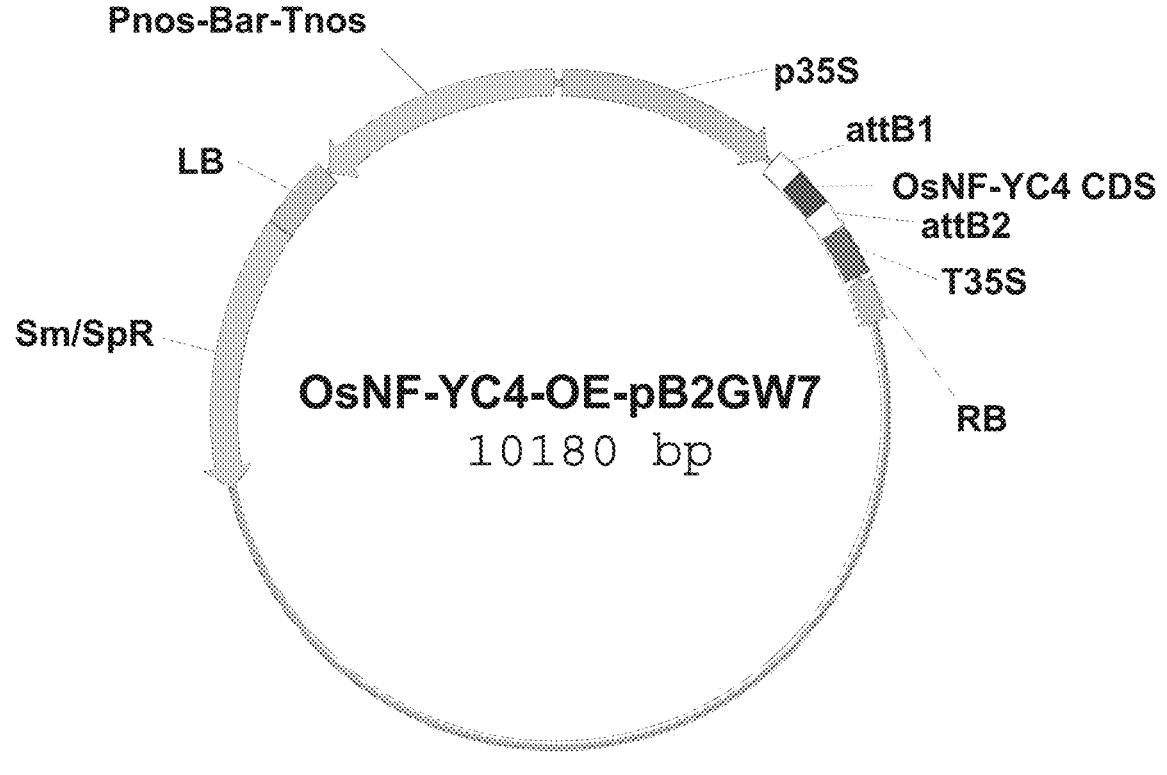
FIG. 1D is a map of a vector expressing NF-YC4 from rice.
Figure 1E:
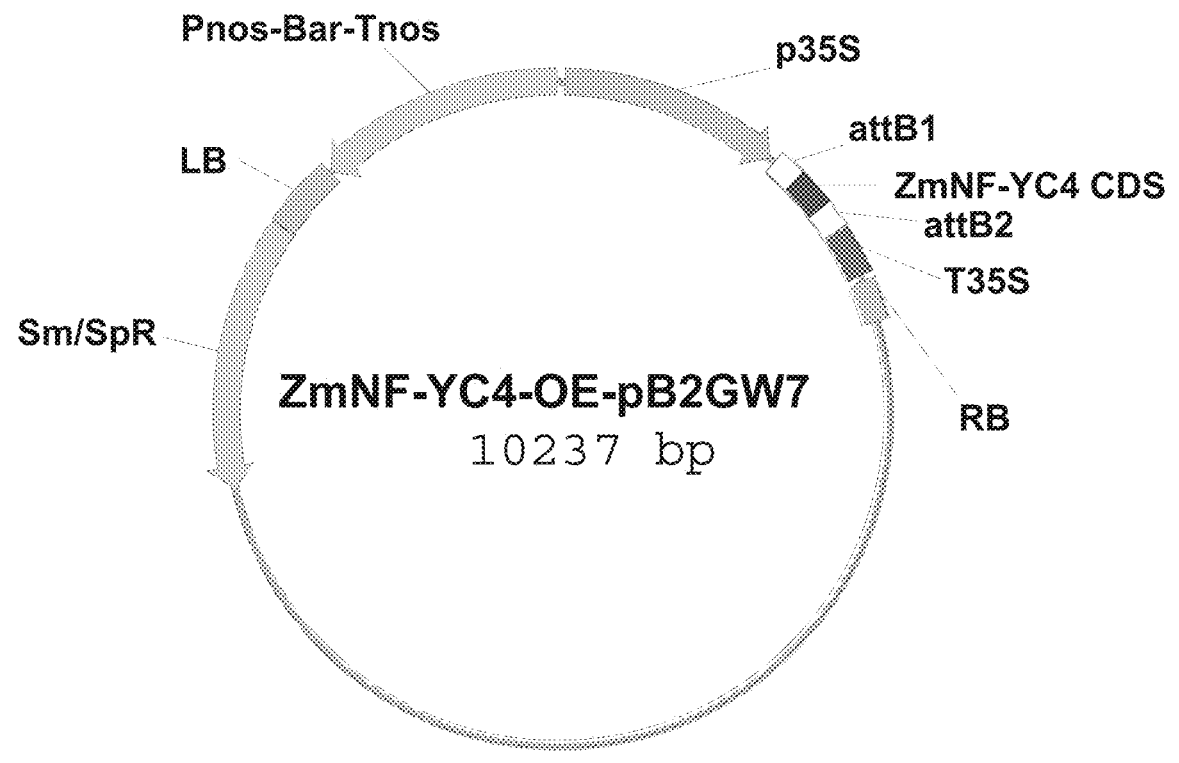
FIG. 1E is a map of a vector expressing NF-YC4 from corn.

The NF-YC4 CDS from *Glycine max* (GmNF-YC4) was inserted into vector pB2GW7, which contains a Bar gene (phosphinotricin acetyltransferase gene) under the control of Pnos (nos promoter) and Tnos (nos terminator) from nopaline synthase from *Nicotiana tabacum* (see FIG. 1C, which is a map of the vector). The GmNF-YC4 on this vector is controlled by p35S (cauliflower mosaic virus (CaMV) 35S promoter) and terminated by T35S (CaMV 35S). Only the region between LB and RB was introduced into plants to generate transgenic plants.

Stable, transgenic soybean lines expressing AtQQS (AtQQS E; see Example 1 and FIG. 1A for a map of vector, QQS-OE-pB2GW7) or over-expressing GmNF-YC4 (Glyma06g17780; GmNF-YC4 OE) were generated and grown in growth chamber under 14 hrs of light and 10 hrs of dark at 22° C. The soybean mutant plants of QQS E, GmNF-YC4-OE, and empty vector control were selected by PCR-screening of leaf DNA. The first trifoliates on 23-day-old soybeans were used for inoculation. Freshly cultured *P. savastanoi* pv. *glycinea* Race 4 (PsgR4) was suspended in the inoculation buffer (see Example 22) to the final concentration of around $10^7$ CFU/mL. The leaflets of each trifoliate leaf were pricked by needle before 5 μL of the inoculum were placed onto each wound (10/leaflet). Bacterial levels in planta were determined at 10 days after inoculation as described above.

Psg causes bacterial blight on soybean, which was considered as a great threat to soybean production. PsgR4 is one of the most virulent strains, since it can infect almost all commercial soybean cultivars. Using the soybean line carrying the empty vector as control, PsgR4 grew much slower in the soybean GmNF-YC4 OE line and the soybean AtQQS-E line, with a 62.4% and a 55.3% decrease, respectively. The impaired bacterial growth of PsgR4 in soybean lines over-expressing GmNF-YC4 or expressing AtQQS indicated that GmNF-YC4 and AtQQS enhance soybean immune response as well, which is consistent with the above data that NF-YC4 and QQS are positive regulators of plant immune responses.

The results are summarized in FIG. 12A. FIG. 12A is a graph of soybean line for number of bacteria (CFU*$10^4$/cm²). Initial inoculum was adjusted uniformly to $10^7$ CFU/mL. Error bars indicate the standard errors. Student's t-test was used to compare bacterial number in the control and QQS-E or NF-YC4-OE mutants. **P<0.01. (EV=empty vector)

To confirm that GmNF-YC4 was over-expressed in the transgenic soybean lines, the expression level of GmNF-YC4 was determined using quantitative real-time PCR. Approximately 100 mg soybean leaves were used for RNA isolation using the RNeasy Plant Mini Kit (Qiagen) according to the manufacturer's instructions. Two μg of RNA and SuperScript® III First Strand kit (Invitrogen) were used for cDNA synthesis. Quantitative real-time PCR (qRT-PCR) was performed using the cDNA and gene-specific primers (GmNF-YC4Fd: 5'-CCTCCCAGGCATGGCAGTCC-3' [SEQ ID NO: 18] and GmNF-YC4Rev: 5'-CCAT-CAAGGCTCCGCTGG-3' [SEQ ID NO: 19]. Each cDNA was amplified by quantitative PCR using iQ™SYBR® Green Supermix (Bio-Rad) and iCycler real-time PCR system (Bio-Rad). GmACTIN expression was used to normalize the expression value in eash sample, and the relative expression values were determined against mock samples using the comparative Ct method ($2^{-\Delta\Delta Ct}$).

GmACTIN (Glyma 15g050200) was used as the reference gene (Liu et al., Mol. Plant Microbe Interact. 27(8): 824-834 (2014)). The expression level of GmNF-YC4 in the GmNF-YC4 OE line was 4.47-fold higher than expression in the soybean control line.

The results are summarized in FIG. 12B. FIG. 12B is a graph of NF-YC4-OE soybean line for relative expression level. Error bars indicate the standard errors. **P<0.01. (EV=empty vector)

Example 24

This example demonstrates that aphids decreased in transgenic soybean plants overexpressing NF-YC4 or expressing QQS.

Transgenic soybean plants were generated as described in Example 23. Soybean seeds were planted at 25° C. with a photoperiod of 16 h of light and 8 h of dark. Plants were infested 18 days after planting. Seven days after infestation, the average number of aphids per plant was determined. The results are shown in FIG. 13.

FIG. 13 is a graph of soybean genotype QQS-E 16-6 (QQS-expressing line 16-6), QQS-E 32-6 (QQS-expressing line 32-6), control, NF-YC4-OE L1 (NF-YC4 overexpressing line 1), and NF-YC4-OE L2 (NF-YC4 overexpressing line 2) vs. average number of aphids per plant. Errors bars indicate the standard errors. Student's t-test was used to compare aphid number in the control and QQS-E or NF-YC4-OE mutants. *P<0.05. **P<0.01 (EV=empty vector). As shown, the average number of aphids per plant decreased from about 20% to about 30% in soybean plants expressing QQS or overexpressing NF-YC4 as compared to control.

Example 25

This example demonstrates that protein or protein+oil content increased in the seeds of transgenic soybean plants overexpressing NF-YC4.

Transgenic soybean plants (Williams 82) overexpressing NF-YC4 were generated as described in Example 23 and grown in a field. T2 seeds were analyzed using NIRS as described in Example 2. Data are shown in FIGS. 14A-14E.

FIG. 14A is a graph of transformation event (1, 2, 3 and 4; each number indicates a different transformation event) of transformed soybean overexpressing NF-YC4 (NF-YC4-OE) vs. protein content as compared to sibling control. Error bars indicate the standard errors. Student's t-test was used to compare protein content in the NF-YC4-OE mutants and sibling controls. *P<0.05. **P<0.01. As shown, protein increased from about 6% to about 12% in soybean plants overexpressing NF-YC4 as compared to control.

FIG. 14B is a graph of transformation event (1, 2, 3 and 4; each number indicates a different transformation event) of transformed soybean overexpressing NF-YC4 (NF-YC4-OE) vs. oil content as compared to sibling control. Error bars indicate the standard errors. Student's t-test was used to compare oil content in the NF-YC4-OE mutants and sibling controls. *P<0.05. As shown, oil in soybean plants overexpressing NF-YC4 as compared to control was either similar or decreased.

FIG. 14C is a graph of transformation event (1, 2, 3 and 4; each number indicates a different transformation event) of transformed soybean overexpressing NF-YC4 (NF-YC4-OE) vs. protein+oil content as compared to sibling control. Error bars indicate the standard errors. Student's t-test was used to compare protein+oil content in the NF-YC4-OE mutants and sibling controls. *P<0.05. **P<0.01. As shown, protein+oil content increased from about 5% to about 7% in soybean plants overexpressing NF-YC4 as compared to control.

FIG. 14D is a graph of transformation event (1, 2, 3 and 4; each number indicates a different transformation event) of transformed soybean overexpressing NF-YC4 (NF-YC4-OE) vs. seed fiber (% per fresh weight with 13% moisture) as compared to sibling control. Error bars indicate the standard errors. Student's t-test was used to compare fiber content in the NF-YC4-OE mutants and sibling controls. **P<0.01. As shown, seed fiber decreased from about 3.4% to about 5.6% in soybean plants overexpressing NF-YC4 as compared to control.

FIG. 14E a graph of transformation event (1, 2, 3 and 4; each number indicates a different transformation event) of transformed soybean overexpressing NF-YC4 (NF-YC4-OE) vs. seed weight per plant (grams per plant) as compared to sibling control. Error bars indicate the standard errors. Student's t-test was used to compare seed weight per plant in the NF-YC4-OE mutants and sibling controls. As shown, seed weight per plant in soybean plants overexpressing NF-YC4 was similar to control.

Example 26

This example demonstrates that protein content increased in the seeds of transgenic corn plants overexpressing NF-YC4.

Transgenic corn plants overexpressing NF-YC4 were generated and grown in a field. The construct from Example 1 was introduced into corn via *Agrobacterium*-mediated transformation. Backcross 2 (BC2; B104 background backcross to B104) seeds were analyzed using NIRS as described in Example 2. Data are shown in FIGS. 15A-15C.

FIG. 15A is a graph of transformed corn overexpressing *Arabidopsis* NF-YC4 (AtNF-YC4-OE) vs. kernel protein (% per dry weight) as compared to sibling control. Error bars indicate the standard errors. Student's t-test was used to compare protein content in the NF-YC4-OE mutants and sibling controls. **P<0.01. As shown, kernel protein increased about 17% compared to control.

FIG. 15B is a graph of transformed corn overexpressing *Arabidopsis* NF-YC4 (AtNF-YC4-OE) vs. kernel oil (% per dry weight) as compared to sibling control. Error bars indicate the standard errors. Student's t-test was used to compare oil content in the NF-YC4-OE mutants and sibling controls. As shown, kernel oil was similar to control.

FIG. 15C is a graph of transformed corn overexpressing *Arabidopsis* NF-YC4 (AtNF-YC4-OE) vs. kernel starch (% per dry weight) as compared to sibling control. Error bars indicate the standard errors. Student's t-test was used to compare starch content in the NF-YC4-OE mutants and sibling controls. **P<0.01. As shown, kernel starch decreased about 2.2% as compared to control.

Example 27

This example demonstrates that protein content increased in the seeds of transgenic rice plants overexpressing NF-YC4.

Transgenic rice plants overexpressing NF-YC4 were generated and grown in a growth chamber. The construct from Example 17 (pB2GW7-OsNF-YC4) was introduced into rice via *Agrobacterium*-medium transformation. Data are shown in FIGS. 16A and 16B.

FIG. 16A is a graph of transformed rice overexpressing rice NF-YC4 (OsNF-YC4-1-OE) vs. seed starch (mg per g dry weight) as compared to wild-type. Error bars indicate the standard errors. Student's t-test was used to compare seed starch content in the NF-YC4-OE mutants and controls. **P<0.01. As shown, seed starch decreased by about 6%.

FIG. 16B is a graph of transformed rice overexpressing rice NF-YC4 (OsNF-YC4-1-OE) vs. seed protein (mg per g dry weight) as compared to wild-type. Error bars indicate the standard errors. Student's t-test was used to compare seed protein content in the NF-YC4-OE mutants and controls. **P<0.01. As shown, seed protein increased by about 37%.

All patents, patent application publications, journal articles, textbooks, and other publications mentioned in the specification are indicative of the level of skill of those in the art to which the disclosure pertains. All such publications are incorporated herein by reference to the same extent as if each individual publication were specifically and individually indicated to be incorporated by reference.

The invention illustratively described herein may be suitably practiced in the absence of any element(s) or limitation(s), which is/are not specifically disclosed herein. Thus, for example, each instance herein of any of the terms "comprising," "consisting essentially of," and "consisting of" may be replaced with either of the other two terms. Likewise, the singular forms "a," "an," and "the" include plural references unless the context clearly dictates otherwise. Thus, for example, references to "the method" includes one or more methods and/or steps of the type, which are described herein and/or which will become apparent to those ordinarily skilled in the art upon reading the disclosure.

The terms and expressions, which have been employed, are used as terms of description and not of limitation. In this regard, where certain terms are defined under "Definitions" and are otherwise defined, described, or discussed elsewhere in the "Detailed Description," all such definitions, descriptions, and discussions are intended to be attributed to such terms. There also is no intention in the use of such terms and expressions of excluding any equivalents of the features shown and described or portions thereof. Furthermore, while subheadings, e.g., "Definitions," are used in the "Detailed Description," such use is solely for ease of reference and is not intended to limit any disclosure made in one section to that section only; rather, any disclosure made under one subheading is intended to constitute a disclosure under each and every other subheading.

It is recognized that various modifications are possible within the scope of the claimed invention. Thus, it should be understood that, although the present invention has been specifically disclosed in the context of preferred embodiments and optional features, those skilled in the art may resort to modifications and variations of the concepts disclosed herein. Such modifications and variations are considered to be within the scope of the invention as claimed herein.

What is claimed is:

1. A genetically modified plant, or a part from the genetically modified plant, comprising a genetically modified endogenous nuclear factor Y subunit C4 (NF-YC4) promoter operably linked to an endogenous NF-YC4 protein coding sequence, wherein an agent for modifying a nucleotide sequence of said NF-YC4 promoter, modifies at least one transcriptional repressor binding site in the nucleotide sequence of said NF-YC4 promoter, and whereupon the transcriptional repressor cannot prevent transcription of the NF-YC4 coding sequence and thus the modified endogenous NF-YC4 promoter increases the transcription of the endogenous NF-YC4 protein coding sequence in the genetically modified plant or the part from the genetically modified plant, and wherein said genetically modified plant or said part from the genetically modified plant that was modified to increase NF-YC4 expression was selected for increased total protein content due to overexpression of said endogenous NF-YC4 protein as compared to the total protein content in the corresponding wild-type (WT) plant or the corresponding WT part thereof of the same plant species lacking said modified NF-YC4 promoter, and wherein said genetically modified plant, or said part from the genetically modified plant, is non-naturally occurring.

2. The genetically modified plant, or the part from the genetically modified plant, of claim 1, wherein the agent for modifying the NF-YC4 promoter is a zinc-finger nuclease (ZFN) protein, a transcription activator-like effector nuclease (TALEN) protein, an RNA-guided, engineered nuclease (RGENs) complex, a clustered regularly interspaced short palindromic repeat (CRISPR)-Cas complex, a chemical mutagen, or a nucleic acid construct comprising a ZFN protein coding region, a TALEN protein coding region, an RGEN protein coding region and RNA guide sequence, or a Cas protein coding region and a guide sequence.

3. The genetically modified plant, or the part from the genetically modified plant, of claim 1, wherein the transcriptional repressor binding site is modified by a deletion.

4. The genetically modified plant, or the part from the genetically modified plant, of claim 1, wherein the transcriptional repressor binding site is modified by one or more nucleotide substitutions.

5. The genetically modified plant, or the part from the genetically modified plant, of claim 1, wherein the transcriptional repressor binding site comprises an ERF motif, a RAV1 motif, or both an ERF motif and a RAV1 motif.

6. The genetically modified plant, or the part from the genetically modified plant, of claim 1, wherein the genetically modified plant or the part from the genetically modified plant is rice and wherein said transcriptional repressor binding site has (i) two ERF motifs are deleted, (ii) RAV1 motif is deleted, or (iii) a RAV1 motif and an ERF motif are deleted.

7. The genetically modified plant, or the part from the genetically modified plant, of claim 1, wherein the genetically modified plant or the part from the genetically modified plant is soybean and wherein said transcriptional repressor binding site has either (i) two RAV1 motifs are deleted or (ii) a RAV1 motif and an ERF motif are deleted.

8. The genetically modified plant, or the part from the genetically modified plant, of claim 1, wherein the total protein content is increased in the leaves or the seeds of the genetically modified plant or the part from the genetically modified plant.

9. The genetically modified plant, or the part from the genetically modified plant, of claim 1, wherein the genetically modified plant or the part from the genetically modified plant is a crop plant.

10. The genetically modified plant, or the part from the genetically modified plant, of claim 9, wherein the crop plant is soybean, rice, or corn.

11. The genetically modified plant, or the part from the genetically modified plant, of claim 1, wherein the genetically modified plant or the part from the genetically modified plant is a monocot.

12. The genetically modified plant, or the part from the genetically modified plant, of claim 1, wherein the genetically modified plant or the part from the genetically modified plant is a dicot.

13. The genetically modified plant, or the part from the genetically modified plant, of claim 1, wherein the plant is

*Glycine max*, and wherein the NF-YC4 promoter of the endogenous NF-YC4 protein coding sequence comprises SEQ ID NO: 8.

14. The genetically modified plant, or the part from the genetically modified plant, of claim 9, wherein the crop plant is selected from the group consisting of corn, soybean, alfalfa, canola, wheat, rice, potato and lettuce.

15. The genetically modified plant, or the part from the genetically modified plant, of claim 1, wherein the NF-YC4 protein is selected from the group consisting of *Brassica napus* NF-YC4 protein, *Medicago truncatula* NF-Y C4 protein, *Arabidopsis thaliana* NF-YC4 protein, *Glycine max* NF-YC4 protein, *Oryza sativa* NF-YC4 protein, and *Zea mays* NF-YC4 protein.

16. A genetically modified plant progeny obtained from the genetically modified plant, or the part from the genetically modified plant, of claim 1, wherein said genetically modified plant progeny comprises said genetically modified endogenous NF-YC4 promoter and exhibits increasing protein content as compared to a corresponding wild-type control plant of the same plant species lacking said modified NF-YC4 promoter.

\* \* \* \* \*

SEQUENCE LISTING

```
Sequence total quantity: 20
SEQ ID NO: 1              moltype = DNA  length = 1447
FEATURE                   Location/Qualifiers
source                    1..1447
                          mol_type = genomic DNA
                          organism = Oryza sativa
SEQUENCE: 1
gcaagaaccc cagttgagag tggagatggc cattttgttc aggcactagg cagtgggtag    60
gacggtgagg agtgtgtcct gcactcctgc ttcccctgac gatcgatccc catgcgtgcc   120
gaagcatctg atacttttgc tgtgctgttc tttaatttac cctgatactt ttggatatct   180
gaagcagtag agctcgttca ctcaaacagg ctagcctgtt ttgctttctg gtaagaactt   240
aattaactag ttgagatcga catgcatgga tgcgtgaatc tattgttgca ttttttctaa   300
tggatagtta gatttgttcc agcttttttt ttgtcaattc tgttacattt gcagtgtctt   360
caacttctgc atcattcttc tctattcttc cttcactttc tttcttgaac tagaaaagca   420
aaccagagtt cttttcccc ctcttctaca taaacgaaaa cagcttgttg actggctccc    480
tagagctttt tgtaagttga tcatcgaagt agctagttct cttcacttat cagtcatcac   540
tgttctatgt tctatctgca ttttccttga ttttgtactt ttcctgaacg aaaggacaat   600
ccttagccat cataatgcta tgatcgactt attctgaagt catccggcct cgatcctctt   660
ttgtttcggt gagatctgta atggtttagg aaaattatgg atctctgaaa aataagaaac   720
atctagtagt atatgaaatt aagaaatgtc ggaccacgtc aaatcctact ggtatcatat   780
```

-continued

```
accagataac taacttttg aatggaacca aacacgagat tgtgaatata tagcagtaag    840
aaatacaacc ccgaagggta aaggagaaaa aggaaaagca gtttagtgta cgagctgtag    900
gagtagcttt gctcctgcca aggcccagat ccttgcctct tccttcattt ctgcgaggag    960
accaggcact gaggtctcat tgtgatcgaa gattctcctg tttctctcct tccagatctc   1020
ctttgggaac accctgtgtg tttgcaagcg cttagcttca ttttcatgca tgatatgatc   1080
tctggataga agataagtag cccccacaca tgcacttcgc cacctatagc cagcctcgag   1140
ttctcatctg tttgatccgt cgcacatgtg gagcaacgaa gctctagagt acgtctccta   1200
atctctactt acttttgcag tttgcacaca tattgagaaa tgcttatcaa tccttcgatc   1260
tctcacagac aatacctaca agcgtcgttt acactttgca tgtatagcta gccattgtta   1320
catacgtgga gcatgtagcg atcattcgtt cctagcacgt aaattaatcg ccgtaatttt   1380
gcccatgcag acacagcaca cacagctaca aatcgactgt aattaaggta cgtatatata   1440
ggtgaca                                                                 1447
```

SEQ ID NO: 2              moltype = DNA  length = 1441
FEATURE                   Location/Qualifiers
source                    1..1441
                          mol_type = genomic DNA
                          organism = Oryza sativa
SEQUENCE: 2

```
gcaagaaccc cagttgagag tggagatggc cattttgttc aggcactagg cagtgggtag     60
gacggtgagg agtgtgtcct gcactcctgc ttcccctgac gatcgatccc catgcgtgcc    120
gaagcatctg atacttttgc tgtgctgttc tttaatttac cctgatactt ttggatatct    180
gaagcagtag agctcgttca ctcaaacagg ctagcctgtt ttgctttctg gtaagaactt    240
aattaactag ttgagatcga catgcatgga tgcgtgaatc tatatttttt ctaatggata    300
gttagatttg ttccagcttt ttttttgtca attctgttac atttgcagtg tcttcaactt    360
ctgcatcatt cttctctatt cttccttcac tttctttctt gaactagaaa agcaaaccag    420
agttcttttt cccctctcc tacataaacg aaaacagctt gttgactggc tccctagagc    480
tttttgtaag ttgatcatcg aagtagctag ttctcttcac ttatcagtca tcactgttct    540
atgttctatc tgcattttcc ttgattttgt acttttcctg aacgaaagga caatccttag    600
ccatcataat gctatgatcg acttattctg aagtcatccg gcctcgatcc tcttttgttt    660
cggtgagatc tgtaatggtt taggaaaatt atggatctct gaaaaataag aaacatctag    720
tagtatatga aattaagaaa tgtcggacca cgtcaaatcc tactggtatc atataccaga    780
taactaactt tttgaatgga accaaacacg agattgtgaa tatatagcag taagaaatac    840
aaccccgaag ggtaaaggag aaaaaggaaa agcagtttag tgtacgagct gtaggagtag    900
ctttgctcct gccaaggccc agatccttgc ctcttcttc atttctgcga ggagaccagg    960
cactgaggtc tcattgtgat cgaagattct cctgtttctc tccttccaga tctcctttgg   1020
gaacaccctg tgtgtttgca agcgcttagc ttcattttca tgcatgatat gatctctgga   1080
tagaagataa gtagccccca cacatgcact tcgccaccta tagccagcct cgagttctca   1140
tctgtttgat ccgtcgcaca tgtggagcaa cgaagctct cctaatctct cactt         1200
acttactttt gcagtttgca cacatattga gaaatgctta tcaatccttc gatctctcac   1260
agacaatacc tacaagcgtc gtttacactt tgcatgtata gctagccatt gttacatacg   1320
tggagcatgt agcgatcatt cgttcctagc acgtaaatta atcgccgtaa ttttgcccat   1380
gcagacacag cacacacagc tacaaatcga ctgtaattaa ggtacgtata tataggtgac   1440
a                                                                      1441
```

SEQ ID NO: 3              moltype = DNA  length = 1439
FEATURE                   Location/Qualifiers
source                    1..1439
                          mol_type = genomic DNA
                          organism = Oryza sativa
SEQUENCE: 3

```
gcaagaaccc cagttgagag tggagatggc cattttgttc aggcactagg cagtgggtag     60
gacggtgagg agtgtgtcct gcactcctgc ttccctgac gatcgatccc catgcgtgcc     120
gaagcatctg atacttttgc tgtgctgttc tttaatttac cctgatactt ttggatatct    180
gaagcagtag agctcgttca ctcaaacagg ctagcctgtt ttgctttctg gtaagaactt    240
aattaactag ttgagatcga catgcatgga tgcgtgaatc tattgttgca ttttttctaa    300
tggatagtta gatttgttcc agctttttt ttgtcaattc tgttacattt gcagtgtctt    360
caacttctgc atcattcttc tctattcttc cttcactttc tttcttgaac tagaaaagca    420
aaccagagtt cttttcccc ctcttctaca taaacgaaaac agcttgttga ctggcctaga gctt  480
tttgtaagtt gatcatcgaa gtagctagt ctcttcactt atcagtcatc actgttctat       540
gttctatctg cattttcctt gattttgtac ttttcctgaa cgaaaggaca atccttagcc    600
atcataatgc tatgatcgac ttattctgaa gtcatccggc ctcgatcctc ttttgtttcg    660
gtgagatctg taatggttta ggaaaattat ggatctctga aaaataagaa acatctagta    720
gtatatgaaa ttaagaaatg tcggaccacg tcaaatccta ctggtatcat ataccagata    780
actaacttt tgaatggaac caaacacgag attgtgaata tatagcagta agaaatacaa    840
ccccgaaggg taaaggagaa aaaggaaaag cagtttagtg tacgagctgt aggagtagct    900
ttgctcctgc caaggcccag atccttgcct cttccttcat ttctgcgagg agaccaggca    960
ctgaggtctc attgtgatcg aagattctcc tgtttctctc cttccagatc tcctttggga   1020
acaccctgtg tgtttgcaag cgcttagctt cattttcatg catgatatga tctctggata   1080
gaagataagt agcccccaca catgcacttc gccacctata gccagcctcg agttctcatc   1140
tgtttgatcc gtcgcacatg tggagcaacg aagctctaga gtacgtctcc taatctctac   1200
ttacttttgc agtttgcaca catattgaga atgcttatc aatccttcga tctctcacag    1260
acaataccta caagcgtcgt ttacactttg catgtatagc tagccattgt tacatacgtg   1320
gagcatgtag cgatcattcg ttcctagcac gtaaattaat cgccgtaatt ttgcccatgc   1380
agacacagca cacacagcta caaatcgact gtaattaagg tacgtatata taggtgaca   1439
```

SEQ ID NO: 4              moltype = DNA  length = 1336
FEATURE                   Location/Qualifiers
source                    1..1336

-continued

```
                          mol_type = genomic DNA
                          organism = Oryza sativa
SEQUENCE: 4
gcaagaaccc cagttgagag tggagatggc cattttgttc aggcactagg cagtgggtag      60
gacggtgagg agtgtgtcct gcactcctgc ttcccctgac gatcgatccc catgcgtgcc     120
gaagcatctg atacttttgc tgtgctgttc tttaatttac cctgatactt ttggatatct     180
gaagcagtag agctcgttca ctcaaacagg ctagcctgtt ttgctttctg gtaagaactt     240
aattaactag ttgagatcga catgcatgga tgcgtgaatc tattgttgca ttttttctaa     300
tggatagtta gatttgttcc agcttttttt ttgtcaattc tgttacattt gcagtgtctt     360
caacttctgc atcattcttc tctattcttc cttcactttc tttcttgaac tagaaaagca     420
aaccagagtt cttttttcccc ctcttctaca taaacgaaaa cagcttgttg actggctccc     480
tagagctttt tgtaagttga tcatcgaagt agctagttct cttcacttat ctccggcctc     540
gatcctcttt tgtttcggtg agatctgtaa tggtttagga aaattatgga tctctgaaaa     600
ataagaaaca tctagtagta tatgaaatta agaaatgtcg gaccacgtca aatcctactg     660
gtatcatata ccagataact aacttttttga atggaaccaa acacgagatt gtgaatatat     720
agcagtaaga aatacaaccc cgaagggtaa aggagaaaaa ggaaaagcag tttagtgtac     780
gagctgtagg agtagctttg ctcctgccaa ggcccagatc cttgcctctt ccttcatttc     840
tgcgaggaga ccaggcactg aggtctcatt gtgatcgaaa attctcctgt ttctctcctt     900
ccagatctcc tttgggaaca ccctgtgtgt ttgcaagcgc ttagcttcat tttcatgcat     960
gatatgatct ctggatagaa gataagtagc ccccacacat gcacttcgcc acctatagcc    1020
agcctcgagt tctcatctgt ttgatccgtc gcacatgtgg agcaacgaag ctctagagta    1080
cgtctcctaa tctctactta cttttgcagt ttgcacacat attgagaaat gcttatcaat    1140
ccttcgatct ctcacagaca atacctacaa gcgtcgttta cactttgcat gtatagctag    1200
ccattgttac atacgtggag catgtagcga tcattcgttc ctagcacgta aattaatcgc    1260
cgtaattttg cccatgcaga cacagcacac acagctacaa atcgactgta attaaggtac    1320
gtatatatag gtgaca                                                    1336

SEQ ID NO: 5          moltype = DNA  length = 111
FEATURE               Location/Qualifiers
source                1..111
                      mol_type = genomic DNA
                      organism = Oryza sativa
SEQUENCE: 5
agtcatcact gttctatgtt ctatctgcat tttccttgat tttgtacttt tcctgaacga      60
aaggacaatc cttagccatc ataatgctat gatcgactta ttctgaagtc a              111

SEQ ID NO: 6          moltype = DNA  length = 1257
FEATURE               Location/Qualifiers
source                1..1257
                      mol_type = genomic DNA
                      organism = Oryza sativa
SEQUENCE: 6
gcaagaaccc cagttgagag tggagatggc cattttgttc aggcactagg cagtgggtag      60
gacggtgagg agtgtgtcct gcactcctgc ttccctgac gatcgatccc catgcgtgcc     120
gaagcatctg atacttttgc tgtgctgttc tttaatttac cctgatactt ttggatatct     180
gaagcagtag agctcgttca ctcaaacagg ctagcctgtt ttgctttctg gtaagaactt     240
aattaactag ttgagatcga catgcatgga tgcgtgaatc tattgttgca ttttttctaa     300
tggatagtta gatttgttcc agcttttttt ttgtcaattc tgttacattt gcagtgtctt     360
caacttctgc atcattcttc tctattcttc cttcactttc tttcttgaac tagaaaagca     420
aaccagagtt cttttttcccc ctcttctaca tatccggcct cgatcctctt ttgtttcggt     480
gagatctgta atggtttagg aaaattatgg atctctgaaa aataagaaac atctagtagt     540
atatgaaatt aagaaatgtc ggaccacgtc aaatcctact ggtatcatat accagataac     600
taacttttttg aatggaacca aacacgagat tgtgaatata tagcagtaag aaatacaacc     660
ccgaagggta aaggagaaaa aggaaaagca gtttagtgta cgagctgtag gagtagcttt     720
gctcctgcca aggcccagat ccttgcctct tccttcattt ctgcgaggag accaggcact     780
gaggtctcat tgtgatcgaa gattctcctg tttctctcct tccagatctc ctttgggaac     840
accctgtgtg tttgcaagcg cttagcttca ttttcatgca tgatatgatc tctggataga     900
agataagtag ccccacacac tgcacttcgc cacctatagc cagcctcgag ttctcatctg     960
tttgatccgt cgcacatgtg gagcaacgaa gctctagagt acgtctccta atctctactt    1020
acttttgcag tttgcacaca tattgagaaa tgcttatcaa tccttcgatc tctcacagac    1080
aatacctaca agcgtcgttt acactttgca tgtatagcta gccattgtta catacgtgga    1140
gcatgtagcg atcattcgtt cctagcacgt aaattaatcg ccgtaatttt gcccatgcag    1200
acacagcaca cacagctaca atcgactgt aattaaggta cgtatatata ggtgaca        1257

SEQ ID NO: 7          moltype = DNA  length = 190
FEATURE               Location/Qualifiers
source                1..190
                      mol_type = genomic DNA
                      organism = Oryza sativa
SEQUENCE: 7
aacgaaaaca gcttgttgac tggctcccta gagctttttg taagttgatc atcgaagtag      60
ctagttctct tcacttatca gtcatcactg ttctatgttc tatctgcatt ttccttgatt     120
ttgtactttt cctgaacgaa aggacaatcc ttagccatca taatgctatg atcgacttat     180
tctgaagtca                                                            190

SEQ ID NO: 8          moltype = DNA  length = 1176
FEATURE               Location/Qualifiers
source                1..1176
                      mol_type = genomic DNA
```

-continued

```
                            organism = Glycine max
SEQUENCE: 8
taatataata taagaatttg taaattataa acctaaaaaa ggtgcatacc aaatgaatag   60
tttatttcaa aagcaaagat aaattttata cacaaaagtg acaaaatgtg gacttgaaaa   120
tcacatgcta gagcaaagca aggttcagat gaagccataa ggctagaacg taaatgctgc   180
aaaaatcaat tatatttgaa tctcacgggc attgaacaaa agagaatgga cccatcaatg   240
gggcattgac atggatggat ggaacaccct catagtcaca tgccacaaca gagtaacgct   300
aaacaaaatg tattaacaaa aactatagga tcatgctttc ttaatttaaa aacataggtg   360
gtcagttttt gttaacatta attttttagga ttatttgttg aagacaaata tggaaggttt   420
ataataattt atgtgcatta ctcaatgtaa tccttaaaat gaaaataact aaactttttt   480
tttttggata gttaaacaac tacgaagcta aatgaataat taaatcaata ttaatttga   540
ttaaaaataa gattaataat atccctaata ttgtgaacaa actttgttgg taatgtaaaa   600
aaaattaaaa gaaacaagat taaattacgt atttaataat ttaagattaa tgttgtttaa   660
tttgattttt taaatattta tctttctttt gaatttgatt ctttagttca cttaagatta   720
tgatcgttaa taattctaaa agataaatgt catcaatctt gaattgattg aaagattaaa   780
ttaaataaaa agaattaaga taaatgatga aaatacattt aaaaaataag atgaaacaaa   840
atgtgtcatt taaccaaaaa aaaaaggaaa aataaattaa aaaaaggaac ttaccttcc    900
cctcaaaaaa gaaaagaaaa aaaaaaggaa acttaccct ggttgttccg ttgaaattga    960
aaaaacaaac cctaaactta ccttaaccta ggtcctaggg cactggtcgg atatgttatt   1020
gtttagttta ccttatccca ccacatacat agttttttttt ttcttaaatt tcccaatcaa   1080
ttccatccat cgggtcttta ctctcttacc caacccacac acactctttc tctctctctc   1140
tttccctgat catcaaaatc agaaaaaatt ggggga                             1176

SEQ ID NO: 9              moltype = DNA   length = 1159
FEATURE                  Location/Qualifiers
source                   1..1159
                         mol_type = genomic DNA
                         organism = Glycine max
SEQUENCE: 9
taatataata taagaatttg taaattataa acctaaaaaa ggtgcatacc aaatgaatag   60
tttatttcaa aagcaaagat aaattttata cacaaaagtg acaaaatgtg gacttgaaaa   120
tcacatgcta gagcaaagca aggttcagat gaagccaaat ggctagaacg taaatgctgc   180
aaaaatcaat tatatttgaa tctcacgggc attgaacaaa agagaatgga cccatcaatg   240
gggcattgac atggatggat ggaacaccct catgagtaac tgtaaacaaa atgtattaac   300
aaaaactata ggatcatgct tcttaattt aaaaacatag gtggtcagtt tttgttaaca   360
ttaattttta ggattatttg ttgaagacaa atatggaagg tttataataa tttatgtgca   420
ttactcaatg taatccttaa aatgaaaata actaaacttt ttttttttgg atagttaaac   480
aactacgaag ctaaatgaat aattaaatca atattaattt tgattaaaaa taagattaat   540
aatatcccta atattgtgaa caaactttgt tggtaatgta aaaaaaatta aagaaacaa    600
gattaaaatta cgtatttaat aatttaagat taatgttgtt taatttgatt ttttaaatat   660
ttatctttct tttgaatttg attctttagt tcacttaaga ttatgatcgt taataattct   720
aaaagataaa tgtgtcatcaat cttgaattga ttgaaagatt aaattaaata aaaagaatta   780
agataaatga tgaaaataca tttaaaaaat aagatgatgtc atttaaccaa   840
aaaaaaaagg aaaaataaat taaaaaaagg aacttaccct tcccctcaaa aagaaaaga   900
aaaaaaaaaa ggaacttacc cttggttgtt ccgttgaaat tgaaaaaaca aaccctaaac   960
ttaccttaac ctaggtccta gggcactggt cggatatgtt attgtttagt ttaccttatc   1020
ccaccacata catagttttt ttttttctta aatttcccaat caattccatc catcgggtct   1080
ttactctctt acccaaccca cacacactct ttctctctct ctctttccct gatcatcaaa   1140
atcagaaaaa attgggga                                                 1159

SEQ ID NO: 10             moltype = DNA   length = 17
FEATURE                  Location/Qualifiers
source                   1..17
                         mol_type = genomic DNA
                         organism = Glycine max
SEQUENCE: 10
agtcacatgc cacaaca                                                   17

SEQ ID NO: 11             moltype = DNA   length = 1135
FEATURE                  Location/Qualifiers
source                   1..1135
                         mol_type = genomic DNA
                         organism = Glycine max
SEQUENCE: 11
taatataata taagaatttg taaattataa acctaaaaaa ggtgcatacc aaatgaatag   60
tttatttcaa aagcaaagat aaattttata cacaaaagtg acaaaatgtg gacttgaaaa   120
tcacatgcta gagcaaagca aggttcagat gaagccaaat ggctagaacg taaatgctgc   180
aaaaatcaat tatatttgaa tctcacgggc attgaacaaa agagaatgga cccatcaatg   240
gggcattgac atggatggat ggaacaccct catagtcaca tgccacaaca gagtaacgct   300
aaacaaaatg tattaacaaa aactatagga tcatgctttc ttaatttaaa aacataggta   360
agacaaatat ggaaggttta ataatttta tgtgcattac tcaatgtaat ccttaaaatg   420
aaaataacta aactttttttt ttttggatag ttaaacaact acgaagctaa atgaataatt   480
aaatcaatat taattttgat taaaaataag attaataata tccctaatat tgtgaacaaa   540
ctttgttggt aatgtaaaaa aaattaaaag aaacaagatt aaaattacgt atttaataat   600
taagattaat gttgtttaat ttgatttttt aaatatttat ctttctttttg aatttgattc   660
tttagttcac ttaagattat gatcgttaat aattctaaaa gataaatgtc atcaatcttg   720
aattgattga aagattaaat taaataaaaa gaattaagat aaatgatgaa aatacattta   780
aaaaataaga tgaaacaaa tgtgtcattt aaccaaaaaa aaaaggaaaa ataaattaaa   840
aaaggaact taccctttccc ctcaaaaaag aaaagaaaaa aaaaaggaa cttaccttg    900
```

```
gttgttccgt tgaaattgaa aaaacaaacc ctaaacttac cttaacctag gtcctagggc   960
actggtcgga tatgttattg tttagtttac cttatcccac cacatacata gtttttttt    1020
tcttaaattt cccaatcaat tccatccatc gggtctttac tctcttaccc aacccacaca   1080
cactctttct ctctctctct ttccctgatc atcaaaatca gaaaaaattg gggga          1135

SEQ ID NO: 12                moltype = DNA   length = 41
FEATURE                      Location/Qualifiers
source                       1..41
                             mol_type = genomic DNA
                             organism = Glycine max
SEQUENCE: 12
ggtcagtttt tgttaacatt aattttagg attatttgtt g                          41

SEQ ID NO: 13                moltype = DNA   length = 1105
FEATURE                      Location/Qualifiers
source                       1..1105
                             mol_type = genomic DNA
                             organism = Glycine max
SEQUENCE: 13
taatataata taagaatttg taaattataa acctaaaaaa ggtgcatacc aaatgaatag     60
tttatttcaa aagcaaagat aaattttata cacaaaagtg acaaaatgtg gacttgaaaa    120
tcacatgcta gagcaaagca aggttcagat gaagccaaat ggctagaacg taaatgctgc   180
aaaaatcaat tatatttgaa tctcacgggc attgaacaaa agagaatgga cccatcaatg   240
gggcattgac atggatggat ggaacaccct catagtcaca tgccacaaca gagtaacgct   300
aaacaaaatg tattaacaaa aactatagga tcatgctttc ttaatttaaa aacataggtg   360
gtcagttttt gttaacatta attttttagga ttatttgttg aagacaaata tggaaggttt   420
ataataattt atgtgcatta ctcaatgtaa tccttaaaat gaaaataact aaactttttt   480
tttttggata gttaaacaac tacgaagcta aatgaataat taaatcaata ttaatttga    540
ttaaaaataa gattaataat atccctaata ttgtgaacaa acttttttaat ttgattttt    600
aaatatttat ctttctttg aatttgattc tttagttcac taagattat gatcgttaat    660
aattctaaaa gataaatgtc atcaatcttg aattgattga aagattaaat taaataaaaa   720
gaattaagat aaatgatgaa aatacatttta aaaaataaga tgaaacaaaa tgtgtcattt   780
aaccaaaaaa aaaaggaaaa ataaattaaa aaaggaact tacccttccc ctcaaaaaag   840
aaaagaaaaa aaaaaaggaa cttacccttg gttgttccgt tgaaattgaa aaaacaaacc    900
ctaaacttac cttaacctag gtcctagggc actggtcgga tatgttattg tttagtttac   960
cttatcccac cacatacata gttttttttt tcttaaattt cccaatcaat tccatccatc   1020
gggtctttac tctcttaccc aacccacaca cactctttct ctctctctct ttccctgatc   1080
atcaaaatca gaaaaaattg gggga                                          1105

SEQ ID NO: 14                moltype = DNA   length = 71
FEATURE                      Location/Qualifiers
source                       1..71
                             mol_type = genomic DNA
                             organism = Glycine max
SEQUENCE: 14
tgttggtaat gtaaaaaaaa ttaaaagaaa caagattaaa ttacgtattt aataatttaa    60
gattaatgtt g                                                          71

SEQ ID NO: 15                moltype = DNA   length = 586
FEATURE                      Location/Qualifiers
source                       1..586
                             mol_type = other DNA
                             organism = Arabidopsis thaliana
SEQUENCE: 15
ctcagaagaa gcctcctttc gatctgtcag ccattgaaga aacctccttt cgatctgtca     60
gccattgaag atcagaagaa acaagactca cacggtcagc cattgaagaa gcctcctctc    120
attacctctc atcaaacatc tagatctgta cccaaacctt atcccttttt ccttatttct    180
cgctttgtct attcttaatc tgattaatac ttgttgttgt tccaggttat agaagatctg    240
ggtgtgttta tatgcttcat tttctccaca gcgaccagtt ggtgtttggt tcttagattc    300
atgaagacca atagagagca ggaaatttac gttgaaagaa gcttcaaacc aaacaattca    360
acaattcaga atttgatgga cattgaaagg ttcattttgc ctcacacttc tacatcaggt    420
gtcgcaaggc tcaaaatgag ggtcatatca tgggtcgggc ttcagttcta caactactga    480
tattgggcct tatcacaaat tagttatagg gccattgtat ccaatattta atatctctgt    540
aaacttgttt aatggttatt ttgttctaat gcccattaca actaga                   586

SEQ ID NO: 16                moltype = AA   length = 59
FEATURE                      Location/Qualifiers
source                       1..59
                             mol_type = protein
                             organism = Arabidopsis thaliana
SEQUENCE: 16
MKTNREQEIY VERSFKPNNS TIQNLMDIER FILPHTSTSG VARLKMRVIS WVGLQFYNY      59

SEQ ID NO: 17                moltype = DNA   length = 32
FEATURE                      Location/Qualifiers
source                       1..32
                             mol_type = genomic DNA
                             organism = Glycine max
SEQUENCE: 17
```

-continued

```
ggtcagtttt tgttaacatt aatttttagg at                                        32

SEQ ID NO: 18              moltype = DNA   length = 20
FEATURE                    Location/Qualifiers
source                     1..20
                           mol_type = other DNA
                           organism = synthetic construct
SEQUENCE: 18
cctcccaggc atggcagtcc                                                      20

SEQ ID NO: 19              moltype = DNA   length = 18
FEATURE                    Location/Qualifiers
source                     1..18
                           mol_type = other DNA
                           organism = synthetic construct
SEQUENCE: 19
ccatcaaggc tccgctgg                                                        18

SEQ ID NO: 20              moltype = DNA   length = 1034
FEATURE                    Location/Qualifiers
source                     1..1034
                           mol_type = genomic DNA
                           organism = Zea mays
SEQUENCE: 20
agggccctgc agcggcggca gctggcggga gagaggcttg ggactgggcc gcccggccgc    60
gaggaataaa ctcactcctg tcttcatacg tatccatagc cggcaggcgg cagtacctgt   120
atgtggtttt agctatacgc gacctcagtt cgggcgcaag gttagtcttc gatttaagca   180
tagattttat tttatcttct tggctccacc aaataacact aacaaaatcg ctttggcttc   240
tatgggttca aattaagcac tggatcgtac cattttcttg ttcatttata ctttgtcatc   300
caatccacac cgattaattt ctcacggtca acaacgcatg aagtttcat ttctgggaag     360
aagcatgtat ttttttatc tccgactcga tctagtggtg agaggaggaa gatgaatagt    420
gcatgcatat gatatctaga gaggcaccag atctagtggc tccatgttct gttcgcgggc   480
taagaaaaaa cataaacaag caggcgcctg aaaaatagct agtccctaac tttttagacc   540
aatctgtatg tttattttga cgatattggt atgaaaagt ctctcaagaa caatatacat    600
atgcagcatg catgtgcatg gtataattat aaattattag cagagtttag ataagtaggc   660
ccccacgtct gcgctccgcc acctacagcg agcctccctt tcctccctcc ctgattcgtt   720
tgcacttgct gagagctcaa cagaatttgg tcaccgattt caattcgcag ctactaattc   780
tcaccacatt gaaattttcg atttgaaaca gtacaatttc tgaagagaaa ttgtacgtct   840
gaaacggttg catgtgtact atgaactgct agccattccc tgcatacgtg ggacacgctc   900
agatcattca ttcgcagcac gtacgtaacc ttaatattct actatacatc catgcagcta   960
caaccccgac caggcgagaa gaagcatcga tagtgtgacg agctaacccca ccaccagcaa  1020
cgtaatccaa atcc                                                          1034
```